United States Patent
Webb et al.

(10) Patent No.: US 7,074,617 B1
(45) Date of Patent: Jul. 11, 2006

(54) MHC CLASS II ANTIGEN-PRESENTING SYSTEMS AND METHODS FOR ACTIVATIND CD4+T CELLS

(75) Inventors: Susan R. Webb, Leucadia, CA (US); Ola Wingvist, Uppsala (SE); Lars Karlsson, La Jolla, CA (US); Michael R. Jackson, Del Mar, CA (US); Per A. Peterson, Rancho Santa Fe, CA (US)

(73) Assignee: The Scripps Research Institute, La Jolla, CA (US)

( * ) Notice: Subject to any disclaimer, the term of this patent is extended or adjusted under 35 U.S.C. 154(b) by 487 days.

(21) Appl. No.: 09/715,891

(22) Filed: Nov. 17, 2000

Related U.S. Application Data

(62) Division of application No. 09/194,285, filed as application No. PCT/US97/08697 on May 22, 1997, now Pat. No. 6,355,479.

(60) Provisional application No. 60/018,175, filed on May 23, 1996.

(51) Int. Cl.
*C12N 15/12* (2006.01)
*C12N 5/06* (2006.01)
*C12N 15/63* (2006.01)
*C07H 21/04* (2006.01)

(52) U.S. Cl. ............... 435/455; 435/348; 435/320.1; 536/23.5

(58) Field of Classification Search ........... 435/455, 435/320.1, 348; 536/23.1, 23.5
See application file for complete search history.

(56) References Cited

U.S. PATENT DOCUMENTS

| | | | |
|---|---|---|---|
| 5,242,687 A | 9/1993 | Tykocinski et al. | |
| 5,314,813 A | 5/1994 | Peterson et al. | |
| 5,395,760 A | 3/1995 | Smith et al. | |
| 5,529,921 A | 6/1996 | Peterson et al. | |
| 5,583,031 A | 12/1996 | Stern | |

FOREIGN PATENT DOCUMENTS

WO WO 96/12009 4/1996

OTHER PUBLICATIONS

Janeway et al. Immunobiology Garland Press NY (1997) pp. 7:7, 7:8 and 7:25.*
Galvin, et al., "Murine B7 Antigen Provides a Sufficient Costimulatory Signal for Antigen-Specific and MHC-Restricted T Cell Activation". *The Journal of Immunology* 149 : 3802-3808 (1992).
Baskar, et al, "Tumor Cells Expressing Major Histocompatibility Complex Class II and B7 Activation Molecules Stimulate Potent Tumor-Specific Immunity", *Journal of Immunotherapy* 14: 209-215 (1993).
Hemler, et al., Adhesive protein receptors in hematopoietic cells, 1998, *Immunology Today,* 9(4):109-114.
Ratnofsky, et al., Expression and function of CD8 in a murine T cell hybridoma, 1987, *J. Exp. Med.,* 166:1747-1757.
Sette, et al., Antigen analogs/MHC complexes as specific T cell receptor antagonists, 1994, *Annu. Rev. Immunol.,* 12:413-431.
Tan, et al., Induction of alloantigen-specific hyporesponsiveness in human T lymphocytes by blocking interaction of CD28 with its natural ligand B7/BB1, 1993, *J. Exp. Med.,* 177:165-173.
Brown, et al., CD27-CD27 ligand/CD70 interactio ns enhance alloantigen-induced proliferation cytolytic activity in CD8+ T lymphocytes, 1995, *J. Immunol.,* 154:3686-3695.
Morris, et al., An essential role for HLA-DM in antigen presentation by class II major histocompatability molecules, 1994, *Nature,* 368:551-554.

* cited by examiner

*Primary Examiner*—Christina Chan
*Assistant Examiner*—F. Pierre VanderVegt
(74) *Attorney, Agent, or Firm*—Thomas Fitting; Michael J. McCarthy

(57) ABSTRACT

The present invention relates to synthetic antigen-presenting matrices, their methods of making and their methods of use. One such matrix is cells that have been transfected to produce MHC antigen-presenting molecules with one or more accessory molecules. The matrices are used to activate naive CD4+T cells as well as shift the ongoing activation state into a preferred differentiated population of either Th1 or Th2 cells.

24 Claims, 8 Drawing Sheets

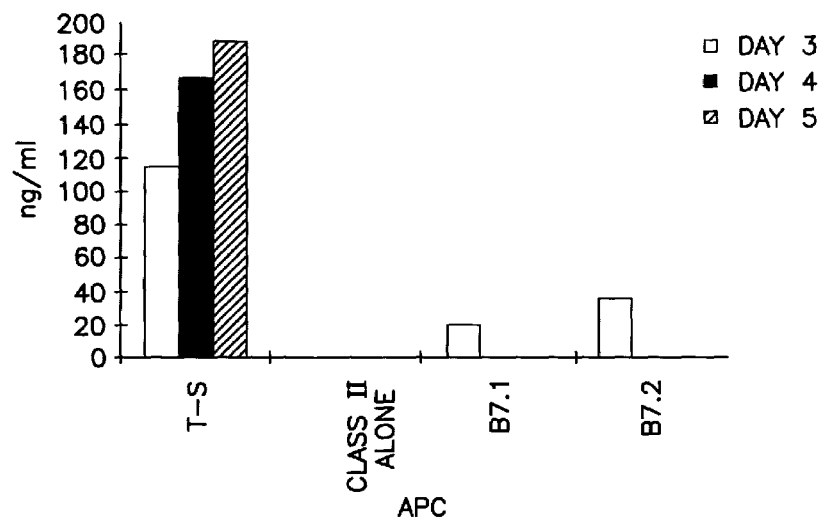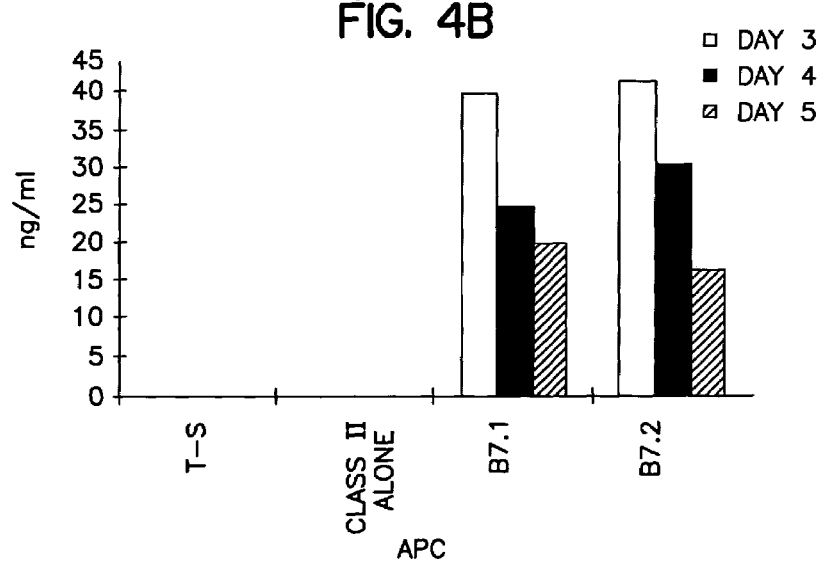

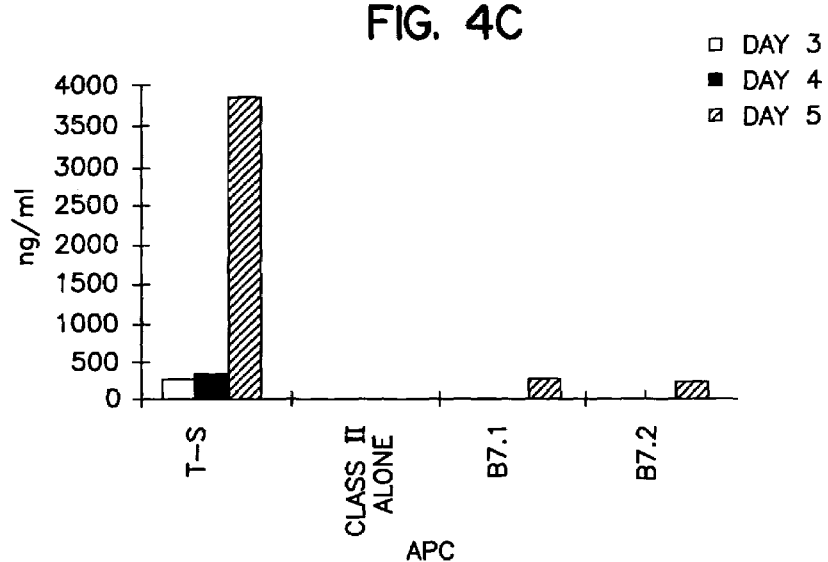
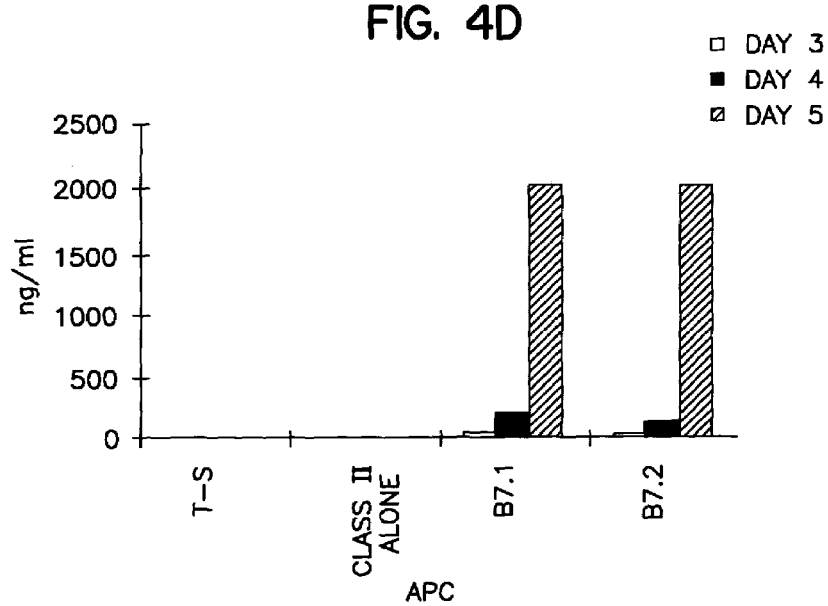

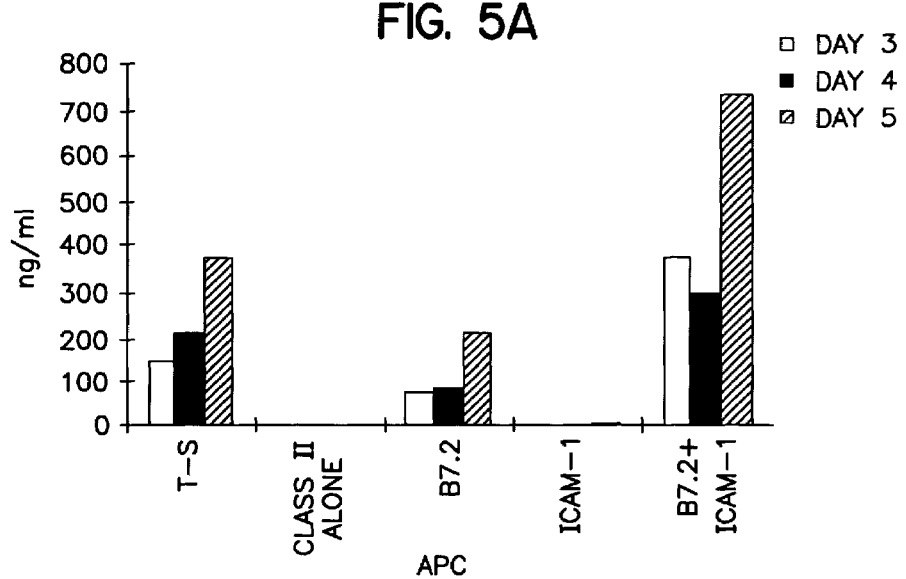
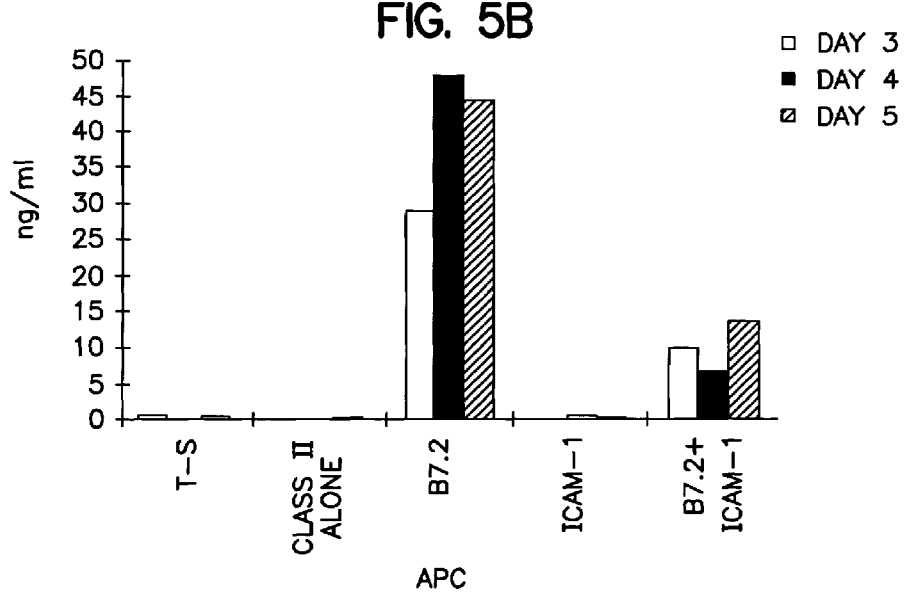

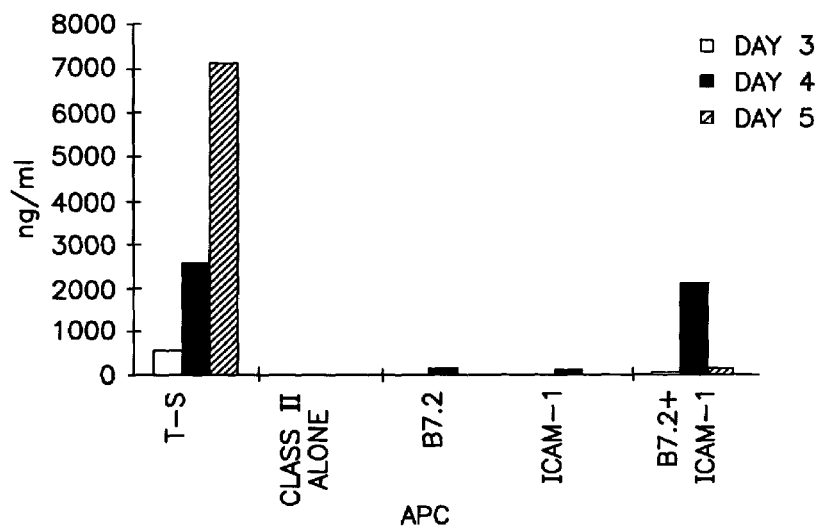
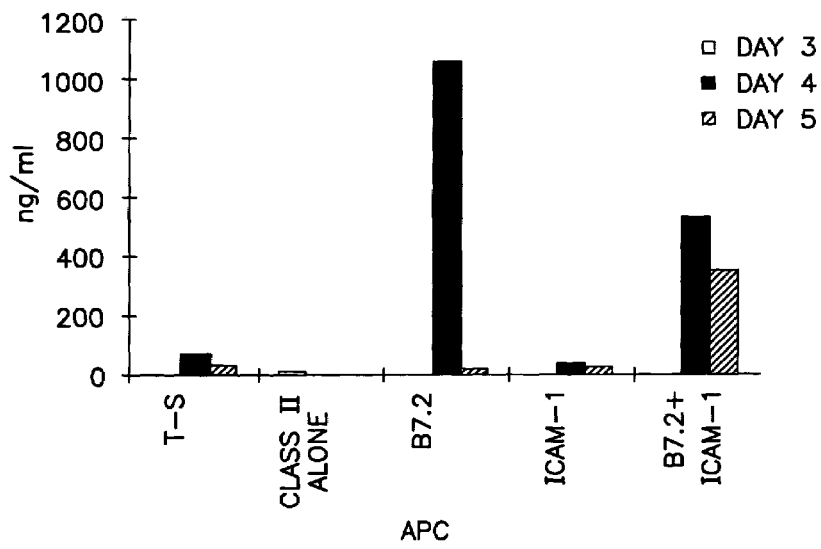

SEQUENCE LISTING

<160> NUMBER OF SEQ ID NOS: 56

<210> SEQ ID NO 1
<211> LENGTH: 740
<212> TYPE: DNA
<213> ORGANISM: Drosophila melanogaster

<400> SEQUENCE: 1

```
attcgatgca cactcacatt cttctcctaa tacgataata aaactttcca tgaaaaatat      60
ggaaaaatat atgaaaattg agaaatccaa aaaactgata aacgctctac ttaattaaaa     120
tagataaatg ggagcggctg gaatggcgga gcatgaccaa gttcctccgc caatcagtcg     180
taaaacagaa gtcgtggaaa gcggatagaa agaatgttcg atttgacggg caagcatgtc     240
tgctatgtgg cggattgcgg aggaattgca ctggagacca gcaaggttct catgaccaag     300
aatatagcgg tgtgagtgag cgggaagctc ggtttctgtc cagatcgaac tcaaaactag     360
tccagccagt cgctgtcgaa actaattaag ttaatgagtt tttcatgtta gtttcgcgct     420
gagcaacaat taagtttatg tttcagttcg gcttagattt cgctgaagga cttgccactt     480
tcaatcaata ctttagaaca aaatcaaaac tcattctaat agcttggtgt tcatcttttt     540 tttaatgat aagcattttg tcgtttatac tttttatatt tcgatattaa accacctatg     600
aagttcattt taatcgccag ataagcaata tattgtgtaa atatttgtat tctttatcag     660
gaaattcagg gagacgggga agttactatc tactaaaagc caaacaattt cttacagttt     720
tactctctct actctagagt                                                  740
```

<210> SEQ ID NO 2
<211> LENGTH: 427
<212> TYPE: DNA
<213> ORGANISM: Drosophila melanogaster

<400> SEQUENCE: 2

```
aattcgttgc aggacaggat gtggtgcccg atgtgactag ctctttgctg caggccgtcc      60
```

```
tatcctctgg ttccgataag agacccagaa ctccggcccc ccaccgccca ccgccacccc    120
catacatatg tggtacgcaa gtaagagtgc ctgcgcatgc cccatgtgcc ccaccaagag    180
ttttgcatcc catacaagtc cccaaagtgg agaaccgaac caattcttcg cgggcagaac    240
aaaagcttct gcacacgtct ccactcgaat tggagccgg ccggcgtgtg caaaagaggt    300
gaatcgaacg aaagacccgt gtgtaaagcc gcgtttccaa aatgtataaa accgagagca    360
tctggccaat gtgcatcagt tgtggtcagc agcaaaatca agtgaatcat ctcagtgcaa    420
ctaaagg                                                              427
```

<210> SEQ ID NO 3
<211> LENGTH: 35
<212> TYPE: DNA
<213> ORGANISM: Artificial Sequence
<220> FEATURE:
<223> OTHER INFORMATION: synthesized

<400> SEQUENCE: 3

```
cttgaattcc accatgccgt gcagcagagc tctga                                35
```

<210> SEQ ID NO 4
<211> LENGTH: 29
<212> TYPE: DNA
<213> ORGANISM: Artificial Sequence
<220> FEATURE:
<223> OTHER INFORMATION: synthesized

<400> SEQUENCE: 4

```
tttggatcct cataaaggcc ctgggtgtc                                       29
```

<210> SEQ ID NO 5
<211> LENGTH: 32
<212> TYPE: DNA
<213> ORGANISM: Artificial Sequence
<220> FEATURE:
<223> OTHER INFORMATION: synthesized

<400> SEQUENCE: 5

```
cttgaattcc accatggctc tgcagatccc ca                                   32
```

<210> SEQ ID NO 6
<211> LENGTH: 28
<212> TYPE: DNA
<213> ORGANISM: Artificial Sequence
<220> FEATURE:
<223> OTHER INFORMATION: synthesized

<400> SEQUENCE: 6

```
tttggatcct cactgcagga gccctgct                                        28
```

<210> SEQ ID NO 7
<211> LENGTH: 4713
<212> TYPE: DNA
<213> ORGANISM: Mus musculus

<400> SEQUENCE: 7

```
gcgttgcagg acaggatgtg gtgcccgatg tgactagctc tttgctgcag gccgtcctat    60
cctctggttc cgataagaga cccagaactc cggcccccca ccgccaccg ccaccccat     120 acatatgtgg tacgcaagta agagtgcctg cgcatgcccc atgtgcccca ccaagagttt    180
tgcatcccat acaagtcccc aaagtggaga accgaaccaa ttcttcgcgg gcagaacaaa    240
agcttctgca cacgtctcca ctcgaatttg agccggccg gcgtgtgcaa aagaggtgaa    300
```

```
tcgaacgaaa gacccgtgtg taaagccgcg tttccaaaat gtataaaacc gagagcatct    360
ggccaatgtg catcagttgt ggtcagcagc aaaatcaagt gaatcatctc agtgcaacta    420
aaggggggaa ttcctgcaga gacctcccag agaccaggag gccgtgcagc agagctctga    480
ttctggggt cctcgccctg aacaccatgc tcagcctctg cggaggtgaa gacgacattg     540
aggccgacca cgtaggcttc tatggtacaa ctgtttatca gtctcctgga gacattggcc    600
agtacacaca tgaatttgat ggtgatgagt tgttctatgt ggacttggat aagaagaaaa    660
ctgtctggag gcttcctgag tttggccaat gatactctt tgagcccaa ggtgactgc       720
aaaacatagc tgcagaaaaa cacaacttgg gaatcttgac taagaggtca aatttcaccc    780
cagctaccaa tgaggctcct caagcgactg tgttccccaa gtcccctgtg ctgctgggtc    840
agcccaacac ccttatctgc tttgtggaca acatcttccc acctgtgatc aacatcacat    900
ggctcaggaa tagcaagtca gtcacagacg gcgtttatga gaccagcttc ctcgtcaacc    960
gtgaccattc cttccacaag ctgtcttatc tcaccttcat cccttctgat gatgacattt   1020
atgactgcaa ggtggagcac tggggcctgg aggagccggt tctgaaacac tgggaacctg   1080
agattccagc ccccatgtca gagctgacag aaactgtggt gtgtgccctg gggttgtctg   1140
tgggccttgt gggcatcgtg gtgggcacca tcttcatcat tcaaggcctg cgatcaggtg   1200
gcacctccag acacccaggg cctttatgag tcacaccctg gaaaggaagg tgtgtgtccc   1260
tcttcatgga agaagtggtg ttctgggtgt cgaattcgag ctcggtaccc ggggatcctc   1320
tagagtcgac ctgcaggcat gcaattcgat gcacactcac attcttctcc taatacgata   1380
ataaactttt ccatgaaaaa tatgaaaaaa tatatgaaaa ttgagaaatc caaaaaactg   1440
ataaacgctc tacttaatta aaatagataa atgggagcgg caggaatggc ggagcatggc   1500
caagttcctc cgccaatcag tcgtaaaaca gaagtcgtgg aaagcggata gaaagaatgt   1560
tcgatttgac gggcaagcat gtctgctatg tggcggattg cggaggaatt gcactggaga   1620
ccagcaaggt tctcatgacc aagaatatag cggtgagtga gcgggaagct cggtttctgt   1680
ccagatcgaa ctcaaaacta gtccagccag tcgctgtcga aactaattaa gtaaatgagt   1740
ttttcatgtt agtttcgcgc tgagcaacaa ttaagtttat gtttcagttc ggcttagatt   1800
tcgctgaagg acttgccact ttcaatcaat acttagaac aaaatcaaaa ctcattctaa    1860
tagcttggtg ttcatctttt tttttaatga taagcatttt gtcgtttata cttttatat    1920
ttcgatatta aaccacctat gaagttcatt ttaatcgcca gataagcaat atattgtgta   1980
aatatttgta ttctttatca ggaaattcag ggagacgggg aagttactat ctactaaaag   2040
ccaaacaatt tcttacagtt ttactctctc tactctagag cttggcactg gccgtcgttt   2100
tacaacgtcg tgactgggaa aaccctggcg ttacccaact taatcgcctt gcagcacatc   2160
cccctttcgc cagctggcgt aatagcgaag aggcccgcac cgatcgccct tcccaacagt   2220
tgcgcagcct gaatggcgaa tggcgcctga tgcggtattt tctccttacg catctgtgcg   2280
gtatttcaca ccgcatatgg tgcactctca gtacaatctg ctctgatgcc gcatagttaa   2340
gccagccccg acacccgcca cacccgctg acgcgccctg acgggcttgt ctgctcccgg   2400
catccgctta cagacaagct gtgaccgtct ccgggagctg catgtgtcag aggttttcac   2460
cgtcatcacc gaaacgcgcg agacgaaagg gcctcgtgat acgcctattt ttataggtta   2520
atgtcatgat aataatggtt tcttagacgt caggtggcac ttttcgggga atgtgcgcg    2580
gaacccctat ttgtttattt ttctaaatac attcaaatat gtatccgctc atgagacaat   2640
```

-continued

```
aaccctgata aatgcttcaa taatattgaa aaaggaagag tatgagtatt caacatttcc    2700
gtgtcgccct tattcccttt tttgcggcat tttgccttcc tgttttttgct cacccagaaa   2760 cgctggtgaa agtaaaagat gctgaagatc agttgggtgc acgagtgggt tacatcgaac    2820
tggatctcaa cagcggtaag atccttgaga gttttcgccc cgaagaacgt tttccaatga    2880
tgagcacttt taaagttctg ctatgtggcg cggtattatc ccgtattgac gccgggcaag    2940
agcaactcgg tcgccgcata cactattctc agaatgactt ggttgagtac tcaccagtca    3000
cagaaaagca tcttacggat ggcatgacag taagagaatt atgcagtgct gccataacca    3060
tgagtgataa cactgcggcc aacttacttc tgacaacgat cggaggaccg aaggagctaa    3120 ccgcttttt gcacaacatg ggggatcatg taactcgcct tgatcgttgg gaaccggagc     3180
tgaatgaagc cataccaaac gacgagcgtg acaccacgat gcctgtagca atggcaacaa    3240
cgttgcgcaa actattaact ggcgaactac ttactctagc ttcccggcaa caattaatag    3300
actggatgga ggcggataaa gttgcaggac cacttctgcg ctcggccctt ccggctggct    3360
ggtttattgc tgataaatct ggagccggtg agcgtgggtc tcgcggtatc attgcagcac    3420
tggggccaga tggtaagccc tcccgtatcg tagttatcta cacgacgggg agtcaggcaa    3480
ctatggatga acgaaataga cagatcgctg agataggtgc ctcactgatt aagcattggt    3540
aactgtcaga ccaagtttac tcatatatac tttagattga tttaaaactt catttttaat    3600
ttaaaaggat ctaggtgaag atcctttttg ataatctcat gaccaaaatc ccttaacgtg    3660
agttttcgtt ccactgagcg tcagaccccg tagaaaagat caaaggatct tcttgagatc    3720
ctttttttct gcgcgtaatc tgctgcttgc aaacaaaaaa accaccgcta ccagcggtgg    3780
tttgtttgcc ggatcaagag ctaccaactc tttttccgaa ggtaactggc ttcagcagag    3840
cgcagatacc aaatactgtc cttctagtgt agccgtagtt aggccaccac ttcaagaact    3900
ctgtagcacc gcctacatac ctcgctctgc taatcctgtt accagtggct gctgccagtg    3960
gcgataagtc gtgtcttacc gggttggact caagacgata gttaccggat aaggcgcagc    4020
ggtcgggctg aacggggggt tcgtgcacac agcccagctt ggagcgaacg acctacaccg    4080
aactgagata cctacagcgt gagcattgag aaagcgccac gcttcccgaa gggagaaagg    4140
cggacaggta tccggtaagc ggcagggtcg gaacaggaga gcgcacgagg gagcttccag    4200
ggggaaacgc ctggtatctt tatagtcctg tcgggtttcg ccacctctga cttgagcgtc    4260
gatttttgtg atgctcgtca ggggggcgga gcctatggaa aaacgccagc aacgcggcct    4320
ttttacggtt cctggccttt tgctggcctt ttgctcacat gttctttcct gcgttatccc    4380
ctgattctgt ggataaccgt attaccgcct ttgagtgagc tgataccgct cgccgcagcc    4440
gaacgaccga gcgcagcgag tcagtgagcg aggaagcgga agagcgccca atacgcaaac    4500
cgcctctccc cgcgcgttgg ccgattcatt aatgcagctg gcacgacagg tttcccgact    4560
ggaaagcggg cagtgagcgc aacgcaatta atgtgagtta gctcactcat taggcacccc    4620
aggctttaca ctttatgctt ccggctcgta tgttgtgtgg aattgtgagc ggataacaat    4680
ttcacacagg aaacagctat gaccatgatt acg                                 4713
```

<210> SEQ ID NO 8
<211> LENGTH: 4724
<212> TYPE: DNA
<213> ORGANISM: Mus musculus

<400> SEQUENCE: 8

```
gcgttgcagg acaggatgtg gtgcccgatg tgactagctc tttgctgcag gccgtcctat    60
```

-continued

```
cctctggttc cgataagaga cccagaactc cggcccccca ccgcccaccg ccaccccat    120
acatatgtgg tacgcaagta agagtgcctg cgcatgcccc atgtgcccca ccaagagttt    180
tgcatcccat acaagtcccc aaagtggaga accgaaccaa ttcttcgcgg gcagaacaaa    240
agcttctgca cacgtctcca ctcgaatttg agccggccg gcgtgtgcaa aagaggtgaa    300
tcgaacgaaa gacccgtgtg taaagccgcg tttccaaaat gtataaaacc gagagcatct    360
ggccaatgtg catcagttgt ggtcagcagc aaaatcaagt gaatcatctc agtgcaacta    420
aagggggaa ttccctgctg tgccctagag atggctctgc agatccccag cctcctcctc    480
tcagctgctg tggtggtgct gatggtgctg agcagcccag ggactgaggg cggaaactcc    540
gaaaggcatt tcgtggtcca gttcaagggc gagtgctact acaccaacgg gacgcagcgc    600
atacggctcg tgaccagata catctacaac cgggaggagt acgtgcgcta cgacagcgac    660
gtgggcgagt accgcgcggt gaccgagctg gggcggccag acgccgagta ctggaacagc    720
cagccggaga tcctggagcg aacgcgggcc gaggtggaca cggcgtgcag acacaactac    780
gaggggccgg agaccagcac ctccctgcgg cggcttgaac agcccaatat cgccatctcc    840
ctgtccagga cagaggccct caaccaccac aacactctgg tctgttcggt gacagatttc    900
tacccagcca agatcaaagt gcgctggttc aggaatggcc aggaggagac agtgggggtc    960
tcatccacac agcttattag gaatggggac tggaccttcc aggtcctggt catgctggag   1020
atgacccctc atcagggaga ggtctacacc tgccatgtgg agcatccag cctgaagagc   1080
cccatcactg tggagtggag ggcacagtcc gagtctgccc ggagcaagat gttgagcggc   1140
atcgggggct gcgtgcttgg ggtgatcttc ctcgggctcg ccttttcat ccgtcacagg   1200
agtcagaaag gacctcgagg ccctcctcca gcagggctcc tgcagtgact cagagtgttt   1260
tgactcagtt gactgtctca gactgtaaga cctacatgtc tcgaattcga gctcggtacc   1320
cggggatcct ctagagtcga cctgcaggca tgcaattcga tgcacactca cattcttctc   1380
ctaatacgat aataaaactt tccatgaaaa atatggaaaa atatatgaaa attgagaaat   1440
ccaaaaaact gataaacgct ctacttaatt aaaatagata aatgggagcg gcaggaatgg   1500
cggagcatgg ccaagttcct ccgccaatca gtcgtaaaac agaagtcgtg gaaagcggat   1560
agaaagaatg ttcgatttga cgggcaagca tgtctgctat gtggcggatt gcggaggaat   1620
tgcactggag accagcaagg ttctcatgac caagaatata gcggtgagtg agcgggaagc   1680
tcggtttctg tccagatcga actcaaaact agtccagcca gtcgctgtcg aaactaatta   1740
agtaaatgag ttttttcatgt tagtttcgcg ctgagcaaca attaagtttta tgtttcagtt   1800
cggcttagat ttcgctgaag gacttgccac tttcaatcaa tactttagaa caaaatcaaa   1860
actcattcta atagcttggt gttcatcttt tttttttaatg ataagcattt tgtcgtttat   1920
acttttttata tttcgatatt aaaccaccta tgaagttcat tttaatcgcc agataagcaa   1980
tatattgtgt aaatatttgt attctttatc aggaaattca gggagacggg gaagttacta   2040
tctactaaaa gccaaacaat ttcttacagt tttactctct ctactctaga gcttggcact   2100
ggccgtcgtt ttacaacgtc gtgactggga aaaccctggc gttacccaac ttaatcgcct   2160
tgcagcacat ccccctttcg ccagctggcg taatagcgaa gaggcccgca ccgatcgccc   2220
ttcccaacag ttgcgcagcc tgaatggcga atggcgcctg atgcggtatt ttctccttac   2280
gcatctgtgc ggtatttcac accgcatatg gtgcactctc agtacaatct gctctgatgc   2340
cgcatagtta agccagcccc gacacccgcc aacacccgct gacgcgccct gacgggcttg   2400
```

-continued

```
tctgctcccg gcatccgctt acagacaagc tgtgaccgtc tccgggagct gcatgtgtca    2460
gaggttttca ccgtcatcac cgaaacgcgc gagacgaaag ggcctcgtga tacgcctatt    2520
tttataggtt aatgtcatga taataatggt ttcttagacg tcaggtggca cttttcgggg    2580
aaatgtgcgc ggaacccta tttgtttatt tttctaaata cattcaaata tgtatccgct     2640
catgagacaa taaccctgat aaatgcttca ataatattga aaaggaaga gtatgagtat     2700 tcaacatttc cgtgtcgccc ttattccctt ttttgcggca ttttgccttc ctgttttgc     2760 tcacccagaa acgctggtga agtaaaaga tgctgaagat cagttgggtg cacgagtggg     2820
ttacatcgaa ctggatctca acagcggtaa gatccttgag agttttcgcc ccgaagaacg    2880
ttttccaatg atgagcactt ttaaagttct gctatgtggc gcggtattat cccgtattga    2940
cgccgggcaa gagcaactcg gtcgccgcat acactattct cagaatgact tggttgagta    3000
ctcaccagtc acagaaaagc atcttacgga tggcatgaca gtaagagaat tatgcagtgc    3060
tgccataacc atgagtgata acactgcggc caacttactt ctgacaacga tcggaggacc    3120
gaaggagcta accgcttttt tgcacaacat gggggatcat gtaactcgcc ttgatcgttg    3180
ggaaccggag ctgaatgaag ccataccaaa cgacgagcgt gacaccacga tgcctgtagc    3240
aatggcaaca acgttgcgca aactattaac tggcgaacta cttactctag cttcccggca    3300
acaattaata gactgatgg aggcggataa agttgcagga ccacttctgc gctcggccct     3360
tccggctggc tggtttattg ctgataaatc tggagccggt gagcgtgggt ctcgcggtat    3420
cattgcagca ctggggccag atggtaagcc ctcccgtatc gtagttatct acacgacggg    3480
gagtcaggca actatggatg aacgaaatag acagatcgct gagataggtg cctcactgat    3540
taagcattgg taactgtcag accaagttta ctcatatata ctttagattg atttaaaact    3600
tcatttttaa tttaaaagga tctaggtgaa gatcctttt gataatctca tgaccaaaat     3660
cccttaacgt gagttttcgt tccactgagc gtcagacccc gtagaaaaga tcaaaggatc    3720
ttcttgagat cctttttttc tgcgcgtaat ctgctgcttg caaacaaaaa aaccaccgct    3780
accagcggtg gtttgtttgc cggatcaaga gctaccaact cttttttcga aggtaactgg    3840
cttcagcaga gcgcagatac caaatactgt ccttctagtg tagccgtagt taggccacca    3900
cttcaagaac tctgtagcac cgcctacata cctcgctctg ctaatcctgt taccagtggc    3960
tgctgccagt ggcgataagt cgtgtcttac cgggttggac tcaagacgat agttaccgga    4020
taaggcgcag cggtcgggct gaacggggg ttcgtgcaca cagcccagct tggagcgaac     4080
gacctacacc gaactgagat acctacagcg tgagcattga aaagcgcca cgcttcccga     4140 agggagaaag gcggacaggt atccggtaag cggcagggtc ggaacaggag agcgcacgag    4200
ggagcttcca gggggaaacg cctggtatct ttatagtcct gtcgggtttc gccacctctg    4260
acttgagcgt cgatttttgt gatgctcgtc aggggggcgg agcctatgga aaaacgccag    4320
caacgcggcc ttttacggt tcctggcctt ttgctggcct tttgctcaca tgttctttcc     4380
tgcgttatcc cctgattctg tggataaccg tattaccgcc tttgagtgag ctgataccgc    4440
tcgccgcagc cgaacgaccg agcgcagcga gtcagtgagc gaggaagcgg aagagcgccc    4500
aatacgcaaa ccgcctctcc ccgcgcgttg gccgattcat taatgcagct ggcacgacag    4560
gtttcccgac tggaaagcgg gcagtgagcg caacgcaatt aatgtgagtt agctcactca    4620
ttaggcaccc caggctttac actttatgct tccggctcgt atgttgtgtg gaattgtgag    4680
cggataacaa tttcacacag gaaacagcta tgaccatgat tacg                    4724
```

<210> SEQ ID NO 9
<211> LENGTH: 23
<212> TYPE: DNA
<213> ORGANISM: Artificial Sequence
<220> FEATURE:
<223> OTHER INFORMATION: synthesized

<400> SEQUENCE: 9
ccaccatggc cattagtgga gtc                                              23

<210> SEQ ID NO 10
<211> LENGTH: 29
<212> TYPE: DNA
<213> ORGANISM: Artificial Sequence
<220> FEATURE:
<223> OTHER INFORMATION: synthesized

<400> SEQUENCE: 10
tttggatcct tacagaggcc ccctgcgtt                                        29

<210> SEQ ID NO 11
<211> LENGTH: 24
<212> TYPE: DNA
<213> ORGANISM: Artificial Sequence
<220> FEATURE:
<223> OTHER INFORMATION: synthesized

<400> SEQUENCE: 11
ccaccatggt gtgtctgagg ctcc                                             24

<210> SEQ ID NO 12
<211> LENGTH: 29
<212> TYPE: DNA
<213> ORGANISM: Artificial Sequence
<220> FEATURE:
<223> OTHER INFORMATION: synthesized

<400> SEQUENCE: 12
tttggatcct cagctcagga atcctcttg                                        29

<210> SEQ ID NO 13
<211> LENGTH: 28
<212> TYPE: DNA
<213> ORGANISM: Artificial Sequence
<220> FEATURE:
<223> OTHER INFORMATION: synthesized

<400> SEQUENCE: 13
ccaccatggt cctaaacaaa gctctgat                                         28

<210> SEQ ID NO 14
<211> LENGTH: 30
<212> TYPE: DNA
<213> ORGANISM: Artificial Sequence
<220> FEATURE:
<223> OTHER INFORMATION: synthesized

<400> SEQUENCE: 14
tttggatcct cacaagggcc cttggtgtct                                       30

<210> SEQ ID NO 15
<211> LENGTH: 26
<212> TYPE: DNA
<213> ORGANISM: Artificial Sequence
<220> FEATURE:
<223> OTHER INFORMATION: synthesized

```
<400> SEQUENCE: 15
ccaccatggc ttggaagaag gcctttt                                26

<210> SEQ ID NO 16
<211> LENGTH: 26
<212> TYPE: DNA
<213> ORGANISM: Artificial Sequence
<220> FEATURE:
<223> OTHER INFORMATION: synthesized

<400> SEQUENCE: 16
tttagatctc agtgcagaag cccttt                                 26

<210> SEQ ID NO 17
<211> LENGTH: 25
<212> TYPE: DNA
<213> ORGANISM: Artificial Sequence
<220> FEATURE:
<223> OTHER INFORMATION: synthesized

<400> SEQUENCE: 17
ccaccatggg ccctgaagac agaat                                  25

<210> SEQ ID NO 18
<211> LENGTH: 27
<212> TYPE: DNA
<213> ORGANISM: Artificial Sequence
<220> FEATURE:
<223> OTHER INFORMATION: synthesized

<400> SEQUENCE: 18
tttggatcct cacagggtcc cctgggc                                27

<210> SEQ ID NO 19
<211> LENGTH: 26
<212> TYPE: DNA
<213> ORGANISM: Artificial Sequence
<220> FEATURE:
<223> OTHER INFORMATION: synthesized

<400> SEQUENCE: 19
ccaccatggt tctgcaggtt tctgcg                                 26

<210> SEQ ID NO 20
<211> LENGTH: 29
<212> TYPE: DNA
<213> ORGANISM: Artificial Sequence
<220> FEATURE:
<223> OTHER INFORMATION: synthesized

<400> SEQUENCE: 20
tttggatcct tatgcagatc ctcgttgaa                              29

<210> SEQ ID NO 21
<211> LENGTH: 26
<212> TYPE: DNA
<213> ORGANISM: Artificial Sequence
<220> FEATURE:
<223> OTHER INFORMATION: synthesized

<400> SEQUENCE: 21
aagaattcac tagaggctag agccat                                 26

<210> SEQ ID NO 22
<211> LENGTH: 26
```

```
<212> TYPE: DNA
<213> ORGANISM: Artificial Sequence
<220> FEATURE:
<223> OTHER INFORMATION: synthesized

<400> SEQUENCE: 22
aaggatcctc acagggtgac ttgacc                                              26

<210> SEQ ID NO 23
<211> LENGTH: 2580
<212> TYPE: DNA
<213> ORGANISM: Artificial Sequence
<220> FEATURE:
<223> OTHER INFORMATION: engineered recombinant

<400> SEQUENCE: 23
gcgttgcagg acaggatgtg gtgcccgatg tgactagctc tttgctgcag gccgtcctat           60
cctctggttc cgataagaga cccagaactc cggcccccca ccgccaccg ccaccccat           120 acatatgtgg tacgcaagta agagtgcctg cgcatgcccc atgtgcccca ccaagagttt          180
tgcatcccat acaagtcccc aaagtggaga accgaaccaa ttcttcgcgg gcagaacaaa          240
agcttctgca cacgtctcca ctcgaatttg gagccggccg gcgtgtgcaa aagaggtgaa          300
tcgaacgaaa gacccgtgtg taaagccgcg tttccaaaat gtataaaacc gagagcatct          360
ggccaatgtg catcagttgt ggtcagcagc aaaatcaagt gaatcatctc agtgcaacta          420
aaggggggaa ttcgatctag aggctagagc catggatgac caacgcgacc tcatctctaa          480
ccatgagcaa ttgcccatac tgggcaaccg ccctagagag ccagaaaggt gcagccgtgg          540
agctctgtac accggtgttt ctgtcctggt ggctctgctc ttggctgggc aggccaccac          600
tgcttacttc ctgtaccagc aacagggccg cctagacaag ctgaccatca cctcccagaa          660
cctgcaactg gagagccttc gcatgaagct tccgaaatct gccaaacctg tgagccagat          720
gcggatggct actcccttgc tgatgcgtcc aatgtccatg gataacatgc tccttgggcc          780
tgtgaagaac gttaccaagt acggcaacat gacccaggac catgtgatgc atctgctcac          840
gaggtctgga cccctggagt acccgcagct gaaggggacc ttcccagaga atctgaagca          900
tcttaagaac tccatggatg gcgtgaactg gaagatcttc gagagctgga tgaagcagtg          960
gctcttgttt gagatgagca agaactccct ggaggagaag aagcccacag aggctccacc         1020
taaagagcca ctggacatgg aagacctatc ttctggcctg ggagtgacca gcaggaact          1080 gggtcaagtc accctgtgaa gacagaggcc agcatcaagc ttatcgatac cgtcgacctg         1140
caggcatgca attcgatgca cactcacatt cttctcctaa tacgataata aaacttttca         1200
tgaaaaatat ggaaaaatat atgaaaattg agaaatccaa aaaactgata acgctctac          1260 ttaattaaaa tagataaatg ggagcggcag gaatggcgga gcatggccaa gttcctccgc         1320
caatcagtcg taaaacagaa gtcgtggaaa gcggatagaa agaatgttcg atttgacggg         1380
caagcatgtc tgctatgtgg cggattgcgg aggaattgca ctggagacca gcaaggttct         1440
catgaccaag aatatagcgg tgagtgagcg ggaagctcgg tttctgtcca gatcgaactc         1500
aaaactagtc cagccagtcg ctgtcgaaac taattaagta aatgagtttt tcatgttagt         1560
ttcgcgctga gcaacaatta agtttatgtt tcagttcggc ttagatttcg ctgaaggact         1620
tgccactttc aatcaatact ttagaacaaa atcaaaactc attctaatag cttggtgttc         1680
atcttttttt ttaatgataa gcatttttgtc gtttatactt tttatatttc gatattaaac         1740
cacctatgaa gttcattttta atcgccagat aagcaatata ttgtgtaaat atttgtattc         1800
```

-continued

```
tttatcagga aattcaggga gacggggaag ttactatcta ctaaaagcca aacaatttct      1860 tacagttttta ctctctctac tctagagctt ggcactggcc gtcgttttac aacgtcgtga      1920
ctgggaaaac cctggcgtta cccaacttaa tcgccttgca gcacatcccc ctttcgccag      1980
ctggcgtaat agcgaagagg cccgcaccga tcgcccttcc caacagttgc gcagcctgaa      2040
tggcgaatgg cgcctgatgc ggtatttttct ccttacgcat ctgtgcggta tttcacaccg      2100
catatggtgc actctcagta caatctgctc tgatgccgca tagttaagcc agccccgaca      2160
cccgccaaca cccgctgacg cgccctgacg ggcttgtctg ctcccggcat ccgcttacag      2220
acaagctgtg accgtctccg ggagctgcat gtgtcagagg ttttcaccgt catcaccgaa      2280
acgcgcgaga cgaaagggcc tcgtgatacg cctatttttta taggttaatg tcatgataat      2340
aatggtttct tagacgtcag gtggcacttt tcggggaaat gtgcgcggaa ccccctatttg      2400 tttattttttc taaatacatt caaatatgta tccgctcatg agacaataac cctgataaat      2460
gcttcaataa tattgaaaaa ggaagagtat gagtattcaa catttccgtg tcgcccttat      2520
tccctttttt gcggcatttt gccttcctgt ttttgctcac ccagaaacgc tggtgaaagt      2580
```

```
<210> SEQ ID NO 24
<211> LENGTH: 32
<212> TYPE: DNA
<213> ORGANISM: Artificial Sequence
<220> FEATURE:
<223> OTHER INFORMATION: synthesized

<400> SEQUENCE: 24
aagaattcac catggatgat cagcgcgacc tt                                    32

<210> SEQ ID NO 25
<211> LENGTH: 31
<212> TYPE: DNA
<213> ORGANISM: Artificial Sequence
<220> FEATURE:
<223> OTHER INFORMATION: synthesized

<400> SEQUENCE: 25
aaaggatcct cacatgggga ctgggcccag a                                     31

<210> SEQ ID NO 26
<211> LENGTH: 25
<212> TYPE: DNA
<213> ORGANISM: Artificial Sequence
<220> FEATURE:
<223> OTHER INFORMATION: synthesized

<400> SEQUENCE: 26
aaaccatggg tcatgaacag aacca                                            25

<210> SEQ ID NO 27
<211> LENGTH: 27
<212> TYPE: DNA
<213> ORGANISM: Artificial Sequence
<220> FEATURE:
<223> OTHER INFORMATION: synthesized

<400> SEQUENCE: 27
tttgtcgact cagtcacctg agcaagg                                          27

<210> SEQ ID NO 28
<211> LENGTH: 22
<212> TYPE: DNA
<213> ORGANISM: Artificial Sequence
```

```
<220> FEATURE:
<223> OTHER INFORMATION: synthesized

<400> SEQUENCE: 28
aaaccatggt ctcattcctg cc                                              22

<210> SEQ ID NO 29
<211> LENGTH: 27
<212> TYPE: DNA
<213> ORGANISM: Artificial Sequence
<220> FEATURE:
<223> OTHER INFORMATION: synthesized

<400> SEQUENCE: 29
tttgtcgacc taggaaatgt gccatcc                                         27

<210> SEQ ID NO 30
<211> LENGTH: 34
<212> TYPE: DNA
<213> ORGANISM: Artificial Sequence
<220> FEATURE:
<223> OTHER INFORMATION: synthesized

<400> SEQUENCE: 30
tttagaattc accatggctt caacccgtgc caag                                 34

<210> SEQ ID NO 31
<211> LENGTH: 31
<212> TYPE: DNA
<213> ORGANISM: Artificial Sequence
<220> FEATURE:
<223> OTHER INFORMATION: synthesized

<400> SEQUENCE: 31
tttagtcgac tcagggaggt ggggcttgtc c                                    31

<210> SEQ ID NO 32
<211> LENGTH: 36
<212> TYPE: DNA
<213> ORGANISM: Artificial Sequence
<220> FEATURE:
<223> OTHER INFORMATION: synthesized

<400> SEQUENCE: 32
acccttgaat tcatggctcc cagcagcccc cggccc                               36

<210> SEQ ID NO 33
<211> LENGTH: 39
<212> TYPE: DNA
<213> ORGANISM: Artificial Sequence
<220> FEATURE:
<223> OTHER INFORMATION: synthesized

<400> SEQUENCE: 33
attaccggat cctcagggag gcgtggcttg tgtgttcgg                            39

<210> SEQ ID NO 34
<211> LENGTH: 27
<212> TYPE: DNA
<213> ORGANISM: Artificial Sequence
<220> FEATURE:
<223> OTHER INFORMATION: synthesized

<400> SEQUENCE: 34
aaggtacccg tggagactgc cagagat                                         27
```

<210> SEQ ID NO 35
<211> LENGTH: 27
<212> TYPE: DNA
<213> ORGANISM: Artificial Sequence
<220> FEATURE:
<223> OTHER INFORMATION: synthesized

<400> SEQUENCE: 35
tttggatccc tatggccgga aggcctg                                    27

<210> SEQ ID NO 36
<211> LENGTH: 27
<212> TYPE: DNA
<213> ORGANISM: Artificial Sequence
<220> FEATURE:
<223> OTHER INFORMATION: synthesized

<400> SEQUENCE: 36
aagaattcct gtcagaatgg ccaccat                                    27

<210> SEQ ID NO 37
<211> LENGTH: 28
<212> TYPE: DNA
<213> ORGANISM: Artificial Sequence
<220> FEATURE:
<223> OTHER INFORMATION: synthesized

<400> SEQUENCE: 37
tttagatctt cactcagctc tggacggt                                   28

<210> SEQ ID NO 38
<211> LENGTH: 36
<212> TYPE: DNA
<213> ORGANISM: Artificial Sequence
<220> FEATURE:
<223> OTHER INFORMATION: synthesized

<400> SEQUENCE: 38
acccttgagc tcatggttgc tgggagcgac gcgggg                          36

<210> SEQ ID NO 39
<211> LENGTH: 42
<212> TYPE: DNA
<213> ORGANISM: Artificial Sequence
<220> FEATURE:
<223> OTHER INFORMATION: synthesized

<400> SEQUENCE: 39
attaccggat ccttaaagaa cattcatata cagcacaata ca                   42

<210> SEQ ID NO 40
<211> LENGTH: 34
<212> TYPE: DNA
<213> ORGANISM: Artificial Sequence
<220> FEATURE:
<223> OTHER INFORMATION: synthesized

<400> SEQUENCE: 40
tttagaattc accatggctt gcaattgtca gttg                            34

<210> SEQ ID NO 41
<211> LENGTH: 31
<212> TYPE: DNA
<213> ORGANISM: Artificial Sequence
<220> FEATURE:
<223> OTHER INFORMATION: synthesized

```
<400> SEQUENCE: 41
tttagtcgac ctaaaggaag acggtctgtt c                              31

<210> SEQ ID NO 42
<211> LENGTH: 33
<212> TYPE: DNA
<213> ORGANISM: Artificial Sequence
<220> FEATURE:
<223> OTHER INFORMATION: synthesized

<400> SEQUENCE: 42
acccttgaat ccatgggcca cacacggagg cag                            33

<210> SEQ ID NO 43
<211> LENGTH: 39
<212> TYPE: DNA
<213> ORGANISM: Artificial Sequence
<220> FEATURE:
<223> OTHER INFORMATION: synthesized

<400> SEQUENCE: 43
attaccggat ccttatacag ggcgtacact ttcccttct                      39

<210> SEQ ID NO 44
<211> LENGTH: 36
<212> TYPE: DNA
<213> ORGANISM: Artificial Sequence
<220> FEATURE:
<223> OTHER INFORMATION: synthesized

<400> SEQUENCE: 44
tttagaattc accatggacc ccagatgcac catggg                         36

<210> SEQ ID NO 45
<211> LENGTH: 34
<212> TYPE: DNA
<213> ORGANISM: Artificial Sequence
<220> FEATURE:
<223> OTHER INFORMATION: synthesized

<400> SEQUENCE: 45
tttagtcgac tcactctgca tttggttttg ctga                           34

<210> SEQ ID NO 46
<211> LENGTH: 33
<212> TYPE: DNA
<213> ORGANISM: Artificial Sequence
<220> FEATURE:
<223> OTHER INFORMATION: synthesized

<400> SEQUENCE: 46
acccttgagc tcatggatcc ccagtgcact atg                            33

<210> SEQ ID NO 47
<211> LENGTH: 42
<212> TYPE: DNA
<213> ORGANISM: Artificial Sequence
<220> FEATURE:
<223> OTHER INFORMATION: synthesized

<400> SEQUENCE: 47 attaccccg ggttaaaaac atgtatcact tttgtcgcat ga                   42

<210> SEQ ID NO 48
```

```
<211> LENGTH: 31
<212> TYPE: DNA
<213> ORGANISM: Artificial Sequence
<220> FEATURE:
<223> OTHER INFORMATION: synthesized

<400> SEQUENCE: 48
aaaggatcca ccatgcagca gcccttcaat t                                    31

<210> SEQ ID NO 49
<211> LENGTH: 29
<212> TYPE: DNA
<213> ORGANISM: Artificial Sequence
<220> FEATURE:
<223> OTHER INFORMATION: synthesized

<400> SEQUENCE: 49
tttggatcct tagagcttat ataagccga                                       29

<210> SEQ ID NO 50
<211> LENGTH: 34
<212> TYPE: DNA
<213> ORGANISM: Artificial Sequence
<220> FEATURE:
<223> OTHER INFORMATION: synthesized

<400> SEQUENCE: 50
aaagaattcg gtaccatgcc ggaggagggt tcgg                                 34

<210> SEQ ID NO 51
<211> LENGTH: 29
<212> TYPE: DNA
<213> ORGANISM: Artificial Sequence
<220> FEATURE:
<223> OTHER INFORMATION: synthesized

<400> SEQUENCE: 51
tttggatcct cagggggcgca cccactgca                                      29

<210> SEQ ID NO 52
<211> LENGTH: 17
<212> TYPE: PRT
<213> ORGANISM: Homo sapiens

<400> SEQUENCE: 52

Ile Ser Gln Ala Val His Ala Ala His Ala Glu Ile Asn Glu Ala Gly
 1               5                  10                  15

Arg

<210> SEQ ID NO 53
<211> LENGTH: 13
<212> TYPE: PRT
<213> ORGANISM: Influenza

<400> SEQUENCE: 53

Pro Lys Tyr Val Lys Gln Asn Thr Leu Lys Leu Ala Thr
 1               5                  10

<210> SEQ ID NO 54
<211> LENGTH: 11
<212> TYPE: PRT
<213> ORGANISM: M. tuberculosis

<400> SEQUENCE: 54

Lys Thr Ile Ala Thr Asp Glu Glu Ala Arg Arg
```

```
                        1               5                   10

<210> SEQ ID NO 55
<211> LENGTH: 15
<212> TYPE: PRT
<213> ORGANISM: C. trachomatis

<400> SEQUENCE: 55

Gln Ala Ser Leu Ala Leu Ser Tyr Arg Leu Asn Met Phe Thr Pro
1               5                   10                  15

<210> SEQ ID NO 56
<211> LENGTH: 13
<212> TYPE: PRT
<213> ORGANISM: Homo sapiens

<400> SEQUENCE: 56

Phe Val Arg Phe Asp Ser Asp Ala Ala Ser Gln Arg Met
1               5                   10
```

MHC CLASS II ANTIGEN-PRESENTING SYSTEMS AND METHODS FOR ACTIVATIND CD4+T CELLS

CROSS-REFERENCE TO RELATED APPLICATIONS

This application is a divisional of U.S. application Ser. No. 09/194,285 filed Apr. 12, 1999 now U.S. Pat. No. 6,355,479, which is a rule 371 continuation of application Ser. No. PCT/US97/08697, filed May 22, 1997, which is a continuation-in-part application of U.S. provisional application Ser. No. 60/018,175 filed May 23, 1996 now abandoned.

TECHNICAL FIELD

The present invention relates to materials and methods of activating CD4+ T cells with specificity for particular antigenic peptides, the use of activated T cells in vivo for the treatment of a variety of disease conditions, and compositions appropriate for these uses.

BACKGROUND

Though the T cell repertoire is largely shaped during T cell development in the thymus, mature CD4+ T cells are also regulated extrathymically. Whereas, some conditions of activation lead to tolerance reflecting either anergy or clonal elimination, other conditions lead to a change in the type of response observed. For CD4+ T cells, this change in functional phenotype is largely a change in the pattern of cytokines produced. Although CD4+ T cells that are subject to acute activation maintain the ability to produce multiple cytokines, T cells obtained under conditions of chronic stimulation frequently demonstrate a more restricted pattern of cytokine production. For example, T cell clones maintained by repeated stimulation in vitro have defined two major functional categories of CD4+ T cells referred to as Th1 and Th2 type cells. Th1 type cells produce primarily interleukin-2 (IL-2), interferon-γ (IFN-γ) and tumor necrosis factor (TNF), all of which are referred to as inflammatory cytokines. In contrast, Th2 type cells typically produce IL-4, IL-5, and IL-10 and are important for antibody production and for regulating the responses of Th1 type cells.

Although such extreme segregation in cytokine production is often not seen during in vivo T cell responses, recovery from certain types of infections, such as *Leishmania*, is associated with preferential production of IL-2/IFN-γ. Mice that mount a Th2 response to *Leishmania* fail to contain the infection and ultimately die. Inappropriate production of cytokines of the Th2 type response has been frequently linked to allergic type diseases such as asthma and contact sensitivity. For review on activation of CD4+ T cells and role in allergic disease, see Hetzel and Lamb, *Clinical Immunol. Immunopath.*, 73:1–10 (1994).

Perhaps the strongest association of human disease with skewed patterns of cytokine production is the association of Th1 responses and Th1 type cytokines with autoimmune disease. Strong evidence in experimental models indicates that many types of autoimmunity including diabetes, experimental models for multiple sclerosis, autoimmune thyroiditis, and the like are mediated by Th1 type CD4+ T cells. The expression of Th2-associated cytokines, such as IL-4, in these models interfere with the development of autoimmune disease. Th2 type cytokines dampen the response of Th1 type cells while the Th1 type cytokines antagonize the development of Th2 type responses.

In view of the association of particular activated T cell subsets with particular disease conditions, a need therefore exists to be able to direct the proliferation and activation of CD4+T cells to a desired T cells subset, a process that is extremely beneficial in altering the course of disease. One potential solution is to activate in vitro CD4+ T cells that are first isolated from a subject who may optionally be having either allergy or autoimmune conditions to produce cells secreting a preferred cytokine profile. The resultant activated T cells are then reintroduced to the subject to alter the course of disease and perhaps even provide a long term cure.

The challenge in this approach, now solved by the present invention, is the difficulty in defining activation conditions that reproducibly generate CD4+ T cell subsets that produce the desired therapeutic cytokine profile. Expression of particular cytokines is linked to a particular antigen presenting cell (APC) and their associated accessory (assisting) molecules. For a review of the surface proteins serving as accessory molecules that are involved in T cell costimulation, see Mondino and Jenkins, *J. Leukocyte Biol.*, 55:805–815 (1994). Since both the cytokines produced by the APC and the coordinately expressed accessory molecules are themselves regulated by multiple factors, including the type of antigen, the affinity of the T cell receptor (TCR)-antigen interaction, antigen concentration and the like, predicting the outcome of T cell activation upon antigen presentation is historically very difficult. Indeed, as additional accessory molecules have been proposed for the activation process in vivo, it has become increasingly clear that many diverse molecules are involved in the regulation of T cell responses and act in combinatorial fashion to effect the outcome of T cell activation.

Prior to the present invention, the co-expression of selected MHC class II molecules in conjunction with one or more selected accessory molecules has not been possible. The present invention now presents a solution to predictably generate a preferred T cell phenotype through the reproducible activation of T cells to generate either Th1 or Th2 type T cells. The invention describes the generation of synthetic APC that present, in a neutral background, MHC class II molecules in combination with defined accessory molecules. The MHC class II molecules and defined accessory molecules are expressed in a nonmammalian insect cell and can be presented in a variety of forms of synthetic APC including insect cells displaying the molecules.

The advantage of using the insect cells as the expression and presentation vehicles for the MHC class II/accessory molecule compositions of this invention is that the cells do not endogenously produce regulatory cytokines and do not express mammalian accessory molecules. This overcomes the inherent unpredictability of using mammalian APC that express many molecules that are capable of altering the T cell response. In addition, the insect cell expression system described in the present invention provides for the expression of MHC class II molecules without bound peptide (i.e., "empty" molecules) that can be produced under certain restrictive circumstances, such as temperature requirements. At physiological temperatures, these "empty" molecules are normally unable to reach the cell surface as class II without bound peptide are very thermolabile. The invention utilizes the capacity of "empty" MHC class II compositions to allow for the exogenous loading of selected peptides along with the ability to provided endogenously loaded counterparts.

A recombinant glycosyl-phosphatidylinositol (GPI)-modified MHC class I molecule (HLA-A2.1:GPI/$\beta_2$m) was generated in the above-described insect cell system to produce antigen presenting cells as described in International Publication Number WO 96/12009 by Tykocinski. In that publication, the recombinant GPI-modified MHC class I molecules are isolated from the insect cell by affinity purification for subsequent reincorporation into cell membranes. In other aspects, the publication describes the preparation of a GPI-modified MHC class I molecule co-anchored on a cell membrane with a GPI-modified B7.1 costimulatory molecule. Although the publication states that GPI-modified MHC class II molecules can be prepared as described for those of MHC class I, the publication does not present any details for such preparation.

In contrast, the present invention provides and describes a unique means based on the co-expression of a selected MHC class II haplotype in conjunction with one or more accessory molecules, such as B7.1, to activate $CD4^+$ T cells resulting in the differentiation to a particular T cell subset, Th1 or Th2 cells, that effect a preferred cytokine profile influence. The invention provides the advantage of selectively activating $CD4^+$ T cells in vitro to a preferred T cell subset thereafter allowing for the reintroduction of the activated T cells into the patient. The present invention thus provides the ability to combine individual presenting molecules with particular accessory molecules for expression in selected combinations that permits reproducibility and predictability for selectively activating $CD4^+$ T cells to a desired T cell subset not available in other approaches.

BRIEF SUMMARY OF THE INVENTION

It has now been discovered that recombinant MHC class II molecules expressed in combination with selected accessory molecules, including costimulatory molecules and adhesion molecules, are effective in activating $CD4^+$ T cells to become armed effector T cells that recognize target cells on which MHC class II heterodimer is expressed for complexation with peptide.

Activation is characterized by proliferation and differentiation into effector T cell subsets, Th1 and Th2, that secrete particular cytokines. Th1 and Th2 type T cells are respectively referred to as inflammatory cells and T-helper cells.

Thus, the present invention relates to a synthetic antigen presenting system, also referred to as APC, for producing and presenting a mammalian, preferably human, MHC class II molecule in combination with one or more accessory molecules to activate $CD4^+$ T cells.

In one embodiment, the system relates to a synthetic antigen presenting matrix having a support and at least the extracellular portion of a MHC class II heterodimeric molecule operably linked to the support and capable of binding to a selected peptide. The matrix also includes an accessory molecule operably linked to the support. The accessory molecule interacts with a specific receptor present on the $CD4^+$ T cell. The MHC class II and accessory molecules are present in sufficient numbers to activate a population of $CD4^+$ T cells specific for the MHC class II/peptide combination when the peptide is bound to the extracellular portion of the MHC molecule.

It has been found that an antigen presenting matrix having both a MHC class II heterodimer or at least the extracellular portion thereof loaded with a peptide specific for that MHC, L together with an accessory molecule, provides a synergistic reaction in activating $CD4^+$ T cells. Examples of accessory molecules are costimulatory molecules, including B7.1 and B7.2, adhesion molecules such as intercellular cell adhesion molecule-1 (ICAM-1) and lymphocyte function-associated antigen-3 (LFA-3), and survival molecules such as Fas ligand (FasL) and CD70. In some embodiments, the extracellular portion of such accessory molecules can also be used in the present invention.

The support used for the matrix can take several different forms. Examples for the support include solid support such as metals or plastics, porous materials such as resin or modified cellulose columns, microbeads, microtiter plates, red blood cells and liposomes.

Another type of-support is a cell fragment, such as a cell membrane fragment. An entire cell is also contemplated as a support. In this embodiment, the matrix is actually cells which have been transformed with one or more expression vectors containing genes for the expression of MHC class II α- and β-chains along with at least one accessory molecule. The expressed proteins are then transported to the cell membrane where the transmembrane domain of the class II chains provide anchors allowing the extracellular domain to be displayed on the outer cell surface, thereby-creating a synthetic antigen presenting cell (APC). The expression vectors contain the selected genes, preferably in the form of a cDNA sequence, operably linked to a promoter that is either constitutive or inducible.

The MHC α- and β-chains associate together forming a MHC class II heterodimer which binds to a peptide specific for that heterodimer. With the present invention, two methods of loading peptides onto MHC class II heterodimers are contemplated. In one embodiment, the peptide is loaded intracellularly following proteolytic processing of internalized intact protein into peptide fragments. The peptides are then loaded onto newly generated MHC class II molecules while they are still within the cell. Alternatively, the MHC class II molecules are expressed as empty molecules on the cell surface and synthetic or processed peptide reagents are then loaded extracellularly onto the MHC class II heterodimer.

Nucleotide sequences for encoding at least one accessory molecule gene operably linked to a promoter in a vector are also introduced into the cell. Following expression, the accessory molecule is coordinately anchored on the surface of the cell along with the MHC class II heterodimer in sufficient numbers to activate a population of $CD4^+$ T cells lymphocytes specific for the MHC class II/peptide complex. Other molecules referred to as antigen processing assisting molecules are also contemplated for use in generating recombinant APC. These molecules are either provided by the cell used as APC or exogenously through an expression vector system as described above. Examples of such antigen processing assisting molecules include invariant chain, lysosomal enzymes and H2-M and H2-O molecules.

The cell line is synthetic in that at least one of the genes described above is not naturally present in the cells from which the cell line is derived. It is preferable to use a poikilotherm cell line because MHC molecules are thermolabile. A range of species are useful for this purpose. See, for example, U.S. Pat. No. 5,314,813 to Petersen et al. which discusses numerous species for this use, the disclosure of which is hereby incorporated by reference. Eukaryotic cells and preferably insect cells are used as APC. Preferred insect cells include *Drosophila* (fruit fly) and *Spodoptera* (butterfly).

MHC class II molecules have been expressed in insect cells such as *Drosophila* and *Spodoptera* cells. Since these cells do not have all the components of a mammalian immune system, the various proteins involved in the peptide loading machinery are absent from such cells. The lack of mammalian peptide-loading machinery allows the introduced mammalian MHC class II molecules to be expressed as empty molecules at the cell surface when the cells are cultured at thermostabile temperature restrictive conditions, such as at 28° C. In contrast, at 37° C., empty Class I molecules are thermolabile and tend to disintegrate. Thus, by incubating MHC class II-expressing *Drosophila* cells with peptides that specifically bind to anchored MHC class II molecule, virtually every class II molecule is loaded with one and the same peptide. Moreover, the invention provides for the means to introduce any known MHC class II α- and β-chain genes into an expression vector thereby overcoming the inherent limit to the number of MHC class II molecules expressed in any one mammal.

In the present invention, a specifically effective synergistic reaction in driving $CD4^+$ T cells to a Th1-type response characterized by an increase in the cytokine interleukin-2 (IL-2) results from a *Drosophila* antigen presenting cell having MHC class II molecules bound with a peptide, a costimulatory molecule, and an adhesion molecule. In particular, a highly effective synergistic generation of IL-2 production coupled with $CD4^+$ proliferation results from the combination of B7.2 and ICAM-1. In contrast, without ICAM-1 but with either B7.1 or B7.2, the *Drosophila* APC system loaded with peptide induced a Th2-type response characterized by an increase in IL-4. Thus, ICAM-1 antagonized the Th2-type response resulting in a Th1-type phenotype.

A Th1 phenotype characterized by IL-2 production coupled with proliferative responses also resulted from a synthetic antigen presenting cell having CD70 expressed simultaneously with ICAM-1 with or without B7.2.

Therefore, the selection of MHC class II genes in combination with at least one accessory molecule genes for expression thereof in an APC of this invention can be tailored depending upon the desired outcome for effecting proliferation and phenotypic activation of $CD4^+$ T cells.

The present invention also relates to methods for making the synthetic APC systems as described above in which at least one expression vector containing genes for a MHC class II heterodimer and an accessory molecule is introduced.

Methods of producing activated $CD4^+$ T cells in vitro are also contemplated. One preferred method comprises contacting, in vitro, $CD4^+$ cells with a synthetic MHC class II/accessory molecule-bearing APC described above for a time period sufficient to activate, in an antigen-specific manner, a population of $CD4^+$ T cells. The method may further comprise (1) separating the activated $CD4^+$ cells from the antigen-presenting matrix; (2) suspending the activated $CD4^+$ cells in an acceptable carrier or excipient; and (3) administering the suspension to an individual in need of treatment. As previously discussed, the antigens may comprise native or undegraded proteins or polypeptides, or they may comprise antigenic polypeptides which have been cleaved or synthesized into peptide fragments comprising at least 8 amino acid residues prior to incubation with the mammalian MHC class II heterodimeric molecules.

In addition to the utility of being able to direct the activation of $CD4^+$ T cells to a desired T cell subset as described above, the ability to express any MHC class II molecule provides the means to identify unknown $CD4^+$-activating peptide specific for that particular MHC class II molecule. As such, the present invention contemplates the activation of $CD4^+$ T cells through the screening of a peptide library with synthetic APC expressing a particular MHC class II heterodimer.

In a further embodiment, the synthetic APC system described herein is useful for isolation of reactive $CD4^+$ T cells from a heterologous population of cells. Such isolation provides the ability to monitor ongoing $CD4^+$ T cell-mediated responses in disease conditions in a patient.

In another variation of the above, in view of the ability to selectively activate $CD4^+$ T cells into a particular T cell subset for producing a preferred cytokine profile, the invention relates to methods of treating conditions in patients mediated by a undesirable $CD4^+$ response. Such disease conditions characterized by either a Th1- or Th2-type response include autoimmune diseases, allergy and cancer. The therapeutic goal is to introduce $CD4^+$ T cells activated to a preferred T cell subset to antagonize an ongoing $CD4^+$ T cell response. Thus, the method comprises (1) obtaining a fluid sample containing resting or naive $CD4^+$ cells from the patient; (2) contacting, in vitro, the $CD4^+$ cells with a selected synthetic peptide-loaded APC of this invention for a time period sufficient to activate, in an antigen-specific manner, the $CD4^+$ cells; and (3) administering the activated $CD4^+$ cells to the patient.

Other embodiments are apparent to one skilled in the art.

BRIEF DESCRIPTION OF THE DRAWINGS

In FIG. 1A, pRmHa-2 construction is shown; in FIG. 1B, pRmHa-3 construction is shown; and in FIG. 1C, the pRmHa-3 vector is illustrated, showing the restriction, polylinker, promoter, and polyadenylation sites, as well as a site at which a nucleotide sequence may be inserted for expression.

FIGS. 4A–4D show the cytokine profile produced in response to activation of $CD4^+$ T cells when cultured in the presence of *Drosophila* APC having recombinant MHC class II alone or in combination with B7.1 or B7.2 costimulatory molecules. Splenic APC (labeled T-S) are control assays. The assays are performed as described in Example 5. FIGS. 4A–4D respectively show the cytokines Il-2, Il-4, IFN-γ and Il-10 in ng/ml as plotted on the Y-axis. Cytokine profiles were assessed over three days between day 3 and 5 of culture.

FIGS. 5A–5D show the cytokine profile produced in response to activation of $CD4^+$ T cells when cultured in the presence of *Drosophila* APC having recombinant MHC class II alone or in combination with B7.2 costimulatory molecule, ICAM-1 and with B7.2 and ICAM-1. FIGS.

Figure 1A:
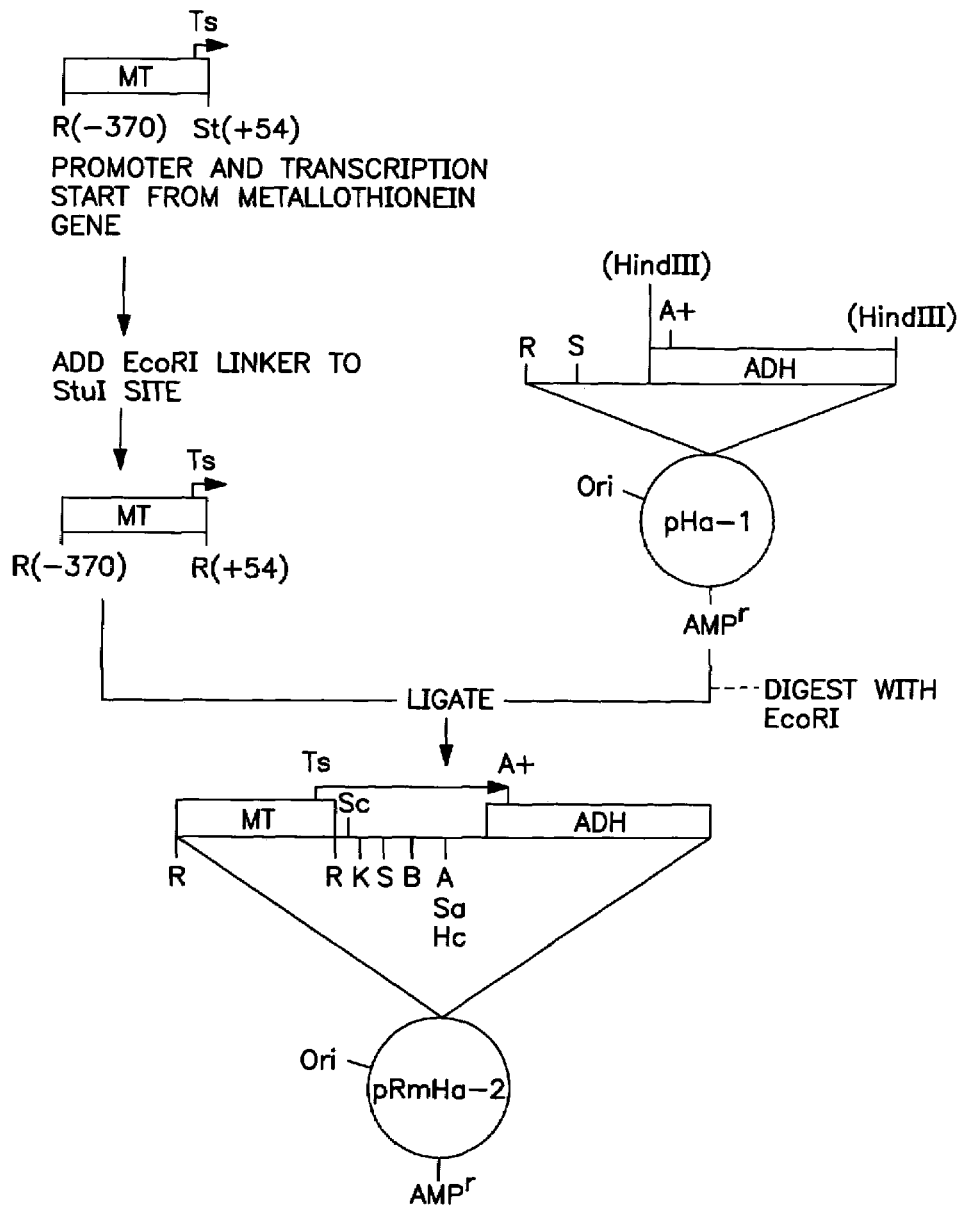
FIGS. 1A–1C diagram the construction of expression plasmids pRmHa-2 and pRmHa-3.

5A–5D respectively show the cytokines Il-2, Il-4, IFN-γ and Il-10 in ng/ml as plotted on the Y-axis. Refer to FIG. 4 legend for other details.

DETAILED DESCRIPTION OF THE INVENTION

A. Definitions

Amino Acid Residue: An amino acid formed upon chemical digestion (hydrolysis) of a polypeptide at its peptide linkages. The amino acid residues described herein are preferably in the "L" isomeric form. However, residues in the "D" isomeric form can be substituted for any L-amino acid residue, as long as the desired functional property is retained by the polypeptide. $NH_2$ refers to the free amino group present at the amino terminus of a polypeptide. COOH refers to the free carboxy group present at the carboxy terminus of a polypeptide. In keeping with standard polypeptide nomenclature (described in *J. Biol. Chem.*, 243:3552–3559 (1969) and adopted at 37 CFR §1.822(b)(2)), abbreviations for amino acid residues are shown in the following Table of Correspondence:

TABLE OF CORRESPONDENCE

| SYMBOL | | |
| --- | --- | --- |
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| Z | Glx | Glu and/or Gln |
| W | Trp | tryptophan |
| R | Arg | arginine |
| D | Asp | aspartic acid |
| N | Asn | asparagine |
| B | Asx | Asn and/or Asp |
| C | Cys | cysteine |
| X | Xaa | Unknown or other |

It should be noted that all amino acid residue sequences represented herein by formulae have a left- to-right orientation in the conventional direction of amino terminus to carboxy terminus. In addition, the phrase "amino acid residue" is broadly defined to include the amino acids listed in the Table of Correspondence and modified and unusual amino acids, such as those listed in 37 CFR 1.822(b)(4), and incorporated herein by reference. Furthermore, it should be noted that a dash at the beginning or end of an amino acid residue sequence indicates a peptide bond to a further sequence of one or more amino acid residues or a covalent bond to an amino-terminal group such as $NH_2$ or acetyl or to a carboxy-terminal group such as COOH.

Recombinant DNA (rDNA) molecule: A DNA molecule produced by operatively linking two DNA segments. Thus, a recombinant DNA molecule is a hybrid DNA molecule comprising at least two nucleotide sequences not normally found together in nature. rDNA's not having a common biological origin, i.e., evolutionarily different, are said to be "heterologous".

Vector: A rDNA molecule capable of autonomous replication in a cell and to which a DNA segment, e.g., gene or polynucleotide, can be operatively linked so as to bring about replication of the attached segment. Vectors capable of directing the expression of genes encoding for one or more polypeptides are referred to herein as "expression vectors".

Upstream: In the direction opposite to the direction of DNA transcription, and therefore going from 5' to 3' on the non-coding strand, or 3' to 5' on the mRNA.

Downstream: Further along a DNA sequence in the direction of sequence transcription or read out, that is traveling in a 3'- to 5'-direction along the non-coding strand of the DNA or 5'- to 3'-direction along the RNA transcript.

Reading Frame: A particular sequence of contiguous nucleotide triplets (codons) employed in translation that define the structural protein encoding-portion of a gene, or structural gene. The reading frame depends on the location of the translation initiation codon.

Polypeptide: A linear series of amino acid residues connected to one another by peptide bonds between the alpha-amino group and carboxy group of contiguous amino acid residues.

Protein: A linear series of greater than 50 amino acid residues connected one to the other as in a polypeptide.

Receptor: A receptor is a molecule, such as a protein, glycoprotein and the like, that can specifically (non-randomly) bind to another molecule.

Substantially Purified or Isolated: When used in the context of polypeptides or proteins, the terms describe those molecules that have been separated from components that naturally accompany them. Typically, a monomeric protein is substantially pure when at least about 60-os to 75% of a sample exhibits a single polypeptide backbone. Minor variants or chemical modifications typically share the same polypeptide sequence. A substantially purified protein will typically comprise over about 85% to 90% of a protein sample, more usually about 95%, and preferably will be over about 99% pure. Protein or polypeptide purity or homogeneity may be indicated by a number of means well known in the art, such as polyacrylamide gel electrophoresis of a sample, followed by visualization thereof by staining. For certain purposes, high resolution is needed and high performance liquid chromatography (HPLC) or a similar means for purification utilized.

Synthetic Peptide: A chemically produced chain of amino acid residues linked together by peptide bonds that is free of naturally occurring proteins and fragments thereof.

B. MHC Class II Heterodimers. Accessory Molecules and Antigen Processing Assisting Molecules The present invention relates to a synthetic antigen-presenting system for use in activating $CD4^+$ T cells. Though the T cell repertoire is largely shaped during T cell development in the thymus, mature $CD4^+$ T cells are also regulated extrathymically. Although some conditions of activation lead to tolerance reflecting either anergy or clonal elimination, other conditions lead to a change in the type of response observed. For $CD4^+$ T cells, this change in functional phenotype is largely a change in the pattern of cytokines produced. Although $CD4^+$ T cells that are subject to acute activation maintain the ability to produce multiple cytokines, T cells obtained under conditions of chronic stimulation frequently demonstrate a more restricted pattern of cytokine production. For example, T cell clones maintained by repeated stimulation in vitro have defined two major functional categories of CD4+ T cells referred to as Th1 and Th2 type cells. Th1 type cells produce primarily interleukin-2 (IL-2), interferon-γ (IFN-γ) and tumor necrosis factor (TNF), all of which are referred to as inflammatory cytokines. As such, the TH1 cells are sometimes referred to as inflammatory T cells which then activate macrophages to kill intravesicular pathogens they harbor as mediated by peptides generated from processing of pathogenic proteins presented to CD4+ T cells. In contrast, Th2 type cells typically produce IL-4, IL-5, and IL-10 and are important for antibody production and for regulating the responses of Th1 type cells. As such, Th2 cells are sometimes referred to as helper T cells that activate B cells to make antibody in response to peptides derived from extracellular pathogens and toxins that are presented to CD4+ T cells.

A CD4+ T cell is defined as a T cell or a T lymphocyte that has the CD4+ co-receptor on its cell surface in conjunction with the presence of either α:β or γ:Δ heterodimeric receptor associated with the proteins of the CD3 complex.

Activation of CD4+ T cell subsets is characterized by proliferation of the responsive T cell population coordinated with the selection production of cytokines as described above dependent upon the type of stimulation induced by an antigen presenting cell. The latter is defined as a highly specialized cell that can process antigens and display their peptide fragments on the cell surface together with molecules required for lymphocyte activation. The specificity of CD4+ T cell activation is based on the T cell antigen receptor (TCR) recognition of peptide antigens bound to MHC class II heterodimers on the surface of antigen presenting cells (APC) The main APC for T cells are dendritic cells, macrophages and B cells. In addition, APC-derived non-antigenic costimulatory signals play a contributory role in CD4+ T cell activation.

The present invention utilizes a synthetic antigen presenting system, based on the natural immunological response mechanisms described above, to manipulate the activation of CD4+ T cells by recombinant MHC class II molecules in conjunction with one or more accessory molecules broadly referred to as costimulatory molecules. The latter include specific costimulatory molecules, adhesion molecules and survival molecules, and the like. In other aspects of the invention, the synthetic antigen presenting system further contains antigen processing assisting molecules that are useful in generating peptide-loaded MHC class II molecules. In the context of this invention, the synthetic antigen presenting systems are useful for activating CD4+ T cells in vitro and in vivo. These aspects are discussed in Section E on Methods of Altering CD4+ T Cell Responses.

Thus, as mentioned above, the synthetic antigen presenting system of the present invention has at least two major components. The first component is at least the extracellular portions of a recombinant MHC class II heterodimer which is capable of binding to a peptide that provides the specificity of CD4+ T cell activation via recognition by the TCR. The second major component is at least the extracellular portion of at least one accessory molecule that provides a non-antigenic specific costimulatory signal in the activation of CD4+ T cells. In other embodiments, the entire molecules of the antigen presenting system and the non-antigen costimulatory signals are used.

For ease of description, MHC class II heterodimers will be discussed generally, with the understanding that an extracellular portion of the MHC molecule may be used in certain aspects of the invention. The portion of the MHC molecule necessary for the present invention is the part that binds to the antigenic peptide for presentation to the CD4+ T cells.

The present invention allows the recombinant MHC class II heterodimers to be produced by vector-transformed synthetic antigen presenting cells with the peptide already complexed with the MHC class II heterodimer. Alternatively, empty MHC class II heterodimers are produced that do not yet have a peptide complexed with them. This latter embodiment is particularly useful as it allows for complexation with a particular peptide or for screening of a library of peptides after the MHC class II heterodimers are expressed.

1. MHC Class II Genes and Encoded Heterodimers MHC class II molecules are cell surface glycoproteins that consist of a non-covalent complex of two chains, α and β, both of which span the membrane. A peptide-binding cleft is formed between the cooperating chains. Peptides that bind MHC class II molecules are variable in length and have anchor residues that lie at various distances from the ends of the peptides thereby resulting in peptides having ends that are not tightly bound within the cleft of the binding pocket. See, Janeway and Travers, *Immunobiology*, Section 4—4, Current Biology LTD, 2nd ed., 1996. Further aspects of the presenting antigenic peptides are discussed in Section D.

In vivo, empty MHC class II heterodimers become destabilized and are subsequently removed from the cell surface thereby preventing MHC molecules for acquiring peptides from the surrounding extracellular fluid that would deleteriously effect T cell specificity. In present invention, the synthetic antigen presenting cell system allows for the production of empty MHC class II heterodimers on the cell surface that are not subject to destabilizing events. As a consequence, loading of an antigenic peptide on a surface-expressed recombinant MHC class II heterodimer is facilitated for subsequent use in manipulating CD4+ activation and cytokine production.

The present invention, particular combinations of a selected MHC class II molecule with a coordinate antigen is facilitated by the presence of consensus nucleotide sequences in MHC class II genes. These regions, described further below, allow for the retrieval and use of the multiple MHC class II genes in the MHC complex in mammals as well as the multiple alleles of each gene. In other words, MHC is both polygenic and polymorphic having respectively several genes and multiple alleles of each gene.

In humans, MHC is called HLA while in mouse it is referred to as H-2. Three pairs of MHC class II α- and β-chain genes in humans have been designated HLA-DP, HLA-DQ and HLA-DR. The HLA-DR cluster contains an extra β-chain gene. As such, the three sets of genes can give rise to four types of MHC class II molecules. MHC class II genes and encoded α- and β-chains that are obtained from human genes are said to be of human origin. In mice, MHC class genes are designated H2-M, H2-A and H2-E. As each MHC class II molecule binds a different range of peptides, the presence of multiple gene loci gives an individual the ability to present a broad range of different peptides than if only one MHC class II molecules of each class were expressed at the cell surface.

While the polymorphic MHC class II genes encode corresponding proteins that vary by only one or a few amino acids, the different allelic variants differ by up to 20 amino acids. As a result, MHC class II diversity expands the ability of antigen recognition by T cells. Moreover, via MHC restriction, T cells have been shown to recognize peptide in the context of a particular MHC molecule but not when presented on another. Thus, T cell receptor specificity is imparted by both peptide and by the MHC molecule binding it.

The MHC class II heterodimers of this invention containing selected α- and β-chains are obtained by amplification of MHC class II-encoding genes and allelic variants thereof with specific pairs of oligonucleotide primers. The nucleotide sequences of the primers allow for amplification of the diversity of MHC class II genes and allelic variants thereof based on the 5' and 3' consensus nucleotide sequences present in the genes within a category of genes. Specific nucleotide sequences of primer pairs for amplifying the α- and β-chains of human HLA-DP, -DQ and -DR genes as well as those for amplifying murine $IA^d$-encoding heterodimers are presented in Example 2A.

The MHC class II-encoding genes are amplifiable from a variety of cellular sources including B cells, macrophages and dendritic cells, all of which are present in the blood. The amplification conditions for obtaining amplified MHC class II-encoding genes with the primers of this invention are described in Section C.

The α- and β-chains comprising the MHC heterodimers of this invention are useful in either anchored or soluble form. In the anchored form, the recombinant MHC heterodimer is anchored into the synthetic antigen presenting cell from which it is expressed. Alternatively, a recombinant MHC heterodimer is anchored in a matrix comprising a support as described in this invention after being secreted in soluble form. The latter is generated when a stop codon is engineered during the amplification procedure or thereafter into the nucleotide sequence encoding the MHC class II a- and U-chains of choice preceding the transmembrane domain.

2. Accessory Genes and Encoded Molecules

The accessory molecules of this invention, including costimulatory molecules, adhesion molecules and survival molecules, are effective in concert with the MHC class II heterodimer complexed with peptide in activating $CD4^+$ T cells to become armed effector T cells that recognize target cells. Naive T cells are activated to proliferate and differentiate into armed effector T cells when they encounter their specific antigen when presented by a peptide-loaded MHC class II heterodimer on the surface of an APC. Activation not only requires the recognition of a foreign peptide fragment bound to a MHC class II heterodimer but it also requires the simultaneous delivery of a costimulatory signal concurrently expressed by the APC.

Thus, the synthetic APC or matrices of this invention are characterized by the presence not only of a particular MHC class II heterodimer but also by the presence of one or more costimulatory molecules that are broadly defined as accessory molecules. At least three types of accessory molecules, including specific costimulatory molecules, adhesion molecules, and survival molecules, are contemplated for use in preparing synthetic APC or matrices of this invention a. Costimulatory Molecules A first type of an accessory molecule is composed of costimulatory molecules such as B7.1 (previously known as B7 and also known as CD80) and B7.2 (also known as CD86) which binds to CD28 on T cells. B7.1 and B7.2 are structurally related glycoproteins that are homodimeric members of the immunoglobulin superfamily. Other costimulatory molecules are anti-CD28 antibodies or the functional portions of such antibodies, e.g. Fab portions that bind to CD28. Ligation of CD28 by the above molecules has been shown to costimulate the growth of naive T cells. On activated T cells, an additional receptor, CTLA-4, binds B7 molecules with a higher affinity that that with CD28.

Recombinant B7 costimulatory molecules for use in the synthetic APC or matrices of this invention are obtained by PCR as described for MHC class II molecules. Preferred oligonucleotide primers and cellular sources for amplification therefrom as described in Example 2C.

b. Adhesion Molecules

Another major type of accessory molecule of the present invention is an adhesion molecule that also functions in T cell activation. Accesory adhesion molecules include the various ICAM molecules, which include intercellular adhesion molecule (ICAM) ICAM-1, ICAM-2, ICAM-3, lymphocyte function-associated antigen (LFA) LFA-1 and LFA-3. All of these molecules are members of the immunoglobulin superfamily. The ICAM-related members all bind to the T cell integrin, LFA-1. In addition to being expressed on APC including dendritic cells, macrophages and B cells, ICAM-1 and ICAM-2 are also expressed on endothelium, thereby mediating cell adhesion and subsequenct extravasation between circulating leukocytes and endothelium. ICAM-3, however, is only expressed on leukocytes and is thought to play an important part in adhesion between T cells and APC.

The interaction between ICAM-1, -2 and -3 synergizes with a second adhesive interaction between LFA-3 (CD58) and LFA-2 (CD2) that are respectively expressed on an APC and a T cell surface.

Recombinant adhesion molecules for use in the synthetic APC or matrices of this invention are obtained by PCR as described for MHC class II molecules. Preferred oligonucleotide primers and cellular sources for amplification therefrom as described in Example 2C.

c. Survival Molecules

A survival molecule is another type of an accessory molecule that plays a role in metabolic responses ranging from stimulatory to inducing cell death. Thus, a survival molecule can also be referred to as a cell death regulating molecule. A survival molecule is typically a protein but may include other types of macromolecules such as carbohydrates, lipids and the like. Survival molecules for use in the compositions and methods of this invention include Fas ligand, TNF-receptor, TNF, CD70, a Type II transmembrane protein that is a member of the TNF family that binds to CD27, a member of the TNF receptor family. Fas ligand binds to the receptor called Fas and receptor occupancy resulting in the induction of apoptotic cell death of the cell expressing Fas receptor. CD27 is expressed on resting T and B cells while CD70 is expressed on activated T and B cells. Binding of CD70 to its receptor, CD27, induces T-cell costimulation and the interaction may be important for the recruitment of T cells from the unprimed T cell pool. Under other certain conditions, activation of the TNF receptor by TNF results in a similar response.

The recombinant survival molecules described above for use in the synthetic APC or matrices of this invention are obtained by PCR as described for MHC class II molecules. Preferred oligonucleotide primers and cellular sources for amplification therefrom as described in Example 2C.

As shown in the Examples, particular combinations of a peptide bound to a recombinant MHC class II molecule used in conjunction with one or more of the above-described recombinant accessory molecules activates T cells into armed effector T cells that are distinguishable into Th1 inflammatory T cells and Th2 helper T cells.

3. Antigen Processing Assisting Genes and Encoded Molecules a. HLA-DM

HLA-DM in humans and H2-M in mice is a MHC class II-like molecule that is also encoded within the MHC class II gene clusters. HLA-DM, like MHC class II, contains both α- and β-chain genes forming a heterodimer. However, unlike MHC class II molecules, peptide loading is not required for stabilizing the molecule. HLA-DM facilitates the loading of peptides onto newly formed MHC class II heterodimers following the removal of the invariant chain as further described below. Recombinant HLA-DM is contemplated for use in the compositions and methods of this invention to assist in the loading of internally processed peptides.

b. Invariant Chain

The invariant chain is a specialized protein that binds to newly formed MHC class II heterodimers thereby forming a trimer with each subunit of the MHC class II heterodimer. The trimerized molecule prevents the loading of intracellular peptides present in the endoplasmic reticulum but it also facilitates the export of the molecule from that compartment. Thereafter, the invariant chain is cleaved through multiple steps resulting in a MHC class II heterodimer that can then be complexed with processed peptides.

Thus, recombinant invariant chain is contemplated for use in the compositions and methods of this invention to assist in the loading of internally processed peptides.

C. Nucleic Acids and Polynucleotides

1. PCR to Obtain Genes Encoding MHC Class II and Accessory Molecules

Nucleic acid sequences encoding MHC class II molecules, accessory molecules and antigen processing assisting molecules of this invention are obtained in a number of ways familiar to one of ordinary skill in the art including direct synthesis, cloning, purification of DNA from cells containing such genes, and the like. One expedient means to obtain genes for encoding the molecules used in the compositions and methods described herein is by polymerase chain reaction (PCR) amplification on selected nucleic acid templates with selected oligonucleotide primer pairs as further described below.

Known, partial and putative human leukocyte antigen (HLA), the genetic designation for the human MHC, amino acid and nucleotide sequences, including the consensus sequence, are published (see, e.g., Zemmour and Parham, *Immunogenetics* 33: 310–320 (1991)), and cell lines expressing HLA variants are known and generally available as well, many from the American Type Culture Collection ("ATCC"). Therefore, using PCR, MHC class II-encoding nucleotide sequences are readily operatively linked to an expression vector of this invention that is then used to transform an appropriate cell for expression therein.

Particularly preferred methods for producing the recombinant molecules of the present invention rely on the use of preselected oligonucleotides as primers in PCR to form PCR reaction products as described herein.

If a gene is to be obtained by PCR amplification, in general, two primers comprising a PCR primer pair, are used for each strand of nucleic acid to be amplified. For the sake of simplicity, synthesis of exemplary MHC class II heterodimer-encoding genes is discussed, but it is expressly to be understood that the PCR amplification method described is equally applicable to the synthesis of MHC class II allelic variants, accessory molecules and antigen processing assisting molecules, including those whose complete sequences are presently unknown.

In general, a first primer is referred to a forward primer or a 5' primer as it has the same sequence as the top strand of template DNA and thus hybridizes to the bottom complementary strand.

A second primer is referred to as a backward primer or a 3' primer as it has the same sequence as the bottom strand and thus hybridizes to the complementary sequence on the top strand. Typically, in other words, one primer is complementary to the negative (−) or bottom strand of the nucleotide sequence and the other is complementary to the positive (+) or top strand.

In preferred aspects, both first and second primers are chosen to hybridize to (i.e., be complementary to) conserved regions within the MHC class II genes. However, primers can be designed to amplify specific MHC class II genes and allelic variants thereof by hybridizing to unique rather than consensus sequences. For this aspect, the template sequence is preferably known for design of such primer pairs.

One or both of the first and second primers can be designed to introduce into the amplified product a nucleotide sequence defining an endonuclease recognition site. The site can be heterologous to the MHC class II gene being amplified and typically appears at or near the 5' end of the primer. It may also be helpful to place a 4-base spacer sequence proximal to the restriction site to improve the efficiency of cutting amplification products with enzymes.

The primers of the invention for isolating specific nucleotide sequences include oligonucleotides of sufficient length and appropriate sequence so as to provide specific initiation of polymerization on a significant number of nucleic acids with the corresponding nucleotide sequence. Specifically, the term oligonucleotide primer as used herein refers to a sequence comprising two or more deoxyribonucleotides or ribonucleotides, preferably more than three, and more preferably around 20, the sequence of which is capable of initiating synthesis of a primer extension product.

Experimental conditions conducive to synthesis include the presence of nucleoside triphosphates and an agent for polymerization and extension, such as thermostable polymerases, and a suitable buffer, temperature and pH. The primer is preferably single stranded for maximum efficiency in amplification, but may be double stranded. If double stranded, the primer is first treated to separate the two strands before being used to prepare extension products. Preferably, the primer is an oligodeoxyribonucleotide. The primer must be sufficiently long and substantially complementary to prime the synthesis of extension products in the presence of the inducing agent for polymerization and extension of the nucleotides. The exact length of primer will depend on many factors, including temperature, buffer, and nucleotide composition. The oligonucleotide primer typically contains 15–22 or more nucleotides, although it may contain fewer nucleotides. Alternatively, as is well known in the art, the mixture of nucleoside triphosphates can be biased to influence the formation of mutations to obtain a library of mutated recombinant MHC class II-encoding molecules for use in presenting unique peptides to CD4[+] T cells.

Oligonucleotide primers of the invention are employed in the PCR amplification process which is an enzymatic chain reaction that produces exponentially growing quantities of a nucleotide sequence. Annealing the primers to denatured nucleic acids followed by extension with a thermostable polymerase such as *Thermophilus aquaticus* (Taq) and *Pyrococcus furiosus* (Pfu) (Hoffman La-Roche, Basal, Switzerland), and nucleotides, results in newly synthesized (+) and (−) strands. Because these newly synthesized sequences are also templates, repeated cycles of denaturing, primer annealing, and extension results in exponential production of the DNA fragment defined by the primers. The product of the chain reaction is a discrete nucleic acid duplex with termini corresponding to the ends of the specific primers employed. Those of skill in the art will know of other amplification methodologies which can also be utilized to increase the copy number of target nucleic acids. These may include for example, ligation activated transcription (LAT), ligase chain reaction (LCR), and strand displacement activation (SDA), although PCR is the preferred method as described in the U.S. patents listed below.

The oligonucleotide primers of the invention may be prepared using any suitable method, such as conventional phosphotriester and phosphodiester methods as described above for synthesis of complementary oligonucleotides or automated embodiments thereof. One method for synthesizing oligonucleotides on a modified solid support is described in U.S. Pat. No. 4,458,066.

Preferred primers for amplifying MHC class II genes, accessory molecule genes, and antigen processing assisting molecule genes are described in Example 2.

PCR amplification methods are described in detail in U.S. Pat. Nos. 4,683,192, 4,683,202, 4,800,159, 4,965,188 and 5,395,750, the disclosures of which are hereby incorporated by reference, and at least in several texts including "PCR Technology: Principles and Applications for DNA Amplification", H. Erlich, ed., Stockton Press, New York (1989); and "PCR Protocols: A Guide to Methods and Applications", Innis et al., eds., Academic Press, San Diego, Calif. (1990). Various preferred methods and primers used herein are described hereinafter and are also described by Zemmour, et al., *Immunogenetics,* 33:310–20 (1991), by Ausebel, et al., In Current Protocols in Molecular Biology, Wiley and Sons, New York (1993) and by Sambrook et al., Molecular Cloning: A Laboratory Manual, Cold Spring Harbor Laboratory, (1989). Particular PCR methods including nested PCR, overlap PCR, reverse-transcriptase-PCR, and the like that are well known to one of ordinary skill in the art are contemplated for use in obtaining the recombinant molecules of this invention.

In alternative embodiments, the PCR process is used not only to produce a variety of MHC class II-encoding molecules, but also to induce mutations which may emulate those observed in the highly-polymorphic MHC loci, or to create diversity from a single parental clone and thereby provide a MHC class II-encoding DNA "library" having a greater heterogeneity.

2. Expression Vectors

The present invention contemplates plasmid expression vectors in substantially pure form capable of directing expression of MHC class II-encoding genes, accessory molecule genes and antigen processing assisting genes to produce the corresponding recombinant proteins. For simplicity, the above genes are herein referred to collectively as polypeptide-encoding nucleotide sequences. Vectors capable of directing the expression of genes to which they are operatively linked are referred to herein as "expression vectors" or "expression plasmids", both of which are also referred to as "plasmids".

As used herein, the term "vector" or "plasmid" refers to a nucleic acid molecule capable of transporting between different genetic environments another nucleic acid to which it has been operatively linked. Preferred vectors are those capable of autonomous replication and expression of structural gene products present in the DNA segments to which they are operatively linked. Vectors, therefore, preferably contain the replicons and selectable markers that are compatible with the host selection system. One type of preferred vector is an episome, i.e., a nucleic acid capable of extrachromosomal replication.

A plasmid of this invention is a circular double-stranded plasmid that contains at least a regulation region having elements capable of activating transcription of the translatable polypeptide-encoding nucleotide sequences of this invention. The plasmid further contains a translatable nucleotide sequence from which the desired encoded polypeptides of this invention are expressed. Thus, the vectors are said to be capable of directing the expression of the recombinant polypeptides described herein as encoded from the corresponding expressible genes.

A preferred vector for use according to the present invention is a plasmid; more preferably, it is a high copy number plasmid. It is also preferable that the vector of choice be best suited for expression in the chosen host.

Such expression vectors contain a promotor sequence in the regulatory region which facilitates the efficient transcription of an inserted genetic sequence in the host. Preferably, the vector contain an inducible promoter sequence, as inducible promoters tend to limit selection pressure against cells into which such vectors (which are often constructed to carry non-native or chimeric nucleotide sequences) have been introduced. The expression vector also typically contains an origin of replication as well as specific genes which allow phenotypic selection of the transformed cells. The DNA segment can be present in the vector operatively (also referred to as operably) linked to regulatory elements, for example, a promoter (e.g., T7, metallothionein I, or polyhedrin promoters).

In a separate embodiment, a plasmid also contains a gene, the expression of which confers a selective advantage, such as a drug resistance, to a host cell when introduced or transformed into that cell. Typical prokaryotic and eukaryotic drug resistance genes respectively confer resistance to ampicillin or tetracyclin and to neomycin (G418 or Geneticin). Other drug resistance markers include chloramphenicol, kanamycin, streptomycin, carbenicillin, mercury, rifampcin, rifampicin, fusaric acid, and the like.

The choice of vector to which the regulatory region and nucleotide sequences for encoding polypeptides of the present invention is operatively linked depends directly, as is well known in the art, on the functional properties desired, e.g., replication or protein expression, and the host cell to be transformed, these being limitations inherit in the art of constructing recombinant DNA molecules.

Operatively linking refers to the covalent joining of nucleotide sequences, preferably by conventional phosphodiester bonds, into one strand of DNA, whether in single or double stranded form. Moreover, the joining of nucleotide sequences results in the joining of functional elements such as response elements in regulatory regions with promoters and downstream polypeptide-encoding nucleotide sequences as described herein.

One typical method for operatively linking inserts into expression plasmids is by directional ligation. This is accomplished through a sequence of nucleotides that are adapted for directional ligation. Such a sequence is referred to commonly as a polylinker that is a region of the DNA expression vector that (1) operatively links for replication and transport the upstream and downstream translatable DNA sequences and (2) provides a site or means for directional ligation of a DNA sequence into the vector. Typically, a directional polylinker is a sequence of nucleotides that defines two or more restriction endonuclease recognition sequences, or restriction sites. Upon restriction cleavage, the two sites yield cohesive termini to which a translatable DNA sequence can be ligated to the DNA expression vector. Preferably, the two restriction sites provide, upon restriction cleavage, cohesive termini that are non-complementary and thereby permit directional insertion of a translatable DNA sequence into the cassette.

A variety of host-expression vector systems may be utilized to express a polypeptide encoded by a nucleotide sequence. These include but are not limited to microorganisms such as bacteria transformed with recombinant bacteriophage DNA, plasmid DNA or cosmid DNA expression vectors containing a polypeptide-encoding nucleotide sequence; yeast transformed with recombinant yeast expression vectors containing a polypeptide-encoding nucleotide sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing a polypeptide-encoding nucleotide sequence; insect cell systems infected with recombinant virus expression vectors (e.g., baculovirus) containing a polypeptide-encoding nucleotide sequence; or animal cell systems infected with recombinant virus expression vectors (e.g., retroviruses, adenovirus, vaccinia virus) containing a polypeptide-encoding nucleotide sequence, or transformed animal cell systems engineered for stable expression. In such cases where glycosylation may be important, expression systems that provide for translational and post-translational modifications may be used; e.g., mammalian, insect, yeast or plant expression systems.

Any of these systems are useful in practicing the methods of this invention. With any of the above expression systems, the selected host is then used for expression of at least one MHC class II heterodimer alone or in conjunction with at least one accessory molecule further with or without an antigen processing accessory molecule depending on the actual mechanism for loading peptides, i.e., internally or externally.

Depending on the host/vector system utilized, any of a number of suitable transcription and translation elements, including constitutive and inducible promoters, transcription enhancer elements, transcription terminators, etc. may be used in the expression vector (see e.g., Bitter, et al., *Methods in Enzymology*, 153:516–544, (1987)). For example, when cloning in bacterial systems, inducible promoters such as Pl of bacteriophage λ, Plac, PtrD, Ptac (Ptrp-lac hybrid promoter) and the like may be used. When cloning in mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5K promoter) may be used. Promoters produced by recombinant DNA or synthetic techniques may also be used to provide for transcription of a polypeptide-encoding nucleotide sequence.

In bacterial systems a number of expression vectors may be advantageously selected for expression of a polypeptide-encoding nucleotide sequence according to the methods of this invention. For example, when large quantities are to be produced, vectors which direct the expression of high levels of fusion protein products that are readily purified may be desirable. Those which are engineered to contain a cleavage site to aid in recovering the protein are preferred. Such vectors include but are not limited to the E. coli expression vector pUR278 (Ruther, et al., *EMBO J.*, 2:1791, (1983)), in which the polypeptide-encoding nucleotide sequence may be ligated into the vector in frame with the LacZ coding region so that a hybrid polypeptide-LacZ protein is produced; pIN vectors (Inouye & Inouye, *Nuc. Acids Res.*, 13:3101–3109, (1985); Van Heeke & Schuster, *J. Biol. Chem.*, 264:5503–5509, (1989)); and the like.

In one embodiment, the vector utilized includes prokaryotic sequences that facilitate the propagation of the vector in bacteria, i.e., a DNA sequence having the ability to direct autonomous replication and maintenance of the recombinant DNA molecule extra-chromosomally when introduced into a bacterial host cell. Such replicons are well known in the art.

Those vectors that include a prokaryotic replicon also typically include convenient restriction sites for insertion of a recombinant DNA molecule of the present invention. Typical of such vector plasmids are pUC8, pUC9, pBR322, and pBR329 available from BioRad Laboratories, (Richmond, Calif.) and pPL available from Pharmacia, (Piscataway, N.J.), and pBLUESCRIPT and pBS available from Stratagene, (La Jolla, Calif.). A vector of the present invention may also be a Lambda phage vector including those Lambda vectors described in *Molecular Cloning: A Laboratory Manual*, Second Edition, Maniatis et al., eds., Cold Spring Harbor, N.Y. (1989).

In another preferred embodiment, plasmid vectors for use in the present invention are also compatible with eukaryotic cells. Eukaryotic cell expression vectors are well known in the art and are available from several commercial sources. Typically, such vectors provide convenient restriction sites for insertion of the desired recombinant DNA molecule, and further contain promoters for expression of the encoded genes which are capable of expression in the eukaryotic cell, as discussed earlier. Typical of such vectors are pSVO and pKSV-10 (Pharmacia), and pPVV-1/PML2d (International Biotechnology, Inc.), and pTDT1 (ATCC, No. 31255).

In addition, in eukaryotic plasmids, one or more transcription units are present that are expressed only in eukaryotic cells. The eukaryotic transcription unit consists of noncoding sequences and sequences encoding selectable markers. The expression vectors of this invention also contain distinct sequence elements that are required for accurate and efficient polyadenylation. In addition, splicing signals for generating mature mRNA are included in the vector. The eukaryotic plasmid expression vectors can contain viral replicons, the presence of which provides for the increase in the level of expression of cloned genes. A preferred replication sequence is provided by the simian virus 40 or SV40 papovavirus.

A preferrred expression system for producing the recombinant molecules for use in this invention is an insect system. In one such system, *Autographa californica* nuclear polyhedrosis virus (AcNPV) is used as a vector to express foreign genes. The virus grows in *Spodoptera frugiperda* (Sf9) cells. The polypeptide-encoding nucleotide sequences of this invention may be cloned into non-essential regions (in *Spodoptera frugiperda* for example the polyhedrin gene) of the virus and placed under control of an AcNPV promoter (for example the polyhedrin promoter). Successful insertion of the polypeptide-encoding nucleotide sequence will result in inactivation of the polyhedrin gene and production of non-occluded recombinant virus (i.e., virus lacking the proteinaceous coat coded for by the polyhedrin gene). These recombinant viruses are then used to infect cells in which the inserted gene is expressed. See Smith, et al., *J. Biol. Chem.*, 46:584, (1983); Smith, U.S. Pat. No. 4,215,051.

In preferred embodiments, the host cell population is a *Drosophila* cell culture that requires a compatible vector including vectors functionally equivalent to those such as p25-lacZ (see Bello and Couble, *Nature*, 346:480 (1990)) or pRmHa-1, -2, or -3 (see Bunch, et al., *Nucl. Acids Res.* 16:1043–1061 (1988)). In the preferred embodiment, the vector is pRmHa-3, which is shown in FIG. 1C. This vector includes a metallothionein promoter, which is preferably upstream of the site at which the MHC sequence is inserted, and the polyadenylation site is preferably downstream of said MHC sequence. Insect cells and, in particular, *Drosophila* cells are preferred hosts according to the present invention. *Drosophila* cells such as Schneider-2 (S2) cells, as further described in Section D, have the necessary trans-acting factors required for the activation of the promoter and are thus even more preferred.

The expression vector pRmHa-3 is based on the bacterial plasmid pRmHa-1 (FIG. 1A), the latter of which is based on plasmid pUC18 and is deposited with the American Type Culture Collection (ATCC, Rockville, Md.), having the accession number 37253. The pRmHa-3 vector contains the promoter, the 5' untranslated leader sequence of the metallothionein gene with the Eco RI and Stu I sites removed as shown in FIG. 1C. It also contains the 3' portion of the *Drosophila* ADH gene including the polyadenylation site. Therefore, cloned DNA is transcriptionally regulated by the metallothionein promoter and polyadenylated. Construction of the pRmHa-1 plasmid is described in Bunch, et al., *Nucl. Acids Res.* 16: 1043–1061 (1988). Construction of the pRmHa-3 and pRmHa-2 plasmids (the latter of which has a metallothionein promoter sequence that may be removed as an Eco RI fragment) is described in the Examples. With regard to pRmHa-3, a preferred plasmid for use according to the present invention, Pst I, Sph I and Hind III are in the promoter fragment and therefore are not unique. Xba I is in the ADH fragment (4 bases from its 3' end) and is also not unique. The following restriction sites are, however, unique in pRmHa-3 to facilitate cloning of the recombinant genes of this invention: Eco RI, Sac I, Kpn I, Sma I, Bam HI, Sal I, Hinc 2, and Acc I.

Mammalian cell systems that utilize recombinant viruses or viral elements to direct expression may be engineered. For example, when using adenovirus expression vectors, the coding sequence of a polypeptide may be ligated to an adenovirus transcription/translation control complex, e.g., the late promoter and tripartite leader sequence. This chimeric gene may then be inserted into the adenovirus genome by in vitro or in vivo recombination. Insertion in a non-essential region of the viral genome (e.g., region E1 or E3) will result in a recombinant virus that is viable and capable of expressing the polypeptide in infected hosts (e.g., see Logan & Shenk, *Proc. Natl. Acad. Sci. USA*, 81:3655–3659, (1984)). Alternatively, the vaccinia virus 7.5K promoter may be used. (e.g., see, Mackett, et al., *Proc. Natl. Acad. Sci. USA*, 79:7415–7419, (1982); Mackett, et al., *J. Virol.*, 49:857–864, (1984); Panicali, et al., *Proc. Natl. Acad. Sci. USA*, 79:4927–4931, (1982)). Of particular interest are vectors based on bovine papilloma virus which have the ability to replicate as extrachromosomal elements (Sarver, et al., *Mol. Cell. Biol.*, 1:486, (1981)). Shortly after entry of this DNA into mouse cells, the plasmid replicates to about 100 to 200 copies per cell. Transcription of the inserted cDNA does not require integration of the plasmid into the host's chromosome, thereby yielding a high level of expression. These vectors can be used for stable expression by including a selectable marker in the plasmid, such as the neo gene. Alternatively, the retroviral genome can be modified for use as a vector capable of introducing and directing the expression of a polypeptide-encoding nucleotide sequence of this invention in host cells (Cone & Mulligan, *Proc. Natl. Acad. Sci. USA*, 81:6349–6353, (1984)). High level expression may also be achieved using inducible promoters, including, but not limited to, the metallothionine IIA promoter and heat shock promoters.

For long-term, high-yield production of recombinant proteins, stable expression is preferred. Rather than using expression vectors which contain viral origins of replication, host cells can be transformed with a cDNA controlled by appropriate expression control elements (e.g., promoter and enhancer sequences, transcription terminators, polyadenylation sites, etc.), and a selectable marker. As mentioned above, the selectable marker in the recombinant plasmid confers resistance to the selection and allows cells to stably integrate the plasmid into their chromosomes and grow to form foci which in turn can be cloned and expanded into cell lines.

For example, following the introduction of foreign DNA, engineered cells may be allowed to grow for 1–2 days in an enriched media, and then are switched to a selective media. A number of selection systems may be used, including but not limited to the herpes simplex virus thymidine kinase (Wigler, et al., *Cell*, 11:223, (1977)), hypoxanthine-guanine phosphoribosyltransferase (Szybalska & Szybalski, *Proc. Natl. Acad. Sci,. USA*, 48:2026, (1962)), and adenine phosphoribosyltransferase (Lowy, et al., *Cell*, 22:817, (1980)) genes, which can be employed in tk$^-$, hgprt$^-$ or aprt$^-$cells respectively. Also, antimetabolite resistance-conferring genes can be used as the basis of selection; for example, the genes for dhfr, which confers resistance to methotrexate (Wigler, et al., *Proc. Natl. Acad. Sci. USA*,77:3567, (1980); O'Hare, et al., *Proc. Natl. Acad. Sci. USA*, 78:1527, (1981)); gpt, which confers resistance to mycophenolic acid (Mulligan & Berg, *Proc. Natl. Acad. Sci. USA*, 78:2072, (1981)); neo, which confers, resistance to the aminoglycoside G-418 (Colberre-Garapin, et al., *J. Mol. Biol.*, 150:1, (1981)); and hygro, which confers resistance to hygromycin (Santerre, et al., *Gene*, 30:147, (1984)). Recently, additional selectable genes have been described, namely trpB, which allows cells to utilize indole in place of tryptophan; hisD, which allows cells to utilize histinol in place of histidine (Hartman & Mulligan, *Proc. Natl. Acad. Sci., USA*, 85:804, (1988)); and ODC (ornithine decarboxylase) which confers resistance to the ornithine decarboxylase inhibitor, 2-(difluoromethyl)-DL-ornithine, DFMO (McConlogue L., In: Current Communications in Molecular Biology, Cold Spring Harbor Laboratory ed., (1987).

Both prokaryotic and eukaryotic expression vectors are familiar to one of ordinary skill in the art of vector construction and are described by Ausebel, et al., In Current Protocols in Molecular Biology, Wiley and Sons, New York (1993) and by Sambrook et al., Molecular Cloning: A Laboratory Manual, Cold Spring Harbor Laboratory, (1989).

For producing recombinant MHC class II α- and β-chains, accessory molecules and antigen processing assisting molecules for use in the compositions and methods of this invention, the respective nucleotide regions are operatively inserted into an expression vector of this invention as described herein. As described in Section B, nucleic acids encoding the recombinant polypeptides of this invention are obtained in a number of ways one of which is by PCR amplification. One of the nucleotide segments to be operatively linked to vector sequences encodes at least a portion of MHC class II α- and β-chains. Preferably, the respective nucleotide sequences for encoding the complete α- and β-chains are separately inserted into an expression vector for expression therefrom; however, it is also feasible to construct a vector which also includes some non-coding MHC sequences as well. The sequences for encoding accessory molecules and antigen processing assisting molecules are similarly inserted into separate expression vectors.

Alternatively, the invention contemplates the presence of more than one polypeptide-encoding gene being present within the same vector, the expression of which is driven by separate regulatory elements, such as a promoter. In other words, the nucleic acids for encoding both α- and β-chains may be operatively ligated to the same expression vector with or without one or more nucleic acid sequences encoding accessory molecules. Thus, all possible combinations of expression vector construction for producing the recombinant proteins of this invention are contemplated.

In addition to the complete encoding nucleotide sequences as described above, soluble forms of the expressed recombinant polypeptides of this invention are contemplated. The soluble form differs from the non-soluble form in that it contains a "stop" codon inserted prior to the transmembrane domain or other functional location to generate soluble non-membrane anchorable proteins.

D. Synthetic Antigen Presenting Cells and Matrices for Peptide Presentation

1. Synthetic Antigen Presenting Cells and Matrices

In accordance with the present invention, the recombinant MHC class II heterodimers and at least one accessory molecule are operably linked to a matix comprising a support such that the MHC class II and accessory molecules are present in sufficient numbers to activate a population of CD4$^+$ T cells lymphocytes when presented with a peptide complexed to the extracellular portion of the MHC molecule. The peptide can be bound to the MHC class II heterodimer before or after it is linked to the support.

The support can take on many different forms. It can be a solid support such as a plastic or metal material, it can be a porous material such as commonly used in separation columns, it can be a liposome or red blood cell, or it can even be a cell or cell fragment. As discussed in more detail below, in the case where a cell serves as a support, the MHC class II and accessory molecules can be produced by the cell for presentation on that cell or for presentation on another support that can include a separate cell.

In the former situation, the MHC molecule is then linked to the cell by at least the transmembrane domain if not also the cytoplasmic domain which would not be present in a soluble form of MHC class II. In the latter situation, the extracellular portions of MHC class II molecule and accessory molecule can be linked to a support by providing an epitope which reacts to an antibody immobilized on the support. In addition, the MHC or assisting molecules can be produced with or linked to (His)$_6$ which would react with nickel in forming part of the support. Other means to immobilize or link MHC molecules to a support are well known in the art.

As discussed above, the support can be a cell membrane or an entire cell. In such a case, an eukaryotic cell line is modified to become a synthetic antigen presenting cell line for use in presenting peptide in the context of MHC class II to T cell lymphocytes. Because empty MHC molecules are thermolabile, it is preferred that the cell culture be poikilotherm and various cell lines are discussed in detail below.

A preferred cell line of the present invention is capable of continuous growth in culture and capable of expressing mammalian MHC class II molecules and accessory molecules on the cell surface. Any of a variety of transformed and non-transformed cells or cell lines are appropriate for this purpose, including bacterial, yeast, insect, and mammalian cell lines. (See, e.g., *Current Protocols in Molecular Biology*, John Wiley & Sons, NY (1991), for summaries and procedures for culturing and using a variety of cell lines, e.g., *E. coli* and *Sarcomyces cerevisiae*).

Preferably, the cell line is a eukaryotic cell line. More preferably, the cell line is poikilothermic (i.e., less sensitive to temperature challenge than mammalian cell lines). More preferably, it is an insect cell line. Various insect cell lines are available for use according to the present invention, including moth (ATCC CCL 80), armyworm (ATCC CRL 1711), mosquito larvae (ATCC lines CCL 125, CCL 126, CRL 1660, CRL 1591, CRL 6585, CRL 6586), silkworm (ATCC CRL 8851) and butterfly (*Spodoptera frugiperda* (Sf9 cells, ATCC CRL 1711). In a preferred embodiment, the cell line is a Drosophila cell line such as a Schneider cell line (see Schneider, *J. Embryol. Exp. Morph.*, 27:353–365 (1972)); preferably, the cell line is a Schneider 2 (S2) cell line (S2/M3) adapted for growth in M3 medium (see Lindquist, et al., *Drosophila Information Service*, 58:163 (1982)). Schneider 2 (S2) cells have been deposited pursuant to Budapest Treaty requirements with the American Type Culture Collection (ATCC), Rockville, Md., on Feb. 18, 1992, and was assigned accession number CRL 10974.

To generate a synthetic antigen presenting cell of this invention, one or more expression vectors for directing the expression of a selected MHC class II heterodimer in conjunction with one or more accessory molecules is introduced into a recipient host cell. In addition; in alternative embodiments, vectors for expressing antigen processing assisting molecules including HLA-DM and invariant chain are also introduced into the recipient cells. The genes for the above have been described in Sections B and C.

Thus, in order to prepare synthetic antigen presenting cells or matrices, the expression vectors for encoding recombinant polypeptides of this invention are transfected, i.e, introduced, into a selected host cell. The selection of expression vectors as well as the construction thereof is dependent upon the desired outcome for CD4$^+$ activation as previously discussed as reiterated below. Transfection, also referred to as transformation, may be accomplished via numerous methods, including the calcium phosphate method, the DEAE-dextran method, the stable transfer method, electroporation, or via the liposome mediation method. Numerous texts are available which set forth known transfection methods and other procedures for introducing nucleotides into cells; see, e.g., *Current Protocols in Molecular Biology*, John Wiley & Sons, NY (1991). Following introduction of one or more vectors, the recipient cell is said to be transformed, the selection of which can either be transient or stable.

A culture of cells is first established. A cell line is chosen for transfection because it lacks at least one of the genes being introduced. It has been found that insect cells are advantageous not only because they are poikilothermic, but because they lack these genes and the mechanisms which would otherwise produce MHC molecules bound to peptides. This allows for greater control over the production of peptide-bound MHC molecules, and the production of empty MHC molecules.

The selected cells are then transformed by the introduction of an expression vector containing an expressible MHC class II α-chain gene operably linked to a first promoter and an expressible MHC class II β-chain gene operably linked to a secong promoter. A first expressible accessory molecule gene operably linked to a third promoter in a vector is also introduced into the above cell. In a further embodiment, an expressible antigen processing assisting gene operably linked to a fourth promoter in a vector is introduced into the above cell.

In a more preferred embodiment, the vector comprises *Drosophila* expression plasmid pRmHa-3, described in Section C, into which expressible nucleotide sequences encoding the above recombinant proteins have been inserted using techniques disclosed herein. Preferably, the nucleotide sequences encoding the MHC class II chains, those encoding at least one accessory molecule and those encoding antigen processing assisting molecules are operably linked to separate expression plasmids that are individually cotransfected into the cultured cells. Alternatively, the nucleotide sequences may be operably linked to separate promoters in the same expression plasmid and cotransfected via that same plasmid. The MHC class II α- and α-chains are preferably from a different species, more preferably, a homeotherm such as mammals and, optimally, humans.

It is preferred that at least one of the genes and, in particular, the MHC class II chain genes be linked to an inducible promoter. This allows control over the production of MHC molecules so that they are only produced at a time when the peptide of interest is available either internally or externally and presented in the culture to react with the produced MHC molecules. This minimizes undesirable MHC molecule/peptide complexes.

Thus, the preferred cell line is a poikilotherm cell line that has separate vectors each containing a MHC class II α- and β-chain gene respectively operably linked to a first and second promoter. Preferably, the promoters are inducible to control the expression of the MHC class II chains. In addition, the cell contains a third vector containing at least a first expressible accessory molecule gene operably lined to a third promoter. In a further embodiment, the cell also contains a fourth vector containing an expressible antigen processing assisting gene operably linked to a fourth promoter. It is preferred that the cell assembles empty MHC molecules and presents them on the cell surface so that the peptides specific for a particular MHC class II haplotype or for a variant allele can be selected as desired.

The selection of compatible MHC class II α- and β-chain genes for use in conjunction with one or more particular accessory molecule-encoding genes is dependent upon the T cell activation profile desired. For example, as described in the Examples, recombinant B7.1 or B7.2 alone or together in conjunction with recombinant murine IA$^d$ MHC class II expressed on the surface of *Drosophila* APC resulted in proliferation of CD4$^+$ T cells having a Th2 profile of increased production of IL-4 and IL-10. In contrast, when either B7.1 or B7.2 were expressed on the surface of *Drosophila* APC with ICAM-1 along with the same MHC molecules, the activation of CD4$^+$ T cells resulted in a Th1 profile with increased IL-2 production and decreased IL-4 and IL-10 production.

Thus, the invention contemplates the production of synthetic APC having on the cell surface any combination of a MHC class II haplotype heterodimer with any one of the accessory molecules of this invention. Particularly preferred combinations include MHC class II with either a costimulatory molecule including B7.1 or B7.2, an adhesion molecule including ICAM-1, ICAM-2, ICAM-3 or LFA-3, or a survival molecule including Fas ligand (FasL). As described above, more than one of each category of accessory molecules can be co-expressed, as for example, B7.1 and B7.2. Alternative preferred embodiments include the permutations where two accessory molecules of different categories are co-expressed on the cell surface. In other words, an adhesion molecule with a costimulatory molecule, and adhesion molecule with a survival molecule, a costimulatory molecule with a survivial molecule. In a further embodiment, three accessory molecules of the different categories described herein are co-expressed on the APC surface. It is also contemplated that in all of these embodiments, more than one member of a particular category may be expressed in conjunction with more than one member of other categories. The particular selected combinations are effective on the surface of the cells from which they are expressed or when anchored on the surface of a matrix of this invention. The actual combinations prepared are selected on the basis of T cell activation outcome in view of the expressed MHC class II molecules complexed with antigenic peptide. Thus, depending on the complex of MHC class II/peptide, the T cell activation outcome may be distinct despite having the same expressed accessory molecules.

In a further embodiment, antigen processing assisting genes are co-transfected with any of the above-described combinations to provide for enhanced internal peptide processing and loading. This aspect thus does not involve the generation of empty MHC class II molecules on the cell surface for subsequent peptide complexation. Rather, the expression of invariant chain, HLA-DM or lysosomal enzymes is utilized to allow for optimal processing and loading of proteolytic peptide fragments following cell internalization. The APC of this invention thus can function in either motif of having the recombinant MHC class II heterodimers being loaded either intracellularly or extracellularly.

Successfully transformed cells, i.e., cells that contain at least one expression vector capable of directing the expression of nucleotide sequences according to the present invention, can be identified via well-known techniques. For example, cells resulting from the introduction of a cDNA or rDNA of the present invention can be cloned to produce individual colonies. Cells from those colonies can be harvested, lysed, and their DNA content examined for the presence of the rDNA using a method such as that described by Southern, *J. Mol. Biol.* 98: 503 (1975). In addition to directly assaying for the presence of rDNA, successful transformation or transfection may be confirmed by well-known immunological methods when the rDNA is capable of directing the expression of a subject MHC class II protein of accessory molecule. For example, cells successfully transformed with one or more expression vectors may produce proteins displaying particular antigenic properties which are easily determined using the appropriate antibodies, such as anti-class II of particular haplotypes. In addition, successful transformation/transfection may be ascertained via the use of an additional vector bearing a marker sequence, such as neomycin resistance, as described hereinabove.

It is also preferable that the culture be stable and capable of sustained growth at reduced temperatures. For example, it is preferred that the culture be maintained at about room temperature, e.g., about 24–27° C. In other embodiments, the culture is maintained at higher temperatures, particularly during the process of activating CD4$^+$ cells. It is thus preferred that a culture according to the present invention be capable of withstanding a temperature challenge of about 30° C. to about 37° C.

In order to prepare the culture for expression of empty or MHC class II molecules in conjunction with a least one accessory molecule of this invention and optionally antigen processing assisting molecules, the culture may first require stimulation, e.g., via CuSO$_4$ induction, for a predetermined period of time. After a suitable induction period, e.g., about 12–48 hours, peptides may be added at a predetermined concentration (e.g., about 0.2 µg/ml to 20 µg/ml). Proteins and peptides for both internal and external loading are prepared as discussed below. After a further incubation period, e.g., for about 12 hours at 27° C., the culture is ready for use in the activation of CD4$^+$ cells. While this additional incubation period may be shortened or perhaps omitted, the culture tends to become increasingly stable to temperature challenge if it is allowed to incubate for a time prior to addition of resting or naive CD4$^+$ cells. For example, cultures according to the present invention to which peptide has been added are capable of expressing significant amounts of peptide-loaded MHC class II molecules even when incubated for extended periods of time at 37° C.

Nutrient media useful in the culturing of transformed host cells are well known in the art and can be obtained from numerous commercial sources. In embodiments wherein the host cell is mammalian, a "serum-free" medium is preferably used.

The resulting recombinant expressed MHC class II molecules bind to a particular peptide and are present in sufficient numbers with at least one accessory molecule on the surface of the APC to activate a population of T cell lymphocytes against the MHC class II/peptide complex.

Where the cell line already produces one or more of the desired molecules, it is only necessary to transfect the culture with an expressible gene for the gene which is lacking in the cells. For example, if the cells already present the MHC molecules on their surface, it is only necessary to transfect the culture with a vector containing an expressible gene for the accessory molecule.

As previously discussed, a protein or peptide can be introduced into the cell culture at the time the cells are producing MHC class II molecules for internal processing. Through methods such as osmotic shock, the peptides can be introduced in the cell and bind to the produced MHC molecules. Alternatively, particularly in the case poikilotherm cell lines, the MHC molecules will be presented empty on the cell surface. The peptide can then be added to the culture and bound to the MHC molecules as desired. For simplicity, while one peptide is described herein, the methods of this invention contemplate the screening of peptide libraries for identifying novel antigenic peptides for use in the therapeutic methods of this invention.

After the cells are produced having a MHC class II heterodimer and at-least one accessory molecules on the cell surface, the cells can be lyophilized to generate cell fragments for use in activating a population of CD4$^+$ T cell lymphocytes.

Transfected cultures of cells are also used to produce extracellular portions of MHC class II molecules and accessory molecules. The use of extracellular portions in conjunction with supports such as solid supports has certain advantages of production. Where living cells are used to provide a synthetic antigen presenting cell, at least three genes, two to produce the MHC class II heterodimer and one for the accessory molecule must be introduced to the cell. Often, additional genes such as for antibiotic resistance are also transfected.

Where a solid support system is being used, one cell line is used to produce the extracellular portions of MHC class II molecules while another cell line is used to produce the extracellular portion of an accessory molecule. The MHC molecule portions and the accessory molecule portions are then harvested from their respective cultures. The molecules are then linked to an appropriate support in sufficient numbers to activate a population of T cells. From a production standpoint, two different cultures can be used, but it is also possible to use the same culture, however, requiring that the culture be transfected with the additional gene for expressing the extracellular portion of an accessory molecule.

A further modification of this embodiment is to provide a third culture of cells which is transfected with an expressible second accessory molecule gene. For example, the second culture of cells produces extracellular portions of the costimulatory molecule while the third culture of cells produce an extracellular portion of an adhesion molecule. The adhesion molecule portions are harvested and linked to the support. In preparing the extracellular portions of a MHC class II heterodimer to be linked to a support, soluble molecules are prepared as previously discussed. These molecules generally lack the transmembrane and cytoplasmic domain in the MHC molecule.

2. Peptides

Virtually all cellular proteins in addition to viral antigens are capable of being used to generate relevant peptide fragments that serve as potential MHC class II-specific peptides. The methods and compositions of this invention provide for MHC class II molecules that have an increased capacity to specifically activate CD4$^+$ cells.

The peptides of the present invention bind to MHC class II molecules. The binding occurs under biological conditions which can be created in vivo as well as in vitro. The exact nature of the binding of the peptides need not be known for practice of the invention.

Peptides that bind MHC class II molecules are variable in length and their anchor residues lie at various distances from the ends of the peptide. In one aspect, the peptides prepared for loading onto the MHC molecules are of a single species; i.e., that all peptides loaded onto the MHC be identical in size and sequence so as to produce monoantigenic peptide-loaded MHC class II molecules. In alternative embodiments, peptides are heterogenous and may comprise a random library of peptides to allow for selection of unique members that result in desired T cell activation profiles as previously described. The production and screening of random synthetic peptide libraries is familiar to one of ordinary skill in the art and is described in U.S. Pat. Nos. 5,556,762, 5,510, 240, 5,498,530, 5,432,018, 5,382,5.13, 5,338,665 and 5,270, 170, the disclosures of which are hereby incorporated by reference.

Peptides may be presented to the cells via various means. Preferably, peptides are presented in a manner which allows them to enter an intracellular pool of peptides. For example, peptides may be presented via osmotic loading. Typically, peptides are added to the culture medium. The peptides may be added to the culture in the form of an intact polypeptide or protein which is subsequently degraded via cellular processes, e.g., via enzymatic degradation. Alternatively, the intact polypeptide or protein may be degraded via some other means such as chemical digestion (e.g. cyanogen bromide) or proteases (e.g. chymotrypsin) prior to its addition to the cell culture. In other embodiments, the peptides are presented in smaller segments which may or may not comprise antigenic amino acid sequences in conjunction with a particular MHC class II haplotype.

Preferably, a sufficient amount of protein(s) or peptide(s) is added to the cell culture or synthetic matrix to allow the MHC class II molecules to bind and subsequently present a large density of the peptide. preferably, with the same kind of peptide attached to each MHC heterodimer, on the surface of the synthetic APC or matrices of this invention.

In another embodiment of the invention, peptides are added to transfected cells of the present invention in order to enhance the thermostability of the MHC molecules expressed by the cells. As noted above, peptides are preferably added to the culture medium. Antigenic peptides that bind to the MHC class II molecules serve to thermostabilize the MHC molecules and also increase the cell surface expression. Cultures with added peptides which bind to the MHC molecules are thus significantly less susceptible to temperature challenge than cultures without added peptide.

E. Methods of Altering CD4$^+$ T Cell Responses

1. Th1 and Th2 CD4$^+$ T Cell-Mediated Diseases

Inducing a naive T cell into a desired activated T cell type or deviating the effector function of an activated T cell from a Th1 type to a Th2 type and visa versa is one of the aims of the present invention, especially with regard to therapeutic methods in treating various CD4$^+$ T cell-mediated disease conditions.

The differentiation of a proliferating CD4$^+$ T cell into either an inflammatory T cell or a helper T cell is dependent on the cytokines produced by infectious agents, principally IL-12 and IL-4, the influence of accessory molecules and on the nature of the MHC class II/peptide complex. As previously discussed, cell-mediated immunity involves the destruction of intracellular pathogens by macrophages activated by Th1 inflammatory cells directed primarily to intracellular parasites including such parasites as *Mycobacterium, Leishmania, Pneumocystis* and the like. In contrast, humoral immunity depends on the production of antibody by B cells activated by helper T cells directed primarily at extracellular pathogens including *Clostridium, Staphylococcus, Streotococcus,* Polio virus, *Pneumocystis* and the like.

For example, recovery from certain types of infections, such as *Leishmania*, is associated with preferential production of IL-2/IFN-γ. Mice that mount a Th2 response to *Leishmania* fail to contain the infection and ultimately die. Inappropriate production of cytokines of the Th2 type response has been frequently linked to allergic type diseases such as asthma and contact sensitivity.

Perhaps the strongest association of human disease with skewed patterns of cytokine production is the association of Th1 responses and Th1 type cytokines with autoimmune disease. Strong evidence in experimental models indicates that many types of autoimmunity including diabetes, experimental models for multiple sclerosis, autoimmune thyroiditis, and the like are mediated by Th1 type CD4$^+$ T cells. The expression of Th2-associated cytokines, such as IL-4, in these models interfere with the development of autoimmune disease. Th2 type cytokines dampen the response of Th1 type cells while the Th1 type cytokines antagonize the development of Th2 type responses.

In view of the association of particular activated T cell subsets with particular disease conditions, a need therefore exists to be able to direct the proliferation and activation of CD4$^+$ T cells to a desired T cell subset, a process that is extremely beneficial in altering the course of disease. One potential solution is to activate in vitro CD4$^+$ T cells that are first isolated from a subject who may optionally be having either allergy or autoimmune conditions to produce cells secreting a preferred cytokine profile. The resultant activated T cells are then reintroduced to the subject to alter the course of disease and perhaps even provide a long term cure.

Alternative embodiments are directed at the ability to "vaccinate" a potentially responsive individual against the development of either a Th1 or Th2 response, whichever is applicable to that individual. In other words, the selective induction of a particular T cell subset may be achieved by inhibiting naive cells from developing toward the undersired phenotype. For example, in a potentially atopic individual, preventing a deleterious Th2 response would be beneficial as described by Hetzel and Lamb, *Clinical Immunol. Immunopath.*, 73:1–10 (1994).

In still a further embodiment, the compositions and methods of this invention are useful for actively stimulating the development of naive T cells toward the desired phenotype. Existing therapeutic models to date include the use of anti-cytokine antibodies are carrier proteins, the use of idiotype/GM-CSF fusion protein vaccines to prolong effects of exogenous cytokines, use of selected adjuvants, use of liposome-encapsulated allergens, use of peptide analogs and the like as reviewed by Hetzel and Lamb, id. The authors, however, do state that for chronic Th2 responses to allergens in vivo, little experimental data exists for the possibility of effecting a desired downregulation of the Th2 response.

In view of the foregoing, the compositions and methods of this invention provide a valuable means to accomplish the therapeutic interventions discussed above. The present invention allows one to define activation conditions that reproducibly generate CD4$^+$ T cell subsets that produce the desired therapeutic cytokine profile. Expression of particular cytokines is linked to a particular antigen presenting cell (APC) and their associated accessory molecules. Since both the cytokines produced by the APC and the coordinately expressed accessory molecules are themselves regulated by multiple factors, including the type of antigen, the affinity of the T cell receptor (TCR)-antigen interaction, antigen concentration and the like, predicting the outcome of T cell activation upon antigen presentation is historically very difficult. Indeed, as additional accessory molecules have been proposed for the activation process in vivo, it has become increasingly clear that many diverse molecules are involved in the regulation of T cell responses and act in combinatorial fashion to effect the outcome of T cell activation.

The present invention provides the generation of synthetic APC that present, in a neutral background, MHC class II molecules in combination with defined accessory molecules that are expressed preferably in a nonmammalian insect cell. The advantage of using the insect cells as the expression and presentation vehicles for the MHC class II/accessory molecule compositions of this invention is that the cells do not endogenously produce regulatory cytokines and do not express mammalian accessory molecules. This overcomes the inherent unpredictability of using mammalian APC that express many molecules that are capable of altering the T cell response. The present invention thus provides the ability to isolate individual presenting molecules and accessory molecules for expression in selected combinations that permits reproducibility and predictability not available in other approaches.

2. Therapeutic Methods

As discussed above, the present invention relates to a method for activating CD4$^+$ T cells into differentiated armed effector T cell subtypes. The method relates to providing a synthetic APC or matrix having anchored on the external surface a recombinant MHC class II heterodimer that is capable of binding a peptide. The compositions also have at least one accessory molecule presented on the cell surface. Naive or activated CD4$^+$ T cells can be obtained by removal from an individual to be treated. The antigen presenting cells are then contacted with the CD4$^+$ T cells for a sufficient period of time to activate the T cells into proliferating and differentiating into a desired T cell phenotype.

The activated CD4+ T-cells are separated from the cell line and put into a suspension in an acceptable carrier and administered to the individual.

It is preferred that human genes are used and, therefore, human molecule analogs are produced. As shown in prior U.S. Pat. No. 5,314,813, murine systems provide particularly useful models for testing the operation of T cell activation and demonstrate the applicability of the process for human systems. See also Sykulev et al., *Immunity*, 1:15–22 (1994).

a. Isolation of Resting or Activated CD4+ T Cells

Resting (or naive) as well as activated CD4+ cells that have not been activated to target a specific antigen presented in the context of MHC class II are extracted from an individual for incubation or exposure to the transformed cultures of the present invention. Naive cells can be distinguished from primer cells primarily based on the cell surface markers CD455RA and CD45.

It is also preferred that CD4+ cells are obtained from an individual prior to the initiation of other treatment or therapy which may interfere with the CD4+ cells' ability to be specifically activated. For example, if one is intending to treat an individual with an autoimmune disease, it is preferable to obtain a sample of cells and culture prior to the initiation of adjunctive therapy such as steriod treatment or during a window of time when the patient is not being treated at all.

When activating CD4+ T cells to alter the T cell-mediated immune response in a patient, the patient is first analyzed for a patient-specific profile to assess the T cell phenotypic disease state for instituting appropriate counter therapy involving production of the opposing T cell phenotype and cytokines. Cytokine profiles are established with anti-cytokine antibodies that are available from ATCC and by methods described in U.S. Pat. Nos. 5,405,751, 5,322,787 and 5,209, 920, the disclosures of which are hereby incorporated by reference. Preferred cytokine analyses include interleukin-2 (IL-2), interferon-γ (IFN-γ), tumor necrosis factor (TNF), interleukin-4 Ta (IL-4), interleukin-10 (IL-10) and the like. As previously discussed, particular cytokine profiles are associated with T cell phenotypes and disease states.

In particular, where the condition is an autoimmune disease including multiple sclerosis, autoimmune thyroiditis, systemic lupus erythromatosus, myasthenia gravis, Crohn's disease and inflammatory bowel disease, the cytokine profile is produced by a Th1 type response characterized by increased IL-2, IFN-γ and TNF. In contrast, where the condition is an allergy, such as asthma and contact sensitivity, the cytokine profile is produced by a Th2 type response characterized by increased IL-4 and IL-10.

After analyzing the patient cytokine profile and disease state, patient-isolated CD4+ T cells are contacted in vitro with the synthetic APC, cell fragments or matrices of this invention as described below in a sufficient amount for a sufficient time to induce the contacted cells to proliferate and differentiate into activated CD4+ T cells that produce a functionally opposing cytokine profile. That is, if the patient were characterized as being a Th1 type responder, the antigen to be presented to the patients CD4+ T cells would be that necessary to induce the cells to proliferate and differentiate into a Th2 type. The opposite treatment modality is performed if the patient is characterized with a Th2 type response. Thus, once the opposing activated cells are returned to the patient as described below, the therapeutic goal of effecting an alteration in T cell phenotype response is attained.

Methods of extracting and culturing lymphocytes are well known. For example, U.S. Pat. No. 4,690,915 to Rosenberg describes a method of obtaining large numbers of lymphocytes via lymphocytopheresis. Appropriate culturing conditions used are for mammalian cells, which are typically carried out at 37° C.

Various methods are also available for separating out and/or enriching cultures of CD4+ cells. Some examples of general methods for cell separation include indirect binding of cells to specifically-coated surfaces. In another example, human peripheral blood lymphocytes (PBL), which include CD4+ cells, are isolated by Ficoll-Hypaque gradient centrifugation (Pharmacia, Piscataway, N.J.). PBL lymphoblasts may be used immediately thereafter or may be stored in liquid nitrogen after freezing in FBS containing 10% DMSO (Sigma Chemical Co., St. Louis, Mo.), which conserves cell viability and lymphocyte functions.

Alternative methods of separating out and/or enriching cultures of precursor cells include both positive and negative selection procedures. For positive selection, after lymphocyte-enriched PBL populations are prepared from whole blood, subpopulations of CD4' lymphocytes are isolated therefrom by affinity-based separation techniques directed at the presence of the CD4 co-receptor antigen. These affinity-based techniques fluorescence-activated cell sorting (FACS), cell adhesion, magnetic bead separation and like methods. (See, e.g., Scher and Mage, in *Fundamental Immunology*, W. E. Paul, ed., pp. 767–780, River Press, NY (1984).) Affinity methods may utilize anti-CD4 co-receptor antibodies as the source of affinity reagent. Alternatively, the natural ligand, or ligand analogs, of CD4 receptor may be used as the affinity reagent. Various anti-T cell and anti-CD4 monoclonal antibodies for use in these methods are generally available from a variety of commercial sources, including the American Type Culture Collection (Rockville, Md.) and Pharmingen (San Diego, Calif.).

Negative selection procedures are utilized to effect the removal of non-CD4 from the CD4+ population. This technique results in the enrichment of CD4+ cells from the T and B cell population of leucophoresed patients. Depending upon the antigen designation, different antibodies may be appropriate. For example, monoclonal antibodies OKT4 (anti-CD4, ATCC No. CRL 8002) OKT 5 (ATCC Nos. CRL 8013 and 8016), OKT 8 (anti-CD8, ATCC No. CRL 8014), and OKT 9 (ATCC No. CRL 8021) are identified in the ATCC Catalogue of Cell Lines and Hybridomas (ATCC, Rockville, Md.) as being reactive with human T lymphocytes, human T cell subsets, and activated T cells, respectively. Various other antibodies are also available for identifying and isolating T cell species, including precursors and naive and activated memory mature peripheral T cells.

b. In Vitro Activation of CD4+ Cells

In order to optimize the in vitro conditions for the generation of specific CD4+ T cell phenotypes, the culture of antigen presenting cells is maintained in an appropriate medium. Preferably, when using a support of this invention that is an intact cell, the antigen-presenting cells are *Drosophila* cells, which are preferably maintained in serum-free medium (e.g. Excell 400). In alternative embodiments, however, when the support is a cell fragment or a matrix of an artificial support as previously described, the culture medium is selected to maintain the viability of the target cells.

Prior to incubation of the synthetic APC, cell fragments or matrices of this invention with the T cells to be activated, an amount of antigenic peptide is provided to the APC or matrices in sufficient quantity to become loaded onto the human MHC class II molecules for expression on the surface of the APC or matrices. As previously discussed, peptide loading can occur intracellularly or extracellularly. Both aspects are accordingly encompassed in the activation process described herein but for simplicity, loading of peptides is generically described as the details of peptide presentation to MHC class II heterodimers and loading have been previously discussed. Moreover, individual peptides as well as peptide libraries are contemplated for use in preparing activated CD4$^+$ T cells also as previously described. According to the present invention, a sufficient amount of peptide is an amount that will allow about 200 to about 500,000 and preferably about 200 to 1,000 or more, MHC class II molecules loaded with peptide to be expressed on the surface of each synthetic APC or matrix. Preferably, the above compositions are incubated with 0.2 μg/ml up to 20 μg/ml peptide.

The isolated CD4$^+$ cells are then incubated in culture with the appropriate peptide-loaded MHC class II heterodimers expressed on synthetic APCs or matrices for a time period sufficient to activate CD4$^+$ cells. Preferably, the CD4$^+$ cells shall thus be activated in an antigen-specific manner. The ratio of CD4$^+$ cells to antigen-presenting cells may vary from individual to individual and may further depend upon variables such as the amenability of an individual's lymphocytes to culturing conditions and the nature and severity of the disease condition or other condition for which the within-described treatment modality is used. Preferably, however, the lymphocyte:antigen-presenting cell or matrix ratio is preferably in the range of about 1:1 to 300:1.

The effector/antigen-presenting culture may be maintained for as long a time as is necessary to activate and enrich for a population of a therapeutically useable or effective number of CD4$^+$ cells. In general terms, the optimum time is between about one and five days, with a maximum specific level generally being observed after three to five days of culture. In one embodiment of the present invention, in vitro activation of CD4$^+$ cells is detected within a brief period of time after transfection of a cell line.

Preferably, the activation of CD4$^+$ cells is optimal within one week of exposure to antigen-presenting cells. Thereafter, in a preferred embodiment, the activated CD4$^+$ cells are further purified by isolation procedures including density gradients, resetting with antibody-red blood cell preparations, column chromatography and the like. Following the purification, the resulting CD4$^+$ cell preparation is further expanded by maintenance in culture for a period of time to obtain a population of $10^9$ activated CD4$^+$ cells. This period may vary depending on the replication time of the cells but may generally be 14 days.

c. Separation of CD4$^+$ Cells from Synthetic APC or Matrices

Activated CD4$^+$ cells may be effectively separated from the antigen presenting compositions of this invention using one of a variety of known methods. For example, monoclonal antibodies specific for the MHC class II heterodimers, for the peptides loaded thereon, or for the CD4$^+$ cells (or a segment thereof) may be utilized to bind their appropriate complementary ligand. Antibody-tagged cells may then be extracted from the stimulator-effector cell admixture via appropriate means such as via well-known flow cytometric or magnetic bead separation methods. Density gradients can also be used to separate blast cells.

d. Therapeutic Treatment with Activated CD4$^+$ Cells

Effective amounts of the activated CD4$^+$ cells can vary between in vitro and in vivo uses, as well as with the amount and type of target cells expressing the antigenic peptide used in activating the CD4+ population. The amount will also vary depending on the condition of the patient and should be determined via consideration of all appropriate factors by the practitioner. Preferably, however, about $1 \times 10^6$ to about $1 \times 10^{12}$, more preferably about $1 \times 10^8$ to about $1 \times 10^{11}$, and even more preferably, about $1 \times 10^9$ to about $1 \times 10^{10}$ activated CD4$^+$ cells are utilized for adult humans, compared to about $5 \times 10^{6-5 \times 10^7}$ cells used in mice.

Preferably, as discussed above, the activated CD4$^+$ cells are harvested from the synthetic APC or matrix in culture prior to administration of the CDr+ cells to the individual being treated. It is important to note, however, that unlike other present and proposed treatment modalities, in a preferred embodiment, the present method uses a cell culture system of *Drosophila* APC or acellular matrices that are not tumorigenic. Therefore, if complete separation of cells and activated CD4$^+$ cells is not achieved, there is no inherent danger known to be associated with the administration of a small number of synthetic APC or matrices, whereas administration of mammalian tumor-promoting cells may be extremely hazardous.

Methods of re-introducing cellular components are known in the art and include procedures such as those exemplified in U.S. Pat. No. 4,844,893 to Honsik, et al. and U.S. Pat. No. 4,690,915 to Rosenberg. For example, administration of activated CD4$^+$ cells via intravenous infusion is appropriate.

EXAMPLES

The following examples are intended to illustrate, but not limit, the present invention.

1. Preparation of pRmHa-3 Expression Vector

The pRmHa-3 expression vector for use in expressing MHC proteins in *Drosophila Schneider* 2 (S2) cells as described in this invention was constructed by ligating a Sph I-linearized pRmHa-1 DNA expression vector with a DNA fragment resulting from a Sph I restriction digest of a pRmHa-2 expression vector to form the pRmHa-3 expression vector as described below. The ligating of the linearized pRmHa-1 with the pRmHa-2 fragment in this manner was performed to remove one of two Eco RI restriction endonuclease cloning sites present in pRmHa-1. Thus, the resultant pRmHa-3 expression vector contained only one Eco RI restriction site in the multiple cloning site (polylinker) into which various MHC class II-encoding DNA fragments were inserted as described in the Examples.

A. Preparation of pRmHa-1 Expression Vector

The pRmHa-1 expression vector, containing a metallothionein promoter, metal response consensus sequences (designated MT) and an alcohol dehydrogenase (ADH) gene containing a polyadenylation signal isolated from *Drosophila melanogaster*, was constructed as described by Bunch et al., *Nucl. Acids Res.*, 16:1043–61 (1988). The plasmid expression vector, pUC18, having the ATCC accession number 37253, was used as the source vector from which subsequent vectors described herein were derived. The pUC18 plasmid contains the following restriction sites from 5' to 3' in the multiple cloning site, all of which are not illustrated in the schematic representations of the pUC18-derived vectors in FIG. 1: Eco RI; Sac I; Kpn I; Sma I and Sma I located at the same position; Bam H1; Xba I; Sal I, Acc I and Hinc II located at the same position; Pst I; Sph I and Hind III. The pUC18 vector was first digested with Hind III to form a linearized pUC18. Blunt ends were then created by filling in the Hind III ends with DNA polymerase I large fragment as described by Maniatis et al., *Molecular Cloning: A Laboratory Manual*, eds. Cold Spring Harbor Laboratory, New York (1982).

The resultant linearized blunt-ended pUC18 vector was ligated with a 740 base pair (bp) Hinf I fragment from the *Drosophila melanogaster* ADH gene containing a polyadenylation signal. The ligated ADH allele was first isolated from the plasmid pSACI, described by Goldberg et al., *Proc. Natl. Acad. Sci. USA*, 77:5794–5798 (1980), by digestion with Hinf I followed by blunt ending with Klenow resulting in the nucleotide sequence listed in SEQ ID NO 1. The pSACI vector containing the ADH allele was constructed by subcloning into pBR322 (ATCC accession number 31344) a 4.7 kilobase (kb) Eco RI fragment of *Drosophila* DNA selected from a bacteriophage lambda library containing random, high molecular weight (greater than 15 kb).

The 5' Hinf I restriction site occurred naturally in the ADH gene at position 1770 as described by Kreitman, *Nature*, 304:412–417 (1983). The 3' Hinf I site was derived from the pUC18 vector into which the ADH gene had been cloned. This position was four bases 3' to the Xba I site at position 2500 of the ADH gene. The ADH segment extended from 35 bp upstream of the polyadenylation/cleavage sequence in the 3' untranslated portion of the ADH mRNA to 700 bp downstream of the polyadenylation signal. The resultant pUC18-derived vector containing the ADH gene fragment was designated pHa-1 as shown in FIG. 1A.

A 421 bp Eco RI/Stu I MT gene fragment for insertion into pHa-1 was obtained from a clone containing DNA of approximately 15.3 kb in a *Drosophila melanogaster* genomic DNA library. The library, prepared with a Mbo I partial digestion of imaginal DNA, was cloned in the lambda derivative EMBL4. The 421 bp fragment contained the MT promoter and metal response consensus elements of the *Drosophila* MT gene (Maroni et al., *Genetics*, 112:493–504 (1986)). This region, containing the promoter and transcription start site at nucleotide position +1, corresponded to position −370 to nucleotide position +54 of the MT gene (SEQ ID NO 2). The resultant fragment was then ligated into pHa-1 I-" expression vector prepared above that was previously linearized with Eco RI and Sma I. The 3' blunt end in MT created by the Stu I digest was compatible with the blunt end in pHa-1 created by the Sma I digest. The resultant pUC18-derived vector containing a 5' *Drosophila* MT gene fragment and a 3' ADH gene fragment was designated pRmHa-1. The pRmHa-1 expression vector contained the origin of replication (ori) and the beta-lactamase gene conferring resistance to ampicillin (AMp$^r$) from pUC18 as shown in FIG. 1A on the pHa-1 vector. The pRmHa-1 also contained from 5' to 3' the MT gene fragment, the multiple cloning site and the ADH gene fragment. The pRmHa-1 vector was used as described below in the construction of the pRmHa-3 expression vector.

B. Preparation of pRmHa-2 Expression Vector

For constructing the pRmHa-2 expression vector shown in FIG. 1A, the MT fragment prepared above was inserted into the pUC18-derived vector pHa-1 as described for constructing pRmHa-1 above with a few modifications. An Eco RI linker was added to the Stu I site of the Eco RI/Stu I-isolated MT gene fragment prepared above to form a metallothionein fragment having Eco RI restriction sites on both ends. The resultant fragment was then ligated into the ADH fragment-containing pUC18 expression vector that was previously linearized with Eco RI. The resultant pUC18-derived vector containing a 5' *Drosophila* MT gene fragment and a 3' ADH gene fragment having two Eco RI restriction sites 5' to the multiple cloning site was designated pRmHa-2. The pRmHa-2 expression vector contained the origin of replication (ori) and the beta-lactamase gene conferring resistance to ampicillin (Amp$^r$) from pUC18. The diagram of pRmHa-2 also shows the 5' to 3' contiguous positions of the MT gene fragment, the multiple cloning site and the ADH gene fragment. The pRmHa-2 vector was used along with pRmHa-1 as described below in the construction of the pRmHa-3 expression vector.

C. Preparation of pRmHa-3 Expression Vector

Figure 1B:
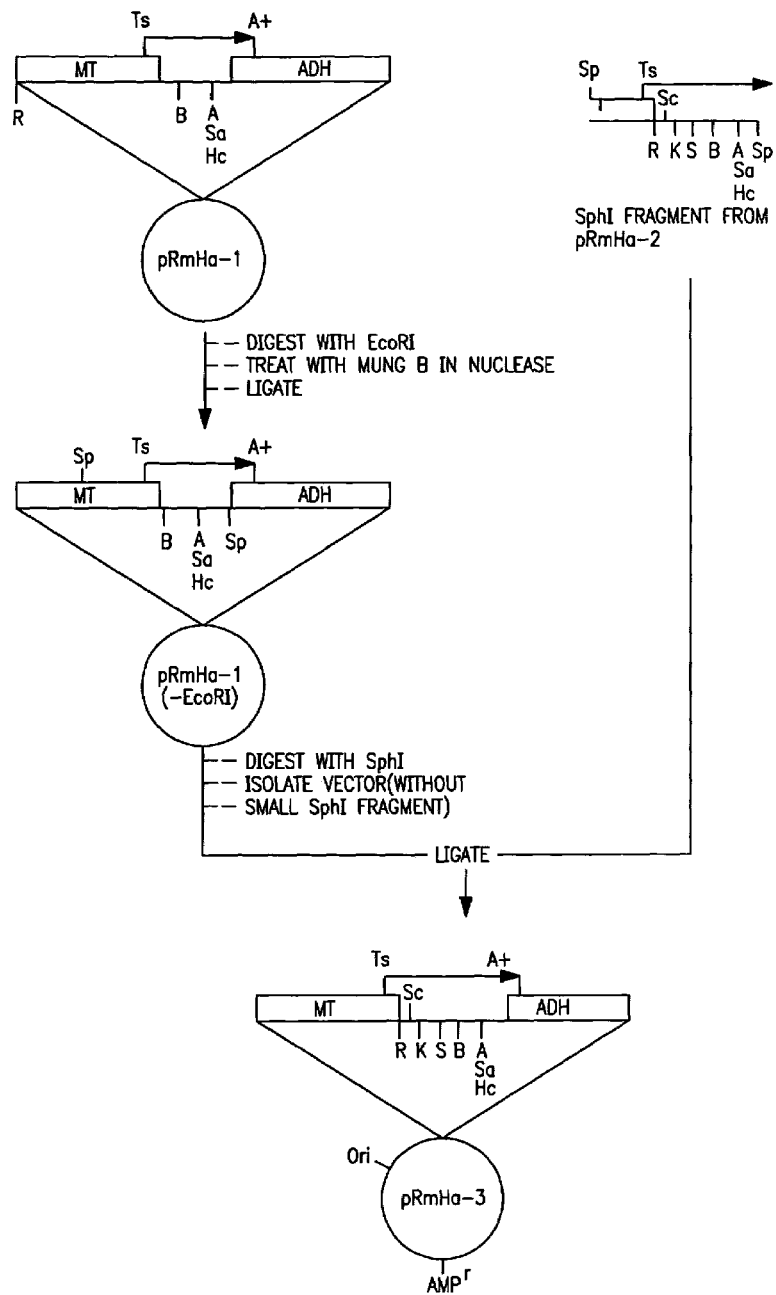
Figure 1C:
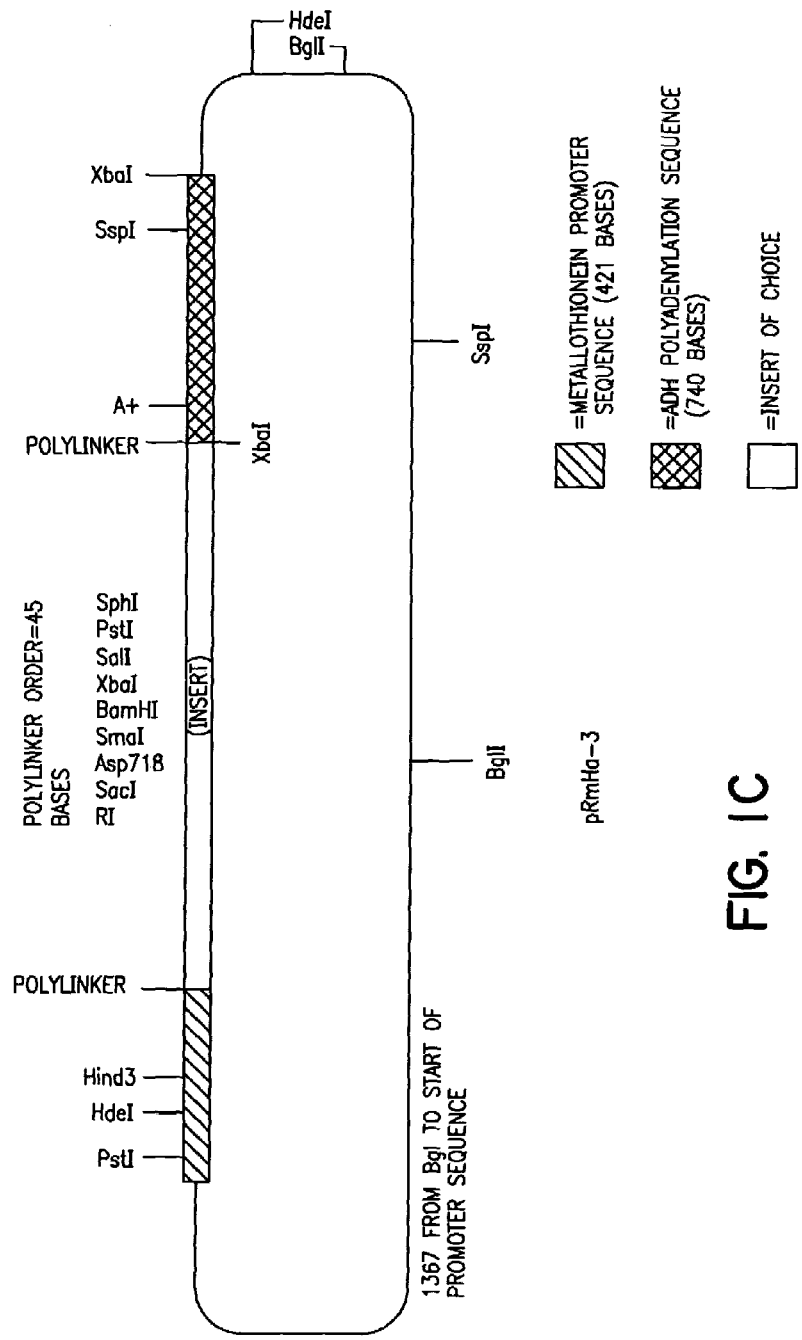

To prepare the pRmHa-3 expression vector that had only one Eco RI restriction site, a fragment from pRmHa-2 was ligated into pRmHa-1. For this construction, pRmHa-2, prepared above, was first digested with Sph I. The resultant Sph I fragment beginning in the middle of the MT gene and extending to the Sph I site in the multiple cloning site was first isolated from the pRmHa-2 vector and then ligated into pRmHa-1 that was previously modified to remove the Eco RI restriction site 5' to the MT gene fragment then linearized with Sph I. This process is schematically illustrated in FIG. 1B. To remove the Eco RI site in pRmHa-1, the vector was first digested with Eco RI to form a linearized vector, then blunt ended with Mung Bean nuclease and religated.

A schematic of the pRmHa-3 vector is shown in FIG. 1C. The relative positions of the various restriction sites from the pUC18 vector from which pRmHa-3 was derived are indicated in the figure. The pRmHa-3 vector, being derived from pUC18, contains the pUC18 origin of replication and beta-lactamase gene conferring ampicillin resistance. Thus, MHC class II-encoding DNA fragments as prepared in this invention and cloned into the multiple cloning site of pRmHa-3 were transcriptionally regulated by the MT promoter and polyadenylated via the ADH gene.

2. Preparation and Expression of Expressible MHC Class II Genes

A. Amplification and Expression of MHC Class II Genes

Genes or cDNAs encoding any preferred mammalian MHC Class II are cloned via use of the polymerase chain reaction (PCR). The primers described herein are used to amplify the appropriate Class II cDNAs in separate reactions which are then cloned and sequenced. To create MHC class II proteins, full length murine IA$^d$ α- and β-chain cDNAs were first obtained followed by PCR amplification and modification. The complete nucleotide sequences of the murine IA$^d$ α-chain cDNA is described by Benoist et al., *Cell*, 34:169–177 (1983) and is also listed in Genebank Accession Number K01923. The complete nucleotide sequences of the murine IA$^d$ β-chain cDNA is described by Malissen et al., *Science*, 221:750–754 (1983) and is also listed in GenBank Accession Numbers K00007 and K00008. To amplify each chain, mouse splenocytes were used as a source of total RNA. First strand cDNA was synthesized by using oligo(dT) and avian myeloblastosis virus reverse transcriptase. The resulting cDNA was used in a PCR amplification reaction utilizing the appropriate primers described below and a GeneAmp kit and thermal cycler (Perkin-Elmer/Cetus, Norwalk, Conn.). Reaction conditions preferably contained 1 μg cDNA template and 200 nM of each oligonucleotide primer. Thirty cycles were run as follows: (a) 1 minute at 92° C.; (b) 1 minute at 60° C.; and (c) 1 minute at 72° C. The PCR reaction was then heated to 99° C. for 10 minutes to inactivate the Taq polymerase and the ends of the DNA were made blunt by T4 polymerase (Stratagene, La Jolla, Calif.).

For all the oligonucleotide primers indicated in the Examples, the 5' primer is also referred to as the forward primer or sense primer as it has the same sequence as the top strand of the cDNA for hybridizing to the complementary bottom strand. In contrast, the 3' primer is also referred to as the backward primer or anti-sense primer as it has the same sequence as the bottom strand of the cDNA for hybridizing to the complementary top strand. Both primers are written in the 5' to 3' direction. The full length $IA^d$ α-chain cDNA was amplified with the 5' primer having the nucleotide sequence 5'CTTGAATTCCACCATGCCGTGCAGCA-GAGCTCTGA3' (SEQ ID NO 3). The 5' primer was also designed with an Eco RI restriction site to allow for directional ligation of the amplified products into recipient expression vectors. The 3' primer 5'TTTGGATCCTCAT-AAAGGCCCTGGGTGTC3' (SEQ ID NO 4) was also designed to contain a Bam HI restriction site.

The full length $IA^d$ β cDNA was amplified with the 5' forward primer having the nucleotide sequence 5'CTTGAATTCCACCATGGCTCTGCAGATCCCCA3' (SEQ ID NO 5). The 5' primer was also designed with an Eco RI restriction site to allow for directional ligation of the amplified products into recipient expression vectors. The 3' primer 5'TTTGGATCCTCACTGCAGGAGCCCTGCT3' (SEQ ID NO 6) was designed to contain a Bam HI restriction site. The modified cDNAs encoding the murine $IA^d$ α- and β-chains were first separately directionally cloned into the polylinker at the Eco RI and Bam HI restriction sites of the metallothionein promoter-driven pRmHa-3 vector, then sequenced by dye terminator technique on an Applied Biosystem 373A automated sequencer.

The complete nucleotide sequences of the murine $IA^d$ α- and β-chain amplified regions cloned into pRmHa-3 are respectively listed in SEQ ID NOs 7 and 8.

The separate plasmids were then transfected into *Drosophila melanogaster* Schneider-2 cells (ATCC CRL 10974, Rockville, Md.) as described elsewhere (Jackson et al., *Proc. Natl. Acad. Sci. U.S.A.*, 89;12117–21 1992). Equal amounts of the plasmids encoding the two class II chains were cotransfected together with a neomycin resistance gene, plasmid phshsneo (Bunch et al., *Nuc. Acids Res.*, 16:1043–1061 (1988) at a ratio of 1:30 to produce stable cell lines that were derived by G418 selection in Schneider's *Drosophila* medium (Gibco/BRL, Grand Island, N.Y.) supplemented with 10% fetal calf serum (heat treated for 1 hour at 55° C.), 100 units/ml penicillin, 100 μg/ml streptomycin, and 1 mM glutamine over a period of 4 weeks. Specifically, after transfection, the supernatant was carefully removed and the cells were transferred to a 75cm² flask in a total volume of 12 ml Schneider medium containing 500 μg/ml Geneticin (G418) (Gibco/BRL, Grand Island, N.Y.). After 4 days, 4 ml of the culture were transferred to a fresh flask containing 6 ml of Schneider medium with 500 μg/ml G418. This procedure was repeated every 4–7 days until a stable population of cells emerged which weakly adhered to the flask and grew with a doubling time of approximately 24 hours. These cells were subsequently cultured and passaged in the selection media as described above. Frozen aliquots of the stably transfected cells were prepared by collecting 5–20×10⁶ cells by centrifugation and resuspending them in 1 ml of cell freezing media (93% fetal calf serum/7% dimethylsulfoxide). Aliquots were then placed at −70° C. for 1 week and subsequently transferred to liquid nitrogen storage. Expression of the stably transfected MHC class II $IA^d$ α- and β-chain genes was induced with 0.7 mm cupric sulfate for 24 hours at 27° C.

Expression of MHC class II $IA^d$ heterodimers at the cell surface of the transfected *Drosophila* cells was evaluated by flow cytometry after staining with MKD6, an $IA^d$-specific monoclonal antibody (Kappler et al., *J. Exp. Med.*, 153:1198 (1981). Briefly, aliquots of cells (5×10⁵) were transferred into tubes on ice, collected by centrifugation (1,000×g for 5 minutes), resuspended in 0.1 ml of *Drosophila* medium with 5% horse serum containing the appropriate primary antibody (MKD6). After a 20 minute incubation at room temperature, cells were washed twice in 3 ml of Schneider's medium containing horse serum and resuspended in 0.1 ml of medium containing FITC-labeled secondary antibody (Cappell, Durham, N.C.). After a 20 minute incubation on ice, cells were washed twice with Schneider's medium containing horse serum and resuspended in this buffer at a concentration of 1×10⁶/m. Propidium iodide was added to permit exclusion of dead cells from the analysis. Samples were then analyzed by FACScan or FACSort instrument (Becton Dickinson). Synthetic antigen presenting cells of this invention that express the murine $IA^d$ MHC class II haplotype, described herein and well known in the art, with one or more accessory molecules were produced as described below.

Full-length human MHC class II α- and β-chains for the DR, DQ and DP haplotypes are amplified from peripheral blood cells which include B cells, macrophages and dendritic cells. The 5' and 3' primers used for amplifying each of the haplotypes have the following sequences:

DR α: 5' primer=5'CCACCATGGCCATTAGTGGAGTC3' (SEQ ID NO 9) 3' primer=5'TTTGGATCCTTACAGAGGCCCCCTGCG TT3' (SEQ ID NO 10);

DR β: 5' primer=5'CCACCATGGTGTGTCTGAGGCTCC3' (SEQ ID NO 11) 3' primer=5'TTTGGATCCTCAGCTCAGGAATCCTCT TG3' (SEQ ID NO 12);

DQ α: 5' primer=5'CCACCATGGTCCTAAACAAAGCTCTG AT3' (SEQ ID NO 13) 3' primer=51TTTGGATCCTCACAAGGGCCCTTGGTG TCT3t (SEQ ID NO 14);

DQ β: 5' primer=5'CCACCATGGCTTGGAAGAAGGCCTTT3' (SEQ ID NO 15) 3' primer=5'TTTAGATCTCAGTGCAGAAGCCCTTT3' (SEQ ID NO 16);

DP α: 5' primer=5'CCACCATGGGCCCTGAAGACAGAAT3' (SEQ ID NO 17) 3' primer=5'TTTGGATCCTCACAGGGTCCCCTGGGC3' (SEQ ID NO 18);

DP β: 5' primer=5'CCACCATGGTTCTGCAGGTTTCTGCG3' (SEQ ID NO 19) 3' primer=5'TTTGGATCCTTATGCAGATCCTCGTTG AA3' (SEQ ID NO 20).

The amplification conditions for obtaining the above human haplotypes are identical to those described above for the murine counterparts.

Synthetic antigen presenting cells of this invention that express a human MHC class II haplotypes, described herein and well known in the art, with one or more accessory molecules are produced as described below.

B. Amplification of Invariant and HLA-DM Chain cDNAs

For some aspects of the present invention as described in Section B in the detailed description, the invariant chain and HLA-DM α and HLA-DM β are co-expressed with a selected MHC class II heterodimer and at least one accessory molecule described above. In this instance, the MHC class II α- and β-chains, invariant chain and HLA-DM a- and E-chains are transfected into recipient antigen presenting cells in molar ratios 5:5:8:1:1. The ratio of accessory molecules to the molar ratio of the other genes is 1:1. The resultant transfected cells are then induced for expression of the exogenous genes as described above to generate a synthetic antigen presenting cell line of this invention.

1) Invariant Chain

The murine invariant chain cDNA is generated from mouse spleen cells. The full-length invariant chain is amplified from this source with the primer pair of a 5' and 3' primer having the respective nucleotide sequences 5'AAGAATTCACTAGAGGCTAGAGCCAT3' (SEQ ID NO 21) and 5'AAGGATCCTCACAGGGTGACTTGACC3' (SEQ ID NO 22). As described above, the 5' and 3' primers were designed to respectively incorporate Eco RI and Bam HI restriction sites. Following cloning of the amplified invariant chain into a Eco RI/Bam HI-digested pRmHa-3 vector, the resultant clone was sequenced and determined to have the sequence listed in SEQ ID NO 23.

The human invariant chain cDNA used in this invention is generated using RNA from γ-interferon-induced HeLa cells (ATCC Accession Number CCL 2). The resultant cDNA is then used as a template in PCR with the 5' and 3' oligonucleotide primers having the respective nucleotide sequences 5'AAGAATTCACCATGGATGATCAGCGC-GACCTT3' (SEQ ID NO 24) and 5'AAAGGATCCTCA-CATGGGGACTGGGCCCAGA3' (SEQ ID NO 25). The resulting PCR fragments are cleaved with Eco RI and Bam HI before ligation into similarly digested pRmHa-3.

2) HLA-DM

Messenger RNA from γ-interferon-induced HeLa cells is also used to synthesize the α- and β-chains of HLA DM cDNA that is then used as a template in PCR. The α-chain is amplified with the 5' and 3' primer pair having the respective nucleotide sequences 5'AAACCATGGGTCAT-GAACAGAACCA3' (SEQ ID NO 26) and 5'TTTGTC-GACTCAGTCACCTGAGCAAGG3' (SEQ ID NO 27). The β-chain is amplified with the 5' and 3' primer pair having the respective nucleotide sequences 5'AAACCATGGTCT-CATTCCTGCC3' (SEQ ID NO 28) and 5'TTTGTCGAC-CTAGGAAATGTGCCATCC3' (SEQ ID NO 29). The resulting PCR fragments are cleaved with Nco I and Sal I before separate ligation into a similarly digested pRmHa-3.

C. Amplification of Genes Encoding Accessory Molecules

1) Adhesion Molecules a. ICAM-1. ICAM-2, and ICAM-3

For isolating murine ICAM-1, spleen cells were isolated from Balb/c mice. The spleen cells were first stimulated with conA before isolation of mRNA using the FastTrack kit (Invitrogen, San Diego, Calif.) according to the manufacturers' instructions. cDNA was synthesized from the mRNA as described above. The resultant cDNA was then subjected to PCR with the following respective 5' and 3' primers that were designed based on the published cDNA nucleotide sequence (Siu, G. et al., *J. Immunol.*, 143:3813–3820 (1989)): 5'TTTAGAATTCACCATGGCTTCAACCCGT-GCCAAG3' (SEQ ID NO 30) and 5'TTTAGTCGACT-CAGGGAGGTGGGGCTTGTCC3' (SEQ ID NO 31). The PCR products were then cleaved with the restriction enzymes Eco RI and Sal I and ligated into a similarly digested pRmHa-3.

The above expression construct was then co-transfected into *Drosophila* S2 cells with the murine IA$^d$ α- and β-chain genes prepared above using the calcium phosphate method as described above in the molar ratio of 1:1:1 of ICAM-1: α-chain:β-chain. Stably transfected cells were obtained as described above. Synthetic antigen presenting *Drosophila* S2 cells expressing the accessory molecule ICAM-1 with the IA$^d$ α- and β-chains on the surface of the cell were then produced by inducing expression as previously described.

In other embodiments, synthetic antigen presenting cells containing genes encoding ICAM-1, B7.1 and/or B7.2 in conjunction with the murine IA$^d$ molecules were also produced for generating synthetic antigen presenting cells as used in activation assays as described in Example 5.

Human ICAM-1 is similarly amplified from mRNA isolated from the human cell line K562, originated from human chronic myelogenous leukemia (ATCC Accession Number CCL-243) and cultured under recommended conditions (i.e., RPMI with 10% fetal calf serum at 37° C. with 5% $CO_2$). The PCR primers for amplifying the human accessory molecules are designed based on known available sequences and in consideration of the 5' and 3' cloning sites needed to clone into the appropriate vectors. The nucleotide sequence of human ICAM-1 cDNA is available through GenBank Accession Number GB J03132. The ICAM-1 5' and 3' primers have the respective nucleotide sequences 5'ACCCT-TGAATTCATGGCTCCCAGCAGCCCCCGGCCC3' (SEQ ID NO 32) and 5'ATTACCGGATCCTCAGGGAGGCGTG-GCTTGTGTGTTCGG3' (SEQ ID NO 33).

PCR is performed with these primers as previously described to obtain amplified human ICAM-1. The resultant PCR products are then cloned into pRmHa-3 as previously described followed by transfection into recipient cells, also as previously described.

Similarly, human ICAM-2 and ICAM-3, the nucleotide sequences of which are available with the respective GenBank Accession Numbers GB X15606 and GB S50015, are amplifed with comparable primer pairs. The respective 5' and 3' primers for amplifying ICAM-2 have the nucleotide sequence 5'AAGGTACCCGTGGAGACTGCCAGAGAT3' (SEQ ID NO 34) and 5'TTTGGATCCCTATGGCCG-GAAGGCCTG3' (SEQ ID NO 35). The respective 5' and 3' primers for amplifying ICAM-3 have the nucleotide sequence 5'AAGAATTCCTGTCAGAATGGCCACCAT3' (SEQ ID NO 36) and 5TTTAGATCTTCACTCAGCTCTG-GACGGT (SEQ ID NO 37). The resultant amplified ICAM products are then separately ligated into pRmHa-3 and separately transfected into *Drosophila* S2 cells.

Synthetic antigen presenting *Drosophila* S2 cells expressing the accessory molecule ICAM-1 with a selected human MHC class II haplotype on the surface of the cell are then produced by inducing expression as previously described.

In other embodiments, synthetic antigen presenting cells containing genes encoding ICAM-1, ICAM-2 or ICAM-3 in combination with B7.1 and/or B7.2 along with a human haplotype are also produced for generating synthetic antigen presenting cells as used in activation assays as described in Example 5. Additional permutations contemplated for use in this invention include the above combinations with LFA-3 and/or Fas ligand (FasL), both of which are other accessory molecules as described below.

b. LFA-3

Human LFA-3 is isolated from blood lymphocytes. The nucleotide sequence of human LFA-3 cDNA is available through GenBank Accession Number GB 109083. Human LFA-3 is amplified accordingly with a 5' and 3' primer having the respective nucletide sequences 5'ACCCT-TGAGCTCATGGTTGCTGGGAGCGACGCGGGG3' (SEQ ID NO 38) and 5'ATTACCGGATCCTTAAAGAA-CATTCATATACAGCACAATACA3' (SEQ ID NO 39).

As described previously, synthetic antigen presenting cells containing genes encoding human LFA-3 alone or in various combinations with the other accessory molecules described herein along with a human haplotype are also produced for generating synthetic antigen presenting cells as used in activation assays as described in Example 5.

2) Costimulatory Molecules a. B7.1 cDNA was generated from mRNA isolated from mice as described above for ICAM-1. The resultant cDNA was then subjected to PCR with the following respective 5' and 3' oligonucleotide primers shown in the 5' to 3' direction that were designed based on the published cDNA nucleotide sequence (Freeman, et al., *J. Exp. Med.*, 174:625–631 (1991)): 5'TTTAGAATTCACCATGGCTTGCAATTGT-CAGTTG3' (SEQ ID NO 40) and 5'TTTAGTCGAC-CTAAAGGAAGACGGTCTGTTC3' (SEQ ID NO 41). The PCR products were cleaved with the restriction enzymes Eco RI and Sal I and ligated into a similarly digested pRmHa-3.

The above expression construct was then co-transfected into *Drosophila* S2 cells with the murine IA$^d$ α- and β-chain genes prepared above using the calcium phosphate method as described above in the molar ratio of 1:1:1 of B7.1:α-chain:β-chain. Stably transfected cells were obtained as described above. Synthetic antigen presenting *Drosophila* S2 cells expressing the accessory molecule B7.1 with the IA$^d$ α- and βchains on the surface of the cell were then produced by inducing expression as previously described.

In other embodiments, synthetic antigen presenting cells containing genes encoding murine ICAM-1, B7.1 and/or B7.2 in conjunction with the murine IA$^d$ molecules are also produced for generated synthetic antigen presenting cells as used in activation assays as described in Example 5.

Human B7.1 is similarly isolated from K562 cells and cloned into pRmHa-3 as described above. The nucleotide sequence of human B7.1 cDNA is available through Gen-Bank Accession Number GB M83071. The 5' and 3' primers have the respective nucleotide sequences, 5'ACCCT-TGAATCCATGGGCCACACACGGAGGCAG3' (SEQ ID NO 42) and 5'ATTACCGGATCCTTATACAGGGCGTA-CACTTTCCCTTCT3, (SEQ ID NO 43). The resultant PCR products are then inserted into pRmHa-3 that is then co-transfected along with amplified cloned human haplotype genes into *Drosophila* S2 cells.

Synthetic antigen presenting *Drosophila* S2 cells expressing the accessory molecule B7.1 with a selected human MHC class II haplotype on the surface of the cell are then produced by inducing expression as previously described.

In other embodiments, synthetic antigen presenting cells containing genes encoding human B7.1 in various combinations with the other accessory molecules described herein along with a human haplotype are also produced for generating synthetic antigen presenting cells as used in activation assays as described in Example 5.

b. B7.2

Murine IC-21 cells (ATCC Accession Number TIB 186) were propagated in RPMI 1640 medium containing 10% fetal calf serum. cDNA was synthesized from the mRNA isolated from these cells as described above. The resultant cDNA was then subjected to PCR with the following respective 5' and 3' oligonucleotide primers shown in the 5' to 3' direction that were designed based on the published cDNA nucleotide sequence (Freeman, et al., *J. Exp. Med.*, 178: 2185–2192 (1993)): 5'TTTAGAATTCACCATGGAC-CCCAGATGCACCATGGG3' (SEQ ID NO 44) and 5'TTTAGTCGACTCACTCTGCATTTGGTTTTGCTGA3' (SEQ ID NO 45). The PCR products were cleaved with the restriction enzymes Eco RI and Sal I and ligated into a similarly digested pRmHa-3.

The above expression construct was then co-transfected into *Drosophila* S2 cells with the murine IA$^d$ α- and β-chain genes prepared above using the calcium phosphate method as described above in the molar ratio of 1:1:1 of B7.2:α-chain:β-chain. Stably transfected cells were obtained as described above. Synthetic antigen presenting *Drosophila* S2 cells expressing the accessory molecule B7.2 with the IA$^d$ α- and β-chains on the surface of the cell were then produced by inducing expression as previously described.

In other embodiments, synthetic antigen presenting cells containing genes encoding murine B7.2 in conjunction with ICAM-1 and the murine IA$^d$ molecules were also produced following the procedures described above for generated synthetic antigen presenting cells as used in activation assays as described in Example 5.

Human B7.2 is isolated from the human cell line HL60, that originated from a human promyelocytic leukemia (ATCC Accession Number CCL-240). The nucleotide sequence of human B7.2 cDNA is available through Gen-Bank Accession Number GB M83071. The 5' and 3' primers for amplifying human B7.2 have the respective nucleotide sequences 5'ACCCTTGAGCTCATGGATCCCCAGTG-CACTATG3' (SEQ ID NO 46) and 5'ATTACCCCGGGT-TAAAAACATGTATCACTTTTGTCGCATGA3' (SEQ ID NO 47).

The amplified B7.2 products are then cloned into pRmHa-3 as previously described for tranfection into *Drosophila* S2 cells along with constructs for a selected human haplotype. Expression of the transfected genes is induced as previously described.

In other embodiments, synthetic antigen presenting cells containing genes encoding human B7.2 in various combinations with the other accessory molecules described herein along with a human haplotype are also produced for generating synthetic antigen presenting cells as used in activation assays as described in Example 5.

3. Survival Molecules

Human Fas ligand is isolated from activated human T cells. The nucleotide sequence of human Fas ligand cDNA is available through GenBank Accession Number GB U08137. Human Fas ligand is amplified accordingly with a 5' and 3' primer pair having the respective nucleotide sequences 5'AAAGGATCCACCATGCAGCAGCCCT-TCAATT3' (SEQ ID NO 48) and 5'TTTGGATCCTTA-GAGCTTATATAAGCCGA3' (SEQ ID NO 49).

Human CD70, the ligand for CD27 expressed on T cells, is amplified as described above with a 5' and 3' primer pair having the respective nucleotide sequences 5'AAAGAAT-TCGGTACCATGCCGGAGGAGGGTTCGG3' (SEQ ID NO 50) and S"TTTGGATCCTCAGGGGCGCACCCACTGCA3' (SEQ ID NO 51).

As described previously, synthetic antigen presenting cells containing genes encoding human Fas ligand alone or in various combinations with the other accessory molecules described herein along with a human haplotype are also produced for generating synthetic antigen presenting cells as used in activation assays as described in Example 5.

3. Preparation of MHC Class II Anchored on Synthetic Supports

The examples described herein present a new method to immobilize high amounts of MHC class II molecules and single accessory molecules or various combinations thereof on various surfaces (fly cells, red blood cells, latex beads) in native conformation as judged by monoclonal antibody binding and resetting experiments (T cell receptor binding). This method can be extended to other synthetic surfaces including artificial phospholipid membranes. Phosphatidylethanolamine as well as avidin-coupled phospholipids are particularly relevant this invention. These phospholipids are commercially available from Lipex Biomembrane Inc., Vancouver, BC, Canada.

A. Immobilization of Biotinylated MHC Class II on Avidin-Coated Red Blood Cells

NHS-LC-biotin, neutravidin and biotin-BMCC are purchased from Pierce (Rockford, Ill.). Sheep red blood cells are obtained from the Colorado Serum Company (Denver, Colo.). *Drosophila* S2 cells expressing MHC c.lass II are prepared as described above. Monoclonal antibodies MKD6 and M5-114 (ATCC Accession Number TIB 120 for the hybridoma secreting MKD6) are used as hybridoma cell culture supernatants. The protocol used is described by Muzykantov and Taylor (*Anal. Biochem.*, 223:142–148 (1994)). Briefly, SRBC are washed four times in PBS, biotinylated using NHS-LC-biotin, washed again 4 times in PBS, incubated with neutavidin, and finally washed four times and stored at 4° C. in PBS containing 3% fetal calf serum and 0.02% sodium azide. Recombinant expressed MHC class II α- and β-chains are biotinylated using biotin-BMCC, a maleimide-coupled biotin which reacts with thiol groups. Biotinylation is performed as recommended by the manufacturer. Unreacted biotin is removed using Centricon 10.

Biotinylated MHC class II α- and β-chains are immobilized by incubation at a final concentration of 0.2 mg/ml with avidin-coated SRBC for 30 minutes followed by washing in DMEM containing 10% fetal calf serum. SRBC with attached MHC class II are used immediately.

Immobilization of biotinylated MHC class II α- and β-chains on avidin-coated SRBC is done as indicated above. Attachment is assessed using flow cytofluorometry using the antibodies described above. For rosetting assays, either *Drosophila* S2 cells expressing MHC class II or MHC class II-coated SRBC are incubated with specific peptide (see Example 4) (0.02 mM) or an irrelevant peptide (0.02 mM) for 30 minutes on ice; CD4+ T cells are then added, the proportion being 10 T cells for one *Drosophila* S2 cell, or 10 SRBC for 1 T cell. The mixture is then pelleted and kept on ice for at least 30 minutes. Cells are then carefully resuspended and rosettes are counted, a rosette being a *Drosophila* S2 cell bound to at least 3 CD4+ T cells, or a CD4+ T cell bound to at least 3 SRBC.

B. Immobilization of Biotinylated MHC Class II on Avidin-Coated Latex Beads

Six micron diameter latex sulfate beads are purchased from Interfacial Dynamics Corporation (Portland, Oreg.) and biotinylated according to the protocol described above. Avidin-coated latex beads are prepared using a 1% suspension of the latex beads incubated in PBS containing 1 mg/ml of neutravidin for 1 hour at room temperature. An equal volume of PBS containing 10% fetal calf serum is then added. After 1 hour of incubation at room temperature, the beads are washed 3 times and used for binding of recombinant biotinylated MHC class II.

Recombinant biotinylated MHC class II is immobilized by incubation at a final concentration of 0.2 mg/ml with avidin-coated latex beads for 30 minutes followed by washing in DMEM containing 10% fetal calf serum. SRBC with attached MHC class II are used immediately. Rosetting experiments are performed as previously desribed.

C. Immobilization and Detection of MHC Class II Bound to Various Solid Supports Such as Plastic Microwell Plates The MHC class II molecules are immobilized by direct binding to microtiter plates (Corning) and detected as follows: MHC class II is diluted to a desired concentration in PBS, e.g. 1 mg/ml for 100 ng/well, and then added to each well on the plastic microtiter plate. The plate is incubated for 1 hour at room temperature. After incubation, the plate is washed once with PBS and 200 µl 2% bovine serum albumin (BSA) in PBS+(0.05%) and Tween (PBST) is added followed by incubation for another hour at room temperature. The plate is washed 3 times with PBST and biotinylated anti-MHC class II monoclonal antibody was added (1:2500) in 2% BSA in PBS. The plate is incubated another hour at room temperature and washed 3 times with PBST. Avidin conjugated HRP is added (1:2500) in 2% BSA in PBS. Following another hour of incubation at room temperature, the plate is washed 3 times with PBST and $H_2O_2$ or thophenyldiamine was added. The reaction is stopped with $H_2SO_4$. Reaction product is detected colorimetrically at 490 nm. Recombinant MHC class II molecules can alternatively be bound through biotin-avidin linked interactions with the substrate. In this embodiment, the microwell plates are coated with 100 µl avidin diluted in PBS to a concentration of 0.001 mg/ml. Excess avidin is removed by a PBS wash. The above procedure for presenting and detecting MHC class II binding is followed.

Recombinant MHC molecules are alternatively immobilized by a linkage based on a poly-histidine tag added to the MHC interacting with the nickel bound to the substrate.

The above procedure for binding and detection is followed using nickel chelate coated microwell plates (Xenopore) and expressed recombinant MHC molecules with a poly-histidine tag.

4. Peptide Generation

Antigenic peptides according to the present invention are obtained from naturally-occurring sources, including those described in the specification, or may be synthesized using known methods. In various examples disclosed herein, all peptides were separately chemically synthesized by T-BOC chemistry on an Applied Biosystem instrument, ABI 431A (Foster City, Calif.), and purified on a C18 reverse phase column. Isolation or synthesis of peptides generated from a random assortment of amino acid residues may also be appropriate, particularly when one is attempting to ascertain a particular epitope in order to load an empty MHC molecule with a peptide most likely to stimulate CD4 cells. Mixtures of randomized peptides are obtained by using proteasomes, by subjecting a protein or polypeptide to a degradative process, such as digestion with chymotrypsin, or by synthesis.

While the cell lines of the present invention are able to degrade proteins and polypeptides into smaller peptides capable of being loaded onto human MHC class II molecules, it is preferable to introduce the peptides directly into the cell culture to facilitate a more rapid loading and expression process.

If peptides are synthesized having randomly incorporated amino acid residues, all varieties of amino acids, L or D conformations as well as modified amino acids, are preferably incorporated during each cycle of the synthesis. It should be noted, however, that various parameters, e.g., solvent incompatibility of certain amino acids, may result in a mixture which contains peptides lacking certain amino acids. The process should thus be adjusted as needed, by altering solvents and reaction conditions, to produce the greatest variety of peptides. A peptide used for peptide loading as described in Example 5 with murine MHC class II is ovalbumin$_{323-339}$ (OVA) having the amino acid residue sequence ISQAVHAAHEINEAGR (SEQ ID NO 52). Preferred peptides specific for human MHC class II haplotypes include the following peptides: 1) Influenza hemagglutinin$_{306-318}$ PKYVKQNTLKLAT (SEQ ID NO 53) that binds HLA-DRB1*0101; 2) HSP65$_{2-12}$ from *M. tuberculosis* KTI-ATDEEARR (SEQ ID NO 54) that binds HLA-DRB1*0301; 3) Mitochondrial outer protein (MOMP) of *C. trachomatis* QASLALSYRLNMFTP (SEQ ID NO 55) that binds HLA-DRB1*0301; and 4) HLA-A2$_{33-45}$ FVRFDS-DAASQRM (SEQ ID NO 56) that binds to HLA-DRB1*0401. An extensive listing of known class II-binding peptides as well as a description of how peptide ligands are defined is presented by Rammensee et al., *Immunogenetics*, 41:178–228 (1995). Peptides for use in practicing the methods of this invention are also available through Chiron Mimetopes. In other embodiments, peptide libraries, readily produced by one of ordinary skill in the art, are contemplated for use in practicing the methods of this invention with the synthetic antigen presenting cells as described herein.

5. Loading of Empty MHC Class II Molecules by In Vitro Incubation with Peptides

As shown by the results presented below, the murine MHC class II molecules along with selected accessory molecules expressed on the surface of *Drosophila* cell lines, having been transfected with various combinations of plasmids encoding MHC class II and accessory molecules, bind specific peptides in a dose-dependent fashion and are able to present these peptides to antigen specific T cells resulting in T cell activation.

For the proliferation and activation assays performed below, *Drosophila melanogaster* Schneider 2 (SC2) cells (ATCC Accession Number CRL 10974) were transformed with genes encoding the MHC class II α- and β-chain from H2-A$^d$ as described in Example 2. For other assays where selected accessory cells were expressed in combination with the MHC class II molecules, the genes for B7.1, B7.2 and ICAM-1, were also introduced into the MHC gene-containing cells as previously described.

The accessory molecules were expressed at selected concentrations and in combinations as defined below to permit reproducible and consistent activation of CD4$^+$ cells. Following expression, induced by treatment with copper sulfate, the concentrations of expressed molecules were monitored. Selection of cells expressing the desired levels of molecules was performed with flow cytometry sorting of cell lines. Table I lists the *Drosophila* cell lines expressing murine IA$^d$ MHC class II molecules alone or in combination with various accessory molecules. The table also presents a summary of the results of proliferative effects, described further below, as indicated with a "−" for no effect and a "+" for a positive proliferative effect. A summary of the types of cytokines produced by each type of synthetic antigen presenting cell is also indicated, and described further below, with the additional notation with arrows of whether a particular cytokine production was up or down regulated.

TABLE 1

| Accessory Molecules | Proliferative Responses | Cytokines Produced |
|---|---|---|
| None | − | − |
| B7.1 | + | IL-4, IL-10, IL-2 |
| B7.2 | + | IL-4, IL-10, IL-2 |
| ICAM-1 | − | − |
| B7.1 + B7.2 | + | IL-4, IL-10, IL-2 |
| B7.1 + ICAM-1 | + | ↑IL-2, ↓IL-4, ↓IL-10 |
| B7.2 + ICAM-1 | + | ↑IL-2, ↓IL-4, ↓IL-10 |
| CD70 + ICAM-1 | + | IL-2 |
| CD70 | − | − |
| CD70 + ICAM-1 + B7.2 | + | ↑IL-2 |

For assessing the effect of antigen presentation and ultimately T cell response, the antigen specific T cells were CD4$^+$ cells obtained from T cell receptor transgenic mice. The transgenic line as used herein was D01 which expresses a T cell receptor specific for the ovalbumin peptide 323–339. The D01 mouse line is obtained from Dr. Dennis Lo. For assaying T cell responsiveness to the recombinant surface-expressed MHC class II molecules, CD4$^+$ cells were first purified from lymph nodes using a combination of techniques designed to eliminate all host APC from the responder population. Small numbers (5×10$^4$) of these highly purified CD4$^+$ cells were then cultured with the *Drosophila* cell lines in the presence or absence of ova peptide.

The effect of peptide presentation in the presence of MHC class II with and without accessory molecules, B7.1, B7.2 or B7.2 plus ICAM-1, was first assessed in a proliferation assay performed as described by Webb et al., *Cell*, 63:1249 (1990). Briefly, 5×10$^4$ CD4$^+$ T cells were cultured in microtiter wells with 5×10$^4$ *Drosophila* cells in 300 μl of culture medium. Eighteen hours prior to harvesting, 100 μl of supernatant were removed for cytokine analysis and 1 μCi of $^3$H-thymidine was added to each well. At the times indicated (3, 4 or 5 days), the wells were individually harvested onto glass fiber filters and counted in a liquid scintillation counter.

Figure 2:
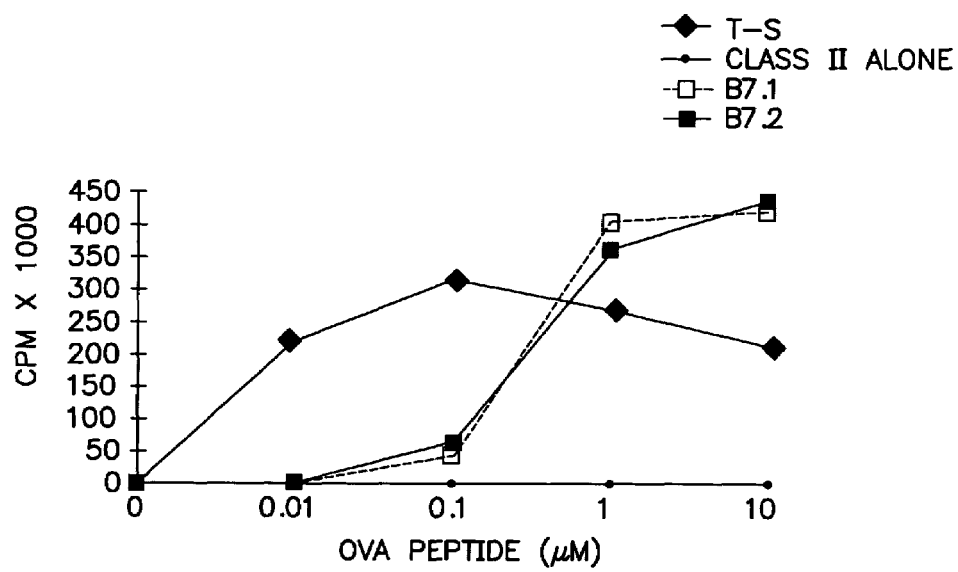
FIG. 2 shows the proliferative response of DO10 T cell receptor (TCR) transgenic mouce cell line (Tg cells) when cultured in the presence of *Drosophila* cell lines with or without ovalbumin (OVA) peptide loaded onto the surface-expressed MHC class II heterodimer. Proliferation is assayed as Edescribed in Example 5. The proliferation is measured in counts per minute (cpm)×1000 as plotted on the Y-axis against increasing concentrations of OVA peptide in μM on the X-axis. T-S (diamond marked line) shows responses with control splenic APC. Proliferative responses with recombinant MHC class II alone are shown in the line having closed circles. Those with MHC class II combined with either costimulatory molecules B7.1 or B7.2 are shown respectively with lines having open and closed squares.

As seen in FIG. 2, cell lines expressing MHC class II molecules alone failed to stimulate T cell proliferative responses as indicated by the low incorporation of radioactive thymidine; higher counts indicate greater proliferation plotted against the amount of stimulating peptide in μM. However, co-expression of either B7.1 or B7.2 costimulatory molecules conferred the capacity of MHC class II presented-ova peptide to stimulate strong proliferative responses. For comparison, the results with splenic APC (labeled T-S) are shown in FIG. 2.

Figure 3:
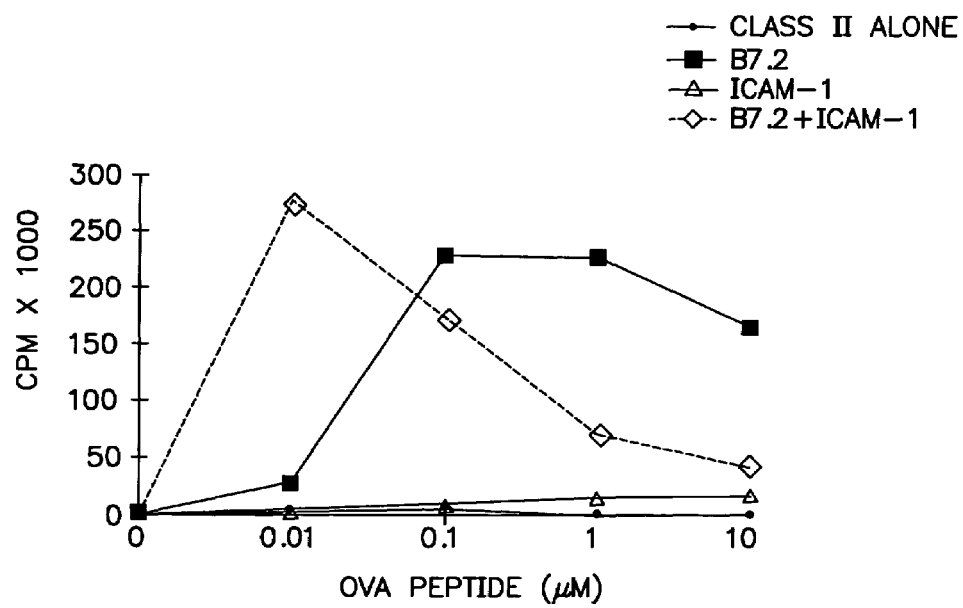
FIG. 3 shows proliferative responses to recombinant MHC class II alone (closed circle line), with MHC class II plus B7.2 (closed square line), with MHC class II plus ICAM-1 (open triangle line) and with MHC class II plus B7.2 and ICAM-1 (open diamond line). Refer to FIG. 2 legend for other details.

As shown in FIG. 3, *Drosophila* cell lines expressing MHC class II molecules with the adhesion molecule ICAM-1 were nonstimulatory. However, the expression of ICAM-1 together with B7.2 generated a synthetic APC cell line that stimulated proliferative responses at lower concentrations of peptide antigen. These results demonstrate that *Drosophila* cell lines expressing the murine H2-A$^d$ MHC class II molecules and costimulatory molecules, B7.1, B7.2 and B7.2 plus ICAM-1, are able to activate naive CD4$^+$ T cells as measured by an increase in proliferation.

In addition to proliferation, the reproducible activation of CD4$^+$ T cells to produce particular cytokines was desired. Thus, the cytokines produced in the cultures described above were also evaluated using standard ELISA methods with antibodies specific for the cytokine to be measured. The data plotted in FIGS. 4A–4D and 5A–5D indicate the amount of cytokine produced in ng/ml concentrations against the stimulatory molecules on APC.

The results of these assays indicate that different combinations of accessory molecules on *Drosophila* APC expressing recombinant MHC class II leads to the production of different cytokines as shown in FIGS. 4A–4D and FIGS. 5A–5D. For IL-2 production, a Th1 type response, cell lines expressing MHC class II with B7.1 or B7.2 were poorly stimulatory as shown in FIG. 4A. In order to achieve significant levels of IL-2, the *Drosophila* cell lines required co-expression of ICAM-1, B7 and class II (FIG. 5A). Production of γ-interferon was also poorly induced by *Drosophila* cell lines expressing B7.1 and B7.2 (FIG. 4D). In contrast to the results with IL-2, however, the co-expression of ICAM-1 did not restore γ-IFN production (FIG. 5C). Splenic APC (labeled as T-S)-induced strong γ-IFN production suggesting that additional molecules regulate the production of this cytokine.

IL-4 production, a Th2 type response, is generally not observed during primary stimulation of naive $CD4^+$ T cells. In keeping with these observations, splenic APC (T-S) failed to induce significant IL-4 after culture-with D01 cells and ova-peptide (FIG. 5B). However, *Drosophila* cells co-expressing class II MHC molecules with either B7.1 or B7.2 or both induced strong IL-4 production during culture (FIGS. 4B and 5B). Interestingly, the addition of ICAM-1 had an antagonistic influence on the production of this cytokine (FIG. 5B). IL-10 was similarly regulated to IL-4 as shown in FIGS. 4D and 5D.

As described above, the results with a cytokine profile of a Th2 type response, rather than a Th1 type response, were obtained with cell lines expressing B7 and MHC class II. In contrast, co-expression of MHC class II in combination with B7 and ICAM-1 antagonized the production of IL-4 and IL-10 while strongly promoting IL-2, thereby inducing a Th1 type response with support the present invention in the ability to drive the activation of $CD4^+$ T cells into desired T cell subsets. These results definitively show that *Drosophila* cell lines can be tailored to express defined combinations of accessory molecules for use in achieving a desired population of $CD4^+$ T cells that produce different patterns of cytokines. Thus, the compositions and methods described herein validate the compositions and methods of use of the present invention.

The foregoing is intended to be illustrative of the present invention, but not limiting. Numerous variations and modifications may be effected without departing from the true spirit and scope of the invention.

What is claimed is:

1. A method of producing an insect synthetic antigen presenting cell comprising:
   a) transforming the cell with an expressible MHC class II α-chain gene operably linked to a first promoter in a vector capable of expressing an MHC class II α-chain;
   b) transforming the cell with an expressible MHC class II β-chain gene operably linked to a second promoter in a vector capable of expressing an MHC class II β-chain; and
   c) transforming the cell with a first expressible accessory molecule gene operably linked to a third promoter in a vector capable of expressing an accessory molecule, wherein the accessory molecule is selected from the group consisting of: a B7.1, a B7.2, an ICAM-1, an ICAM-2, an ICAM-3, an LFA-3, a Fas ligand, and a CD70.

2. The method of claim 1 wherein the cell lacks a gene coding for at least one of the α-chain, the β-chain and the accessory molecule genes prior to transformation.

3. The method of claim 1 further comprising the step of transforming the cell with an expressible antigen processing assisting gene operably linked to a fourth promoter in a vector capable of expressing an antigen processing assisting molecule.

4. The method of claim 1 wherein the α- and β-chain genes are of human origin.

5. The method of claim 1 wherein at least one promoter is inducible.

6. The method of claim 1 wherein the α-, β-and accessory molecule genes are present in the same vector.

7. The method of claim 1 wherein the α-, β-and accessory molecule genes are present in separate vectors.

8. The method of claim 1, wherein the accessory molecule gene encodes one or more of a costimulatory molecule selected from the group consisting of a B7.1 and a B7.2, an adhesion molecule selected from the group consisting of an ICAM-1, an ICAM-2, an ICAM-3, and an LFA-3, or a survival molecule selected from the group consisting of a Fas ligand and a CD70.

9. The method of claim 1 further comprising the step of transforming the cell with an expressible neomycin resistance gene operably linked to a vector.

10. The method of claim 1 wherein the accessory molecule gene encodes a costimulatory molecule selected from the group consisting of a B7.1 and a B7.2.

11. The method of claim 1 wherein the accessory molecule gene encodes an adhesion molecule selected from the group consisting of an ICAM-1, an ICAM-2, an ICAM-3 and an LFA-3.

12. The method of claim 1 wherein the accessory molecule gene encodes a survival molecule selected from the group consisting of a Fas ligand and a CD70.

13. The method of claim 1 wherein the insect cell is selected from the group consisting of *Spodoptera* and *Drosophila*.

14. The method of claim 13, wherein the accessory molecule gene encodes one or more of a costimulatory molecule selected from the group consisting of a B7.1 and a B7.2, an adhesion molecule selected from the group consisting of an ICAM-1, an ICAM-2, an ICAM-3, and an LFA-3, or a survival molecule selected from the group consisting of a Fas ligand and a CD70.

15. The method of claim 13, wherein the accessory molecule gene encodes a costimulatory molecule selected from the group consisting of a B7.1 and a B7.2.

16. The method of claim 13, wherein the accessory molecule gene encodes an adhesion molecule selected from the group consisting of an ICAM-1, an ICAM-2, an ICAM-3, and an LFA-3.

17. The method of claim 13, wherein the accessory molecule gene encodes a survival molecule selected from the group consisting of a Fas ligand and a CD70.

18. The method of claim 13, wherein the accessory molecule gene encodes one or more of a B7.1, a B7.2, an ICAM-1, an ICAM-2, an ICAM-3, an LFA-3, a Fas ligand, or a CD70.

19. The method of claim 1 further comprising the step of transforming the cell with a gene for a second accessory molecule, wherein the second accessory molecule is selected from the group consisting of: a B7.1, a B7.2, an ICAM-1, an ICAM-2, an ICAM-3, an LFA-3, a Fas ligand, and a CD70.

20. The method of claim 19 wherein the first accessory molecule is a costimulatory molecule selected from the group consisting of a B7.1 and a B7.2 and the second accessory molecule is an adhesion molecule selected from the group consisting of an ICAM-1, an ICAM-2, an ICAM-3, and an LFA-3.

21. The method of claim 19 wherein the first accessory molecule is a costimulatory molecule selected from the group consisting of a B7.1 and a B7.2 and the second accessory molecule is a survival molecule selected from the group consisting of a Fas ligand and a CD70.

22. The method of claim 19 wherein the first accessory molecule is a survival molecule selected from the group consisting of a Fas ligand and a CD70 and the second accessory molecule is an adhesion molecule selected from the group consisting of an ICAM-1, an ICAM-2, an ICAM-3, and an LFA-3.

23. The method of claim 19 further comprising the step of transforming the cell with a gene for a third accessory molecule, wherein the third accessory molecule is selected from the group consisting of: a B7.1, a B7.2, an ICAM-1, an ICAM-2, an ICAM-3, an LFA-3, a Fas ligand, and a CD70.

24. The method of claim 23 wherein the first accessory molecule is a costimulatory molecule selected from the group consisting of a B7.1 and a B7.2, the second accessory molecule is an adhesion molecule selected from the group consisting of an ICAM-1, an ICAM-2, an ICAM-3, and an LFA-3, and the third accessory molecule is a survival molecule selected from the group consisting of a Fas ligand and a CD70.

* * * * *

UNITED STATES PATENT AND TRADEMARK OFFICE
CERTIFICATE OF CORRECTION

PATENT NO. : 7,074,617 B1 Page 1 of 1
APPLICATION NO. : 09/715891
DATED : July 11, 2006
INVENTOR(S) : Susan R. Webb et al.

It is certified that error appears in the above-identified patent and that said Letters Patent is hereby corrected as shown below:

On the Title Page item (54) and (75) should read as follows:

(54) MHC CLASS II ANTIGEN-PRESENTING SYSTEMS AND METHODS FOR ACTIVATING CD4+T CELLS

(75) Inventors: Susan R. Webb, Leucadia, CA (US;
Ola Winqvist, Uppsala (SE);
Lars Karlsson, La Jolla, CA (US);
Michael R. Jackson, Del Mar, CA (US)
Per A. Peterson, Rancho Santa Fe, CA (US)

Signed and Sealed this

Twenty-fourth Day of October, 2006

JON W. DUDAS
*Director of the United States Patent and Trademark Office*